US011254651B2

(12) United States Patent
Yu et al.

(10) Patent No.: US 11,254,651 B2
(45) Date of Patent: Feb. 22, 2022

(54) HISTONE METHYLTRANSFERASE INHIBITORS

(71) Applicant: GLOBAL BLOOD THERAPEUTICS, INC., South San Francisco, CA (US)

(72) Inventors: Ming Yu, Foster City, CA (US); Zhe Li, San Diego, CA (US); Lina Q. Setti, Fremont, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/076,307

(22) PCT Filed: Feb. 15, 2017

(86) PCT No.: PCT/US2017/017977
§ 371 (c)(1),
(2) Date: Aug. 7, 2018

(87) PCT Pub. No.: WO2017/142947
PCT Pub. Date: Aug. 24, 2017

(65) Prior Publication Data
US 2019/0047981 A1 Feb. 14, 2019

Related U.S. Application Data

(60) Provisional application No. 62/296,484, filed on Feb. 17, 2016, provisional application No. 62/351,208, filed on Jun. 16, 2016.

(51) Int. Cl.
| | | |
|---|---|---|
| C07D 401/12 | (2006.01) | |
| C07D 405/14 | (2006.01) | |
| A61P 37/00 | (2006.01) | |
| A61P 7/00 | (2006.01) | |
| A61P 29/00 | (2006.01) | |
| A61P 35/00 | (2006.01) | |
| C07D 401/14 | (2006.01) | |

(52) U.S. Cl.
CPC .............. *C07D 401/12* (2013.01); *A61P 7/00* (2018.01); *A61P 29/00* (2018.01); *A61P 35/00* (2018.01); *A61P 37/00* (2018.01); *C07D 401/14* (2013.01); *C07D 405/14* (2013.01)

(58) Field of Classification Search
CPC .................................................. C07D 401/12
See application file for complete search history.

(56) References Cited

U.S. PATENT DOCUMENTS

| | | | | |
|---|---|---|---|---|
| 4,107,288 A | | 8/1978 | Oppenheim et al. | |
| 5,145,684 A | | 9/1992 | Liversidge et al. | |
| 5,488,055 A | * | 1/1996 | Kumar | C07D 471/04 514/232.8 |
| 2008/0176889 A1 | * | 7/2008 | Su | A61P 35/00 514/297 |
| 2015/0274660 A1 | | 10/2015 | Pliushchev et al. | |

OTHER PUBLICATIONS

Skripkina "Methoxy derivatives of 7-sulfodimethylamidoacridine." Khimiya Geterotsiklicheskikh Soedinenii, 7(1), 115-17, 1971 (STN abstract only).*
Nickel, P "Antimalarial 6-aminoquinolines. XI. Some 2-, 3-, and 4-alkyl-, aryl-, and arylalkyl derivatives.".Arzneimittel-Forschung, 1978, 28(5), 723-31 (STN abstract only).*
STN-Chemical database registry #5438-91-5 entry for alpha-[(dipropylamino)methyl]-5,6,7,8-tetrahydro-3-Acridinemethanol, Hydrochloride Entered STN: Nov. 16, 1984.*
Jose-Eneriz "Discovery of first-in-class reversible dual small molecule inhibitors against G9a and DNMTs in hematological malignancies" Nature Communications (2017), 8, 15424.*
Liu, F. et al. "Discovery of a 2,4-diamino-7-aminoalkoxyquinazoline as a potent and selective inhibitor of histone lysine methyltransferase G9a." J. Med. Chem. 2009, 52, 7950-7953.*
Pozharskii et al. Heterocycles in Life and Society Wiley, 1997, pp. 1-6.*
Pitt "Heteroaromatic Rings of the Future" J. Med. Chem. 2009, 52, 2952-2963.*
Online "https://pubchem.ncbi.nlm.nih.gov/substance/540857" accessed Jan. 8, 2019.*
Shah "The role of fluorine in medicinal chemistry" Journal of Enzyme Inhibition and Medicinal Chemistry, Oct. 2007; 22(5): 527-540.*
STN chemical database entry for 6-chloro-2-methoxy-3-[3-(2-methyl-1-piperidinyl)propyl]-9-Acridinamine, RN: 1071758-03-6 REGISTRY entered STN Nov. 9, 2008.*
Belmont "Introduction of a nitroxide group on position 2 of 9-phenoxyacridine: easy access to spin labeled DNA-binding conjugates." Bioorganic & Medicinal Chemistry Letters, 8(6), 669-674, 1998.*
Antignano et al., "Methyltransferase G9A regulates T cell differentiation during murine intestinal inflammation" J. Clin. Invest. (2014) 124(5): 1945-55.
Cascielle et al., "Functional role of G9a histone methyltransferase in cancer" Front Immunol. (2015) 6:Article 487:1-12.
Charache et al., "Hydroxyurea: Effects on Hemoglobin F Production in Patients With Sickle Cell Anemia" Blood (1992) 79(10):2555-2565.
Fieser, M., Fieser and Fieser's Reagents for Organic Synthesis, vols. 1-17 (1991) Ed., John Wiley & Sons, New York, New York, Cover and Table of Contents.
Gennaro, AR., Remington's Pharmaceutical Sciences, (1985) 17th Ed., Mack Publishing Co., Easton, PA, Cover and Table of Contents.

(Continued)

*Primary Examiner* — David K O'Dell
(74) *Attorney, Agent, or Firm* — Alston & Bird LLP

(57) ABSTRACT

The present disclosure provides certain compounds that are histone methyltransferases G9a and/or GLP inhibitors and are therefore useful for the treatment of diseases treatable by inhibition of G9a and/or GLP such as cancers and hemoglobinpathies such as beta-thalassemia and sickle cell disease. Also provided are pharmaceutical compositions containing such compounds as well as processes and intermediates for preparing such compounds.

20 Claims, No Drawings

(56) References Cited

OTHER PUBLICATIONS

Gennaro, AR., Remington's Pharmaceutical Sciences (2000) 20th Ed., Lippincott Williams & Wilkins, Baltimore, MD, Cover and Table of Contents.
Greene, et al., Protective Groups in Organic Synthesis, (1999) 3rd. Ed., John Wiley & Sons, Cover and Table of Contents.
Imai et al., "Involvement of Histone H3 Lysine 9 (H3K9) Methyltransferase G9a in the Maintenance of HIV-1 Latency and Its Reactivation by BIX01294" J. Biol. Chem. (2010) 285(22):16538-16545.
Krivega et al., "Inhibition of G9a methyltransferase stimulates fetal hemoglobin production by facilitating LCR/γ-globin looping," Blood (2015) 126(5):665-672.
Larock, R.C., Comprehensive Organic Transformations (1989) 2nd Ed., VCH Publishers, New York, NY, Cover and Table of Contents.
Ling et al., "Lysine methyltransferase G9a methylates the transcription factor MyoD and regulates skeletal muscle differentiation" PNAS (2012) 109(3):841-846.
Liu et al., "Discovery of an in Vivo Chemical Probe of the Lysine Methyltransferases G9a and GLP," J. Med Chem. (2013) 56(21):8931-8942.
March, J., Advanced Organic Chemistry (1992) 4th Ed., John Wiley and Sons, New York, New York, Cover and Table of Contents.
Merkling et al., "The Epigenetic Regulator G9a Mediates Tolerance to RNA Virus Infection in *Drosophila*" PLoS Pathog. (2015) 11(4). e1004692.
Paquette et al., Organic Reactions (1992) vol. 1-40, John Wiley and Sons, Cover and Table of Contents.
Renneville et al., "EHMT1 and EHMT2 inhibition induces fetal hemoglobin expression," Blood (2015) 126(16):1930-1939.
Sainsbury et al., Rodd's Chemistry of Carbon Compounds vols. 1-5 and Supplementals (1989) 2nd Ed., Elsevier Science & Technology, Oxford, United Kingdom, Cover and Table of Contents.
Sankaran et al., "The Switch from Fetal to Adult Hemoglobin" Cold Spring Harb Perspect Med. (2013) 3(1): a011643.
Shankar et al., "G9a, a multipotent regulator of gene expression" Epigenetics (2013) 8(1):16-22.
Shinkai et al., "H3K9 methyltransferase G9a and the related molecule GLP" Genes & Dev. (2011) 25(8):781-788.
Srimongkolpithak et al., "Identification of 2,4-diamino-6,7-diamethoxyquinoline derivatives as G9a inhibitors" Med. Chem. Comm. (2014) 5(12):1821-1828.
Sweis et al., "Discovery and Development of Potent and Selective Inhibitors of Histone Methyltransferase G9a" ACS Med Chem Lett. (2014);5(2):205-209.
Tseng et al., "Synthesis and antiproliferative evaluation of 2,3-diarylquinoline derivatives" Organic and Biomolecular Chemistry (2011) 9(9):3205-3216.
Wang et al., "Histone H3K9 methyltransferase G9a represses PPARγ expression and adipogenesis" EMBO J. (2013) 32(1):45-59.
You et al., "Cancer Genetics and Epigenetics: Two Sides of the Same Coin?," Cancer Cell (2012) 22(1):9-20.
International Search Report and Written Opinion dated Apr. 10, 2017 for PCT Application No. PCT/US2017/017977, filed Feb. 15, 2017.
STN-Chemical Database Registry Nos. 7470-07-07, 5442-99-9, 5438-96-0, 5438-91-5, Entered STN: Nov. 16, 1984; [Date of Search: Dec. 2, 2020].
Office Action for Japan Patent Application No. 2018-543226, dated Jan. 12, 2021.

\* cited by examiner

HISTONE METHYLTRANSFERASE INHIBITORS

CROSS-REFERENCES TO RELATED APPLICATIONS

This application claims the benefit of U.S. Provisional Application No. 62/296,484, filed Feb. 17, 2016, and U.S. Provisional Application No. 62/351,208, filed Jun. 16, 2016, which are incorporated herein by reference in their entirety for all purposes.

FIELD OF THE DISCLOSURE

The present disclosure provides certain compounds that are histone methyltransferases G9a and/or GLP inhibitors and are therefore useful for the treatment of diseases treatable by inhibition of G9a and/or GLP such as cancers and hemoglobinpathies (e.g., beta-thalassemia and sickle cell disease). Also provided are pharmaceutical compositions containing such compounds as well as processes and intermediates for preparing such compounds.

BACKGROUND

Chromatin modification plays an essential role in transcriptional regulation. These modifications, including DNA methylation, histone acetylation and histone methylation, are important in a variety of biological processes including protein production and cellular differentiation, and are emerging as attractive drug targets in various human diseases. Two particular enzymes associated with histone methylation are G9a and GLP, also known as EHMT2 and EHMT1 (Euchromatic histone-lysine N-methyltransferase 2 and 1). G9a and GLP are the primary enzymes for mono- and dimethylation at Lys 9 of histone H3 (H3K9me1 and H3K9me2), and exist predominantly as a G9a-GLP heteromeric complex that appears to be a functional H3K9 methyltransferase in vivo. Structurally, either G9a or GLP is composed of a catalytic SET domain, a domain containing ankyrin repeats (involved in protein-protein interactions) and nuclear localization signals on the N-terminal region. The SET domain is responsible for the addition of methyl groups on H3, whereas the ankyrin repeats have been observed to represent mono- and dimethyl lysine binding regions. G9a-GLP complex is thus not only able to both methylate histone tails but also able to recognize this modification, functioning as a scaffold for the recruitment of other target molecules on the chromatin [see Genes Dev. 2011 Apr. 15; 25(8):781-8. doi: 10.1101/gad.2027411. H3K9 methyltransferase G9a and the related molecule GLP; Epigenetics. 2013 January; 8(1):16-22. doi: 10.4161/epi.23331. G9a, a multipotent regulator of gene expression].

Many important studies have reported that G9a and GLP play critical roles in various biological processes. Several reports have highlighted its link to a variety of cancers [see Front Immunol. 2015 Sep. 25; 6:487. doi: 10.3389/fimmu.2015.00487. Functional Role of G9a Histone Methyltransferase in Cancer]. It is upregulated in hepatocellular carcinoma, B cell acute lymphoblastic leukemia, and lung cancers. In addition, elevated expression of G9a in aggressive lung cancer correlates with poor prognosis, while its knockdown in highly invasive lung cancer cells suppressed metastasis in an in vivo mouse model. In prostate cancer cells (PC3), G9a knockdown caused significant morphological changes and inhibition of cell growth. [see J. Med Chem. 2013 Nov. 14; 56(21):8931-42. doi: 10.1021/jm401480r. Epub 2013 Oct. 31. Discovery of an in vivo chemical probe of the lysine methyltransferases G9a and GLP; ACS Med Chem Lett. 2014 Jan. 2; 5(2):205-9. doi: 10.1021/ml400496h. eCollection 2014. Discovery and development of potent and selective inhibitors of histone methyltransferase g9a.]

Interestingly, recent studies have also shown that the inhibition of G9a and GLP by either genetic depletion or pharmacological intervention increased fetal hemoglobin (HbF) gene expression in erythroid cells [see Blood. 2015 Jul. 30; 126(5):665-72. Inhibition of G9a methyltransferase stimulates fetal hemoglobin production by facilitating LCR/γ-globin looping; Blood. 2015 Oct. 15; 126(16):1930-9. EHMT1 and EHMT2 inhibition induces fetal hemoglobin expression]. Inducing fetal globin gene would be potentially therapeutically beneficial for the disease of hemoglobinpathies, including beta-thalassemia and sickle cell disease where the production of normal β-globin, a component of adult hemoglobin, is impaired. [see Cold Spring Harb Perspect Med. 2013 January; 3(1): a011643. doi: 10.1101/cshperspect.a011643 Switch from Fetal to Adult Hemoglobin]. Moreover, G9a or GLP inhibitions may potentiate other clinically used therapies, such as hydroxyurea or HDAC inhibitors. These agents may act, at least in part, by increasing γ-globin gene expression through different mechanisms [see Blood. 1992 May 15; 79(10):2555-65. Hydroxyurea: effects on hemoglobin F production in patients with sickle cell anemia]. Thus, there is a need for the development of small molecules that are capable of inhibiting the activity of G9a and/or GLP. The compounds of the present disclosure fulfill this and related needs.

SUMMARY

In one aspect, provided is a compound of Formula (I):

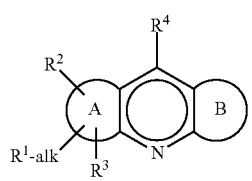

where:

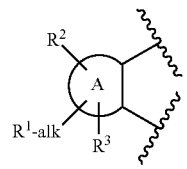

is a ring of formula (i), (ii), (iii), or (iv):

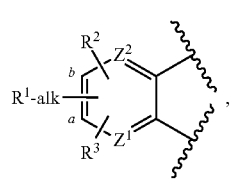

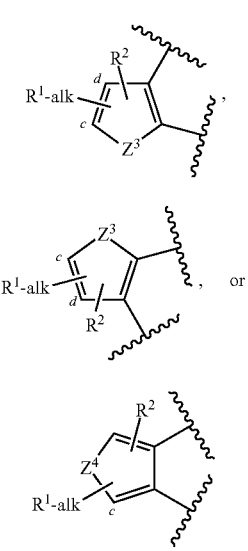

wherein:
Z$^1$ and Z$^2$ are independently C (when R$^2$ or R$^3$ is attached thereto), CH, or N;
Z$^3$ is NH, N-alkyl, O, or S;
Z$^4$ is N (when -alk-R$^1$ is attached thereto), NH, N-alkyl, O, or S;
alk is alkylene wherein one or two carbon atoms of the alkylene chain are optionally replaced by NR, O, S, or SO$_2$ (where R is hydrogen or alkyl) and the alkylene chain is optionally substituted with one or two substituents independently selected from halo, haloalkyl, haloalkoxy, hydroxyl, and alkoxy; and wherein -alk-R$^1$ is attached to carbon (a) or (b) of ring (i), carbon (c) or (d) of rings (ii) or (iii), or Z$^4$ or carbon (c) of ring (iv);
R$^1$ is —NR$^6$R$^7$ (where R$^6$ and R$^7$ are independently hydrogen, alkyl, hydroxyalkyl, alkoxyalkyl, haloalkyl, or haloalkoxyalkyl), heterocyclyl (optionally substituted with R$^a$, R$^b$, or R$^c$ independently selected from alkyl, hydroxyl, alkoxy, halo, haloalkyl, alkylcarbonyl, and haloalkylcarbonyl), and spiroheterocycloamino wherein a nitrogen atom of spiroheterocycloamino is attached to alk;
R$^2$ is hydrogen, alkyl, cycloalkyl, halo, hydroxyl, alkoxy, haloalkoxy, or cyano;
R$^3$ is hydrogen, alkyl, halo, alkoxy, or cyano or R$^3$ is absent in rings of formula (ii), (iii) and (iv);
R$^4$ is hydrogen, alkyl (optionally substituted with one, two, or three deuterium), —OR$^d$ (where R$^d$ is hydrogen, alkyl, haloalkyl, hydroxyalkyl, alkoxyalkyl, cycloalkyl, halocycloalkyl, cycloalkylalkyl, aryl, aralkyl, heteroaryl, heteroaralkyl, heterocyclyl, or heterocyclylalkyl), or NR$^e$R$^f$ (where R$^e$ is hydrogen or alkyl and R$^f$ is hydrogen, alkyl, aminoalkyl, cyanoalkyl, carboxyalkyl, alkoxycarbonylalkyl, haloalkyl, hydroxyalkyl, alkoxyalkyl, cycloalkyl, cycloalkylalkyl, dicycloalkylalkyl, aryl, aralkyl, heteroaryl, heteroaralkyl, heterocyclyl, bridged heterocyclyl, heterocyclylalkyl, alkylsulfonyl, cycloalkylsulfonyl, cycloalkylalkylsulfonyl, arylsulfonyl, aralkylsulfonyl, heteroarylsulfonyl, heteroaralkylsulfonyl, heterocyclylsulfonyl, or heterocyclylalkylsulfonyl) wherein cycloalkyl, aryl, heteroaryl, and heterocyclyl either alone or in cycloalkylalkyl, aralkyl, heteroaralkyl or heterocyclylalkyl in R$^d$ are optionally substituted with R$^g$, R$^h$, or R$^i$ independently selected from alkyl, hydroxyl, alkoxy, halo, haloalkyl, and haloalkoxy, and wherein cycloalkyl, aryl, heteroaryl, and heterocyclyl either alone or in cycloalkylalkyl, aralkyl, heteroaralkyl, heterocyclylalkyl, cycloalkylsulfonyl, heteroaralkylsulfonyl, or heterocyclylalkylsulfonyl in R$^f$ are optionally substituted with R$^g$, R$^h$, or R$^i$ independently selected from alkyl, cycloalkyl, hydroxyl, alkoxy, alkoxycarbonyl, halo, haloalkyl, and haloalkoxy and further wherein alkylene in aralkyl, heteroaralkyl, heterocyclylalkyl, and cycloalkylalkyl is optionally substituted with one, two, or three deuterium;
ring B is phenyl, 5- or 6-membered heteroaryl containing one or two heteroatoms independently selected from nitrogen, oxygen and sulfur, 5- or 6- or 7-membered cycloalkyl, or 5- or 6- or 7-membered saturated heterocyclyl, each optionally substituted with R$^j$, R$^k$, or R$^l$ independently selected from alkyl, hydroxyl, alkoxy, halo, haloalkyl, and haloalkoxy; or a pharmaceutically acceptable salt thereof.

In a second aspect, this disclosure is directed to a pharmaceutical composition comprising a compound of Formula (I) (or any of the embodiments thereof described herein), and/or a pharmaceutically acceptable salt thereof; and a pharmaceutically acceptable excipient.

In a third aspect, this disclosure is directed to a method of treating a disease treatable by inhibition of G9a and/or GLP in a patient in recognized need of such treatment which method comprises administering to the patient in recognized need thereof, a pharmaceutical composition comprising a compound of (I) (or any of the embodiments thereof described herein) and/or a pharmaceutically acceptable salt thereof in a therapeutically effective amount, and a pharmaceutically acceptable excipient. In one embodiment the disease is hemoglobinpathies such as beta-thalassemia and sickle cell disease (see Blood. 2015 Jul. 30; 126(5):665-72. Inhibition of G9a methyltransferase stimulates fetal hemoglobin production by facilitating LCR/γ-globin looping; and Blood. 2015 Oct. 15; 126(16):1930-9. EHMT1 and EHMT2 inhibition induces fetal hemoglobin expression), cancer or tumor (see Front Immunol. 2015 Sep. 25; 6:487. doi: 10.3389/fimmu. 2015.00487. Functional Role of G9a Histone Methyltransferase in Cancer); cancer predisposition genetic syndromes such as Cowden disease (see Cancer Cell. 2012 Jul. 10; 22(1):9-20. doi: 10.1016/j.ccr.2012.06.008. Cancer genetics and epigenetics: two sides of the same coin?), inflammation and autoimmune diseases, such as treating intestinal inflammation (see J Clin Invest. 2014 May; 124(5):1945-55. doi: 10.1172/JCI69592. Methyltransferase G9A regulates T cell differentiation during murine intestinal inflammation), metabolic diseases such as diabetes and obesity (see EMBO J. 2013 Jan. 9; 32(1): 45-59. doi:10.1038/emboj.2012.306. Epub 2012 Nov. 23. Histone H3K9 methyltransferase G9a represses PPARγ expression and adipogenesis), diseases related with skeletal muscle development and regenerative (see Proc Natl Acad Sci USA. 2012 Jan. 17; 109(3):841-6. doi: 10.1073/pnas.1111628109. Epub 2012 Jan. 3. Lysine methyltransferase G9a methylates the transcription factor MyoD and regulates skeletal muscle differentiation) and viral diseases such as HIV-1 (human immunodeficiency virus 1) and HBV (Hepatitis B Virus) (see J Biol Chem. 2010 May 28; 285 (22):16538-45. doi: 10.1074/jbc.M110.103531. Involvement of histone H3 lysine 9 (H3K9) methyltransferase G9a in the maintenance of HIV-1 latency and its reactivation by BIX01294; and PLoS Pathog. 2015 Apr. 16; 11(4): e1004692. doi: 10.1371/journal.ppat. 1004692. The epigenetic regulator G9a mediates tolerance to RNA virus infection in *Drosophila*).

In a fourth aspect provided is a compound of Formula (I) and/or a pharmaceutically acceptable salt thereof for use in the treatment of diseases provided in the third aspect above.

In a fifth aspect provided is an intermediate of Formula (II), or a salt thereof,

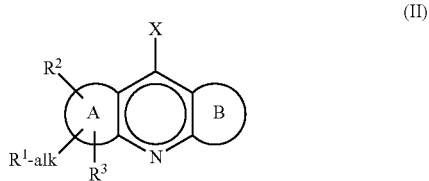

wherein X is a leaving group under nucleophilic substitution reaction conditions; and the remaining variables are as defined herein for Formula (I). In one embodiment of this aspect, X is halo (e.g., chloro) tosylate, mesylate or triflate.

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Aminoalkyl" means alkyl as defined above which is substituted with one or two amino (—NH$_2$) groups, e.g., aminomethyl, aminoethyl, 1,3-diaminopropyl, and the like.

"Aminocarbonyl" means a —CONH$_2$ radical.

"Alkylaminocarbonyl" means a —CONHR radical where R is alkyl as defined above, e.g., methylaminocarbonyl, ethylaminocarbonyl, propylaminocarbonyl, or 2-propylaminocarbonyl, and the like.

"Dialkylaminocarbonyl" means a —CONRR' radical where R and R' are alkyl as defined above, e.g., dimethylaminocarbonyl, diethylaminocarbonyl, methylpropylaminocarbonyl, or diisopropylaminocarbonyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means alkyl as defined above which is substituted with one or two alkoxy groups as defined above, e.g., methoxyethyl, ethoxyethyl, methoxypropyl, and the like.

"Alkylcarbonyl" means a —COR radical where R is alkyl as defined above, e.g., methylcarbonyl, ethylcarbonyl, and the like.

"Alkoxycarbonyl" means a —COOR radical where R is alkyl as defined above, e.g., methoxycarbonyl, ethoxycarbonyl, and the like.

"Alkoxycarbonylalkyl" means a -(alkylene)-COOR radical where R is alkyl as defined above, e.g., methoxycarbonylethyl, ethoxycarbonylmethyl, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above, e.g., benzyl, phenethyl, and the like.

"Alkylsulfonyl" means a —SO$_2$R radical where R is alkyl as defined above, e.g., methylsulfonyl, ethylsulfonyl and the like.

"Arylsulfonyl" means a —SO$_2$R radical where R is aryl as defined above, e.g., phenylsulfonyl, and the like.

"Aralkylsulfonyl" means a —SO$_2$R radical where R is aralkyl as defined above, e.g., benzylsulfonyl, and the like.

"Carboxyalkyl" means alkyl as defined above which is substituted with one or two carboxy (—COOH) groups, e.g., carboxymethyl, carboxyethyl, 1,3-dicarboxypropyl, and the like.

"Cyanoalkyl" means alkyl as defined above which is substituted with one or two cyano (—C≡N) groups, e.g., cyanomethyl, cyanoethyl, 1,3-dicyanopropyl, and the like.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylalkyl" means a -(alkylene)-R radical where R is cycloalkyl as defined above, e.g., cyclopropylmethyl, cyclohexylmethyl, and the like.

"Dicycloalkylalkyl" means cycloalkylalkyl as defined above wherein the alkylene is substituted with another cycloalkyl group as defined above.

"Cycloalkylsulfonyl" means a —SO$_2$R radical where R is cycloalkyl as defined above, e.g., cyclopropylsulfonyl, cyclobutylsulfonyl and the like.

"Cycloalkylalkylsulfonyl" means a —SO$_2$R radical where R is cycloalkylalkyl as defined above, e.g., cyclopropylmethylsulfonyl, cyclobutylethylsulfonyl and the like.

"Halo" means fluoro, chloro, bromo, or iodo, preferably fluoro or chloro.

"Haloalkyl" means an alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, the haloalkoxy may be referred to in this Application as fluoroalkoxy.

"Haloalkoxyalkyl" means alkyl as defined above which is substituted with one or two haloalkoxy groups as defined above, e.g., trifluormethoxyethyl, 3,3,3-trifluoroethoxyethyl, and the like.

"Haloalkylcarbonyl" means a —COR radical where R is haloalkyl as defined above, e.g., trifluoromethylcarbonyl, pentafluoroethylcarbonyl, and the like.

"Hydroxyalkyl" means alkyl as defined above which is substituted with one or two hydroxy (—OH) groups, e.g., hydroxymethyl, hydroxyethyl, 1,3-dihydroxypropyl, and the like.

"Halocycloalkyl" means a cycloalkyl group as defined above which is substituted with one, two or three halogen as defined above, e.g., 2,2-difluorocyclopropyl, and the like.

"Heterocyclyl" means a saturated or unsaturated monovalent monocyclic group of 4 to 8 ring atoms in which one or two ring atoms are heteroatom selected from N, O, and $S(O)_n$, where n is an integer from 0 to 2, the remaining ring atoms being C, unless stated otherwise. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom (e.g., pyrrolidine, piperidine, piperazine, oxazolidine), it is also referred to herein as heterocycloamino and is a subset of the heterocyclyl group. When the heterocyclcyl ring has no double bond, it is referred to herein as saturated heterocyclyl. "Bridged heterocyclyl" means a heterocyclyl as defined above which further includes an alkylene bridge connecting two ring atoms of the heterocyclyl ring, e.g., 8-oxabicyclo[3.2.1]octan-3-yl, and the like.

"Heterocyclylalkyl" or "heterocycloalkyl" means a -(alkylene)-R radical where R is heterocyclyl ring as defined above e.g., tetraydrofuranylmethyl, piperazinylmethyl, morpholinylethyl, and the like.

"Heterocyclylsulfonyl" means a —SO$_2$R radical where R is heterocyclyl as defined above, e.g., piperidinylsulfonyl, and the like.

"Heterocyclylalkylsulfonyl" means a —SO$_2$R radical where R is heterocyclylalkyl as defined above, e.g., piperidinylmethylsulfonyl, and the like.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. When the heteroaryl ring contains 5- or 6 ring atoms it is also referred to herein as 5- or 6-membered heteroaryl.

"Heteroaralkyl" means a -(alkylene)-R radical where R is heteroaryl as defined above, e.g., pyridinylmethyl, and the like. When the heteroaryl ring in heteroaralkyl contains 5- or 6 ring atoms it is also referred to herein as 5- or 6-membered heteroaralkyl.

"Heteroarylsulfonyl" means a —SO$_2$R radical where R is heteroaryl as defined above, e.g., pyridinylsulfonyl, and the like.

"Heteroaralkylsulfonyl" means a —SO$_2$R radical where R is heteroaralkyl as defined above, e.g., pyridinylmethylsulfonyl, and the like.

"Oxo" means a =O radical. As would be readily apparent to one of skill in the art, "carbonyl" refers to an oxo radical attached to a carbon atom, i.e., —C(O)—.

"Spiroheterocycloamino" means a saturated bicyclic ring having 6 to 10 ring atoms in which one, two, or three ring atoms are heteroatom selected from N, N-oxide, O, and $S(O)_n$, where n is an integer from 0 to 2, the remaining ring atoms being C, provided that at least one ring atom is N, and the rings are connected through only one atom. The connecting atom is also called the spiroatom, and is most often a quaternary carbon ("spiro carbon"). Representative examples include, but are not limited to, 2,6-diazaspiro[3.3]heptane, 2,6-diazaspiro[3.4]octane, 2-azaspiro[3.4]octane, 2-azaspiro[3.5]nonane, 2,7-diazaspiro[4.4]nonane, and the like.

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

The present disclosure also includes polymorphic forms and deuterated forms of the compound of the present disclosure and/or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity i.e., the (S) stereoisomer in less than about 5%, preferably 2% by wt and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of the present disclosure are within the scope of this disclosure.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure and/or a pharmaceutically acceptable salt thereof that, when administered to a patient for treating a disease, is sufficient to effect such treatment for the disease. The "therapeutically effective amount" will vary depending on the compound, the disease and its severity and the age, weight, etc., of the mammal to be treated.

EMBODIMENTS

In further embodiments 1-13 below, the present disclosure includes:

1. A compound of Formula (I) or a pharmaceutically acceptable salt thereof as defined in the Summary. Within embodiment 1 in one group of compounds

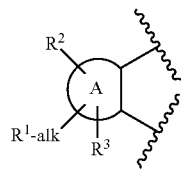

is a ring of formula (i), (ii), (iii), or (iv):

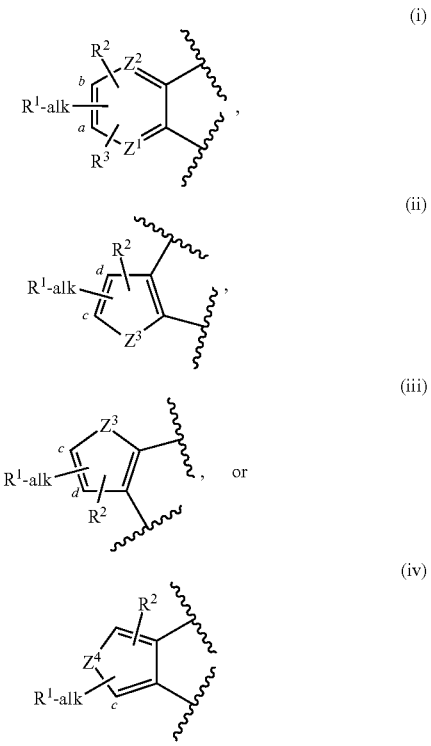

wherein:
  $Z^1$ and $Z^2$ are independently C (when $R^2$ or $R^3$ is attached thereto), CH, or N;
  $Z^3$ is NH, N-alkyl, O, or S;
  $Z^4$ is N (when -alk-$R^1$ is attached thereto), NH, N-alkyl, O, or S;
  alk is alkylene wherein one or two carbon atoms of the alkylene chain are optionally replaced by NR, O, S, or $SO_2$ (where R is hydrogen or alkyl) and the alkylene chain is optionally substituted with one or two substituents independently selected from halo, haloalkyl, haloalkoxy, hydroxyl, and alkoxy; and wherein -alk-$R^1$ is attached to carbon (a) or (b) of ring (i), carbon (c) or (d) of rings (ii) or (iii), or $Z^4$ or carbon (c) of ring (iv);
  $R^1$ is —$NR^6R^7$ (where $R^6$ and $R^7$ are independently hydrogen, alkyl, hydroxyalkyl, alkoxyalkyl, haloalkyl, or haloalkoxyalkyl), heterocyclyl (optionally substituted with $R^a$, $R^b$, or $R^c$ independently selected from alkyl, hydroxyl, alkoxy, halo, haloalkyl, alkylcarbonyl, and haloalkylcarbonyl), and spiroheterocycloamino wherein a nitrogen atom of spiroheterocycloamino is attached to alk;
  $R^2$ is hydrogen, alkyl, cycloalkyl, halo, hydroxyl, alkoxy, haloalkoxy, or cyano;
  $R^3$ is hydrogen, alkyl, halo, alkoxy, or cyano or $R^3$ is absent in rings of formula (ii), (iii) and (iv);
  $R^4$ is hydrogen, alkyl (optionally substituted with one, two, or three deuterium), —$OR^d$ (where $R^d$ is hydrogen, alkyl, haloalkyl, hydroxyalkyl, alkoxyalkyl, cycloalkyl, halocycloalkyl, cycloalkylalkyl, aryl, aralkyl, heteroaryl, heteroaralkyl, heterocyclyl, or heterocyclylalkyl), or $NR^eR^f$ (where $R^e$ is hydrogen or alkyl and $R^f$ is hydrogen, alkyl, haloalkyl, hydroxyalkyl, alkoxyalkyl, cycloalkyl, cycloalkylalkyl, aryl, aralkyl, heteroaryl, heteroaralkyl, heterocyclyl, heterocyclylalkyl, alkylsulfonyl, cycloalkylsulfonyl, cycloalkylalkylsulfonyl, arylsulfonyl, aralkylsulfonyl, heteroarylsulfonyl, heteroaralkylsulfonyl, heterocyclylsulfonyl, or heterocyclylalkylsulfonyl) wherein cycloalkyl, aryl, heteroaryl, and heterocyclyl either alone or in cycloalkylalkyl, aralkyl, heteroaralkyl or heterocyclylalkyl in $R^d$ are optionally substituted with $R^g$, $R^h$, or $R^i$ independently selected from alkyl, hydroxyl, alkoxy, halo, haloalkyl, and haloalkoxy, and wherein cycloalkyl, aryl, heteroaryl, and heterocyclyl either alone or in cycloalkylalkyl, aralkyl, heteroaralkyl, heterocyclylalkyl, cycloalkylsulfonyl, heteroaralkylsulfonyl, or heterocyclylalkylsulfonyl in $R^f$ are optionally substituted with $R^g$, $R^h$, or $R^i$ independently selected from alkyl, hydroxyl, alkoxy, halo, haloalkyl, and haloalkoxy and further wherein alkylene in aralkyl, heteroaralkyl, heterocyclylalkyl, and cycloalkylalkyl is optionally substituted with one, two, or three deuterium;

ring B is phenyl, 5- or 6-membered heteroaryl containing one or two heteroatoms independently selected from nitrogen, oxygen and sulfur, 5- or 6-membered cycloalkyl, or 5- or 6-membered saturated heterocyclyl, each optionally substituted with $R^j$, $R^k$, or $R^l$ independently selected from alkyl, hydroxyl, alkoxy, halo, haloalkyl, and haloalkoxy.

2. The compound of embodiment 1 or a pharmaceutically acceptable salt thereof and group contained therein wherein $R^4$ is hydrogen, alkyl, —$OR^d$ (where $R^d$ is hydrogen, alkyl, haloalkyl, hydroxyalkyl, alkoxyalkyl, cycloalkyl, halocycloalkyl, cycloalkylalkyl, aryl, aralkyl, heteroaryl, heteroaralkyl, heterocyclyl, or heterocyclylalkyl), or $NR^eR^f$ (where $R^e$ is hydrogen or alkyl and $R^f$ is hydrogen, alkyl, aminoalkyl, cyanoalkyl, carboxyalkyl, alkoxycarbonylalkyl, cycloalkyl, halocycloalkyl, cycloalkylalkyl, dicycloalkylalkyl, aryl, aralkyl, heteroaryl, heteroaralkyl, heterocyclyl, bridged heterocyclyl, or heterocyclylalkyl) wherein aryl, heteroaryl, and heterocyclyl either alone or in aralkyl, heteroaralkyl, or heterocyclylalkyl in $R^d$ are optionally substituted with $R^g$, $R^h$, or $R^i$ independently selected from alkyl, hydroxyl, alkoxy, halo, haloalkyl, and haloalkoxy, and wherein aryl, heteroaryl, and heterocyclyl either alone or in aralkyl, heteroaralkyl, or heterocyclylalkyl in $R^f$ are optionally substituted with $R^g$, $R^h$, or $R^i$ independently selected from alkyl, cycloalkyl, hydroxyl, alkoxy, alkoxycarbonyl, halo, haloalkyl, and haloalkoxy. Within embodiment 2 in one group of compounds $R^4$ is hydrogen, alkyl, —$OR^d$ (where $R^d$ is hydrogen, alkyl, haloalkyl, hydroxyalkyl, alkoxyalkyl, cycloalkyl, halocycloalkyl, cycloalkylalkyl, aryl, aralkyl, heteroaryl, heteroaralkyl, heterocyclyl, or heterocyclylalkyl), or $NR^eR^f$ (where $R^e$ is hydrogen or alkyl and $R^f$ is hydrogen, alkyl, cycloalkyl, halocycloalkyl, cycloalkylalkyl, aryl, aralkyl, heteroaryl, heteroaralkyl, heterocyclyl, or heterocyclylalkyl) wherein aryl, heteroaryl, and heterocyclyl either alone or in aralkyl, heteroaralkyl, or heterocyclylalkyl in $R^d$ and $R^f$ are optionally substituted with $R^g$, $R^h$, or $R^i$ independently selected from alkyl, hydroxyl, alkoxy, halo, haloalkyl, and haloalkoxy.

3. The compound of embodiment 1 or 2 or a pharmaceutically acceptable salt thereof and group contained therein wherein ring B is phenyl optionally substituted with $R^j$, $R^k$, or $R^l$ independently selected from alkyl, hydroxyl, alkoxy, halo, haloalkyl, and haloalkoxy. Within embodiment 3, in one group of compounds phenyl is optionally substituted with $R^j$, $R^k$, or $R^l$ independently selected from methyl, ethyl, fluoro, chloro, methoxy, trifluoromethyl, and trifluoromethoxy. Within embodiment 3, in another group of compounds, ring B is phenyl optionally substituted with methyl, methoxy or fluoro. Within embodiment 3, in another group of compounds ring B is phenyl.

4. The compound of embodiment 1 or 2 or a pharmaceutically acceptable salt thereof and group contained therein wherein ring B is 5- or 6- or 7-membered cycloalkyl optionally substituted with $R^j$, $R^k$, or $R^l$ independently selected from alkyl, hydroxyl, alkoxy, halo, haloalkyl, and haloalkoxy. Within embodiment 4, in one group of compounds, ring B is 5- or 6-membered cycloalkyl optionally substituted with $R^j$, $R^k$, or $R^l$ independently selected from alkyl, hydroxyl, alkoxy, halo, haloalkyl, and haloalkoxy. Within embodiment 4, in another group of compounds, ring B is cyclopentyl or cyclohexyl, each optionally substituted with fluoro, chloro, or methyl. Within embodiment 4, in another group of compounds, ring B is cyclopentyl or cyclohexyl, each optionally substituted with methyl. Within embodiment 4, in another group of compounds, ring B is cyclopentyl or cyclohexyl.

5. The compound of embodiment 1 or 2 or a pharmaceutically acceptable salt thereof and group contained therein wherein ring B is 5- or 6- or 7-membered heterocyclyl or pyridyl, each ring optionally substituted with $R^j$, $R^k$, or $R^l$ independently selected from alkyl, hydroxyl, alkoxy, halo, haloalkyl, and haloalkoxy. Within embodiment 5, in one group of compounds, ring B is 5- or 6-membered heterocyclyl or pyridyl, each ring optionally substituted with $R^j$, $R^k$, or $R^l$ independently selected from alkyl, hydroxyl, alkoxy, halo, haloalkyl, and haloalkoxy. Within embodiment 5, in another group of compounds, ring B is piperidinyl or tetrahydropyranyl, each optionally substituted with methyl. Within embodiment 5, in another group of compounds ring B is pyridyl.

6. The compound of any one of embodiments 1 to 5 and groups contained therein or a pharmaceutically acceptable salt thereof wherein:

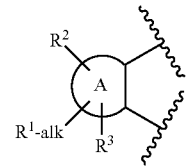

is a ring of formula (i'):

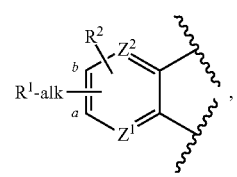

(i')

Within embodiment 6, in one group of compounds, $Z^1$ and $Z^2$ are N. Within embodiment 6, in another group of compounds, $Z^1$ or $Z^2$ is N. Within embodiment 6, in yet another group of compounds, $Z^1$ and $Z^2$ are C or CH. Within embodiment 6, in yet another group of compounds, -alk-$R^1$ is attached to carbon (a) of ring (i'). Within embodiment 6, in yet another group of compounds -alk-$R^1$ is attached to carbon (a) and $R^2$ is attached to carbon (b) of ring (i'). Within embodiment 6, in yet another group of compounds -alk-R¹ is attached to carbon (a) and R² is attached to carbon (b) of ring (i') and Z¹ and Z² are CH.

7. The compound of any one of embodiments 1 to 5 and groups contained therein or a pharmaceutically acceptable salt thereof wherein:

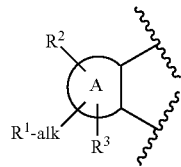

is a ring of formula (ii), (iii), or (iv). Within embodiment 7, in one group of compounds

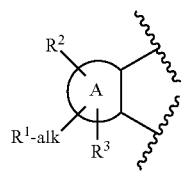

is a ring (ii) or (iv') shown below.

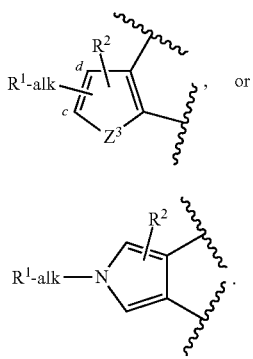

Within embodiment 7, in another group of compounds, ring A is of formula (ii). Within embodiment 7, in another group of compounds, ring A is of formula (iv').

Within groups of compounds where ring A is of formula (ii), in one group of compounds, Z³ is O. Within group of compounds where ring A is of formula (ii), in another group of compounds, Z³ is S. Within group of compounds where ring A is of formula (ii), in yet another group of compounds, Z³ is NH or N-alkyl. Within group of compounds where ring A is of formula (ii), and groups contained therein, in one group of compounds, -alk-R¹ is attached to carbon (c) of the ring.

8. The compound of any one of embodiments 1 to 7 and groups contained therein or a pharmaceutically acceptable salt thereof wherein alk in -(alk)-R¹ is —(CH$_2$)$_2$—, —(CH$_2$)$_3$—, (CH$_2$)$_4$—, —CH$_2$CH(CH$_3$)CH$_2$—, —O—(CH$_2$)—, —O—(CH$_2$)$_2$—, or —O—(CH$_2$)$_3$—, preferably is —(CH$_2$)$_2$—, —(CH$_2$)$_3$—, (CH$_2$)$_4$—, —CH$_2$CH(CH$_3$)CH$_2$—, —O—(CH$_2$)$_2$—, or —O—(CH$_2$)$_3$—. Within embodiment 8, in one group of compounds alk in -(alk)-R¹ is —O—(CH$_2$)—, —O—(CH$_2$)$_2$—, or —O—(CH$_2$)$_3$—.

Within embodiment 8, in one group of compounds R¹ is —NR⁶R⁷ where —NR⁶R⁷ is amino, methylamino, ethylamino, dimethylamino, or diethylamino. Within embodiment 8, in another group of compounds R¹ is heterocyclyl optionally substituted with R$^a$, R$^b$, or R$^c$ independently selected from alkyl, hydroxyl, alkoxy, and halo, preferably R¹ is azetidin-1-yl, pyrrolidin-1-yl, piperidin-1-yl, morpholin-4-yl, thiomorpholin-4-yl, or tetrahydrofuranyl, each optionally substituted with R$^a$ or R$^b$ independently selected from methyl, hydroxyl, methoxy, and fluoro. Within embodiment 8, in another group of compounds -alk-R¹ is —O—(CH$_2$)$_3$-pyrrolidin-1-yl or —O—(CH$_2$)$_3$-piperidin-1-yl, or —O—(CH$_2$)$_3$-morpholin-4-yl, each optionally substituted with R$^a$ or R$^b$ independently selected from methyl, hydroxyl, methoxy, and fluoro. Within embodiment 8, in yet another group of compounds -alk-R¹ is —O—(CH$_2$)$_3$—R¹ where R¹ is pyrrolidin-1-yl, 3-hydroxy-3-methylpyrrolidin-1-yl, 3-hydroxy-3-methylazetidin-1-yl, 3-fluoroazetidinyl, 3-fluoropyrrolidinyl, 3(R)-fluoropyrrolidinyl, or 3(S)-fluoropyrrolidinyl. Within embodiment 8, in yet another group of compounds -alk-R¹ is —O—(CH$_2$)$_3$—R¹ where R¹ is pyrrolidin-1-yl. Within embodiment 8, in yet another group of compounds -alk-R¹ is —O—(CH$_2$)—R¹ where R¹ is 1-methylpyrrolidin-3-yl or 1-methylpiperididn-3-yl.

9. The compound of any one of embodiments 1 to 8 and groups contained therein or a pharmaceutically acceptable salt thereof wherein R² is alkyl, halo, hydroxyl, or alkoxy. Within embodiment 9, in another group of compounds R² is alkyl, halo or alkoxy. Within embodiment 9, in one group of compounds R² is alkoxy, preferably methoxy or ethoxy. Within embodiment 9, in one group of compounds R² is halo, preferably chloro or fluoro. Within embodiment 9, in one group of compounds R² is alkyl, preferably methyl or ethyl.

10. The compound of any one of embodiments 1 to 9 and groups contained therein or a pharmaceutically acceptable salt thereof wherein R⁴ is hydrogen.

11. The compound of any one of embodiments 1 to 9 and groups contained therein or a pharmaceutically acceptable salt thereof wherein R⁴ is alkyl, preferably methyl.

12. The compound of any one of embodiments 1 to 9 and groups contained therein or a pharmaceutically acceptable salt thereof wherein R⁴ is —OR$^d$ (where R$^d$ is alkyl, cycloalkyl, cycloalkylalkyl, aryl, aralkyl, heteroaryl, heteroaralkyl, heterocyclyl, or heterocyclylalkyl) wherein cycloalkyl, aryl, heteroaryl, and heterocyclyl either alone or in cycloalkylalkyl, aralkyl, heteroaralkyl, or heterocyclylalkyl in R$^d$ is optionally substituted with R$^g$, R$^h$, or R$^i$ independently selected from alkyl, hydroxyl, alkoxy, halo, haloalkyl, and haloalkoxy. Within this embodiment 12, in one group of compounds R⁴ is —O-alkyl, preferably R⁴ is methoxy, ethoxy, or n-, or isopropoxy. Within this embodiment 12, in one group of compounds R⁴ is —O-cycloalkyl, preferably R⁴ is cyclopropoxy, cyclopentoxy, or cyclohexyloxy. Within this embodiment 12, in one group of compounds R⁴ is —O— heterocyclyl optionally substituted with R$^g$, R$^h$, or R$^i$ independently selected from alkyl, hydroxyl, alkoxy, halo, haloalkyl, and haloalkoxy, preferably R⁴ is piperidin-4-yloxy, tetrahydropyran-4-yloxy, tetrahydrofuran-3-yloxy, or 1-alkylpiperidin-4-yloxy.

13. The compound of any one of embodiments 1 to 9 and groups contained therein or a pharmaceutically acceptable salt thereof wherein R⁴ is NR$^e$R$^f$ (where R$^e$ is hydrogen or alkyl and R$^f$ is hydrogen, alkyl, aminoalkyl, cyanoalkyl, carboxyalkyl, alkoxycarbonylalkyl, haloalkyl, hydroxyalkyl, alkoxyalkyl, cycloalkyl, cycloalkylalkyl, dicycloalkylalkyl, aryl, aralkyl, heteroaryl, heteroaralkyl, heterocyclyl, bridged heterocyclyl, heterocyclylalkyl, or alkylsulfonyl) wherein cycloalkyl, aryl, heteroaryl, and heterocyclyl either alone or in cycloalkylalkyl, aralkyl, heteroaralkyl, or heterocyclylalkyl in $R^f$ is optionally substituted with $R^g$, $R^h$, or $R^i$ independently selected from alkyl, cycloalkyl, hydroxyl, alkoxy, alkoxycarbonyl, halo, haloalkyl, and haloalkoxy. Within embodiment 13, in another group of compounds $R^4$ is $NR^eR^f$ (where $R^e$ is hydrogen or alkyl and $R^f$ is hydrogen, alkyl, haloalkyl, hydroxyalkyl, alkoxyalkyl, cycloalkyl, cycloalkylalkyl, aryl, aralkyl, heteroaryl, heteroaralkyl, heterocyclyl, heterocyclylalkyl, or alkylsulfonyl) wherein cycloalkyl, aryl, heteroaryl, and heterocyclyl either alone or in cycloalkylalkyl, aralkyl, heteroaralkyl, or heterocyclylalkyl in $R^f$ is optionally substituted with $R^g$, $R^h$, or $R^i$ independently selected from alkyl, hydroxyl, alkoxy, halo, haloalkyl, and haloalkoxy. Within embodiment 13, in another group of compounds $R^4$ is $NR^eR^f$ (where $R^e$ is hydrogen or alkyl and $R^f$ is hydrogen, alkyl, cycloalkyl, cycloalkylalkyl, aryl, aralkyl, heteroaryl, heteroaralkyl, heterocyclyl, or heterocyclylalkyl) wherein cycloalkyl, aryl, heteroaryl, and heterocyclyl either alone or in cycloalkylalkyl, aralkyl, heteroaralkyl, or heterocyclylalkyl in $R^f$ is optionally substituted with $R^g$, $R^h$, or $R^i$ independently selected from alkyl, hydroxyl, alkoxy, halo, haloalkyl, and haloalkoxy. Within embodiment 13, in another group of compounds $R^4$ is $NR^eR^f$ (where $R^e$ is hydrogen and $R^f$ is as defined in embodiment 13 above). Within this embodiment 13, in another group of compounds $R^4$ is —NH-alkyl, preferably $R^4$ is —NH-methyl, —NH-ethyl, —NH-n-propyl, —NH-isopropyl, —NH-n-butyl, —NH-isobutyl, —NH-sec-butyl, —NH-tert-butyl, —NH-(2-ethylbutyl), or NH-pentyl (all isomers). Within this embodiment 13, in another group of compounds $R^4$ is —NH-alkyl, preferably $R^4$ is —NH-methyl, —NH-ethyl, —NH-n-propyl, —NH-isopropyl, —NH-n-butyl, —NH-isobutyl, —NH-tert-butyl, or NH-pentyl (all isomers), more preferably —NH-methyl, —NH— ethyl, —NH-n-propyl, or —NH-isopropyl. Within this embodiment 13, in another group of compounds $R^4$ is —NH-cycloalkyl optionally substituted with $R^g$ or $R^h$ independently selected from alkyl, hydroxyl, alkoxy, halo, haloalkyl, and haloalkoxy, preferably $R^4$ is —NH-cyclopropyl, —NH— cyclobutyl, —NH-cyclopentyl, —NH-cyclohexyl, —NH-(3-hydroxycyclobutyl), —NH-(3-methoxycyclobutyl), —NH-(3-fluorocyclobutyl), —NH-(3,3-difluorocyclobutyl), —NH-(3,3-dimethylcyclobutyl), —NH-(3-hydroxycyclopentyl), or —NH-(4-hydroxy-4-methylcyclohexyl), more preferably —NH-cyclopropyl, NH-cyclopentyl, or NH-cyclohexyl. Within this embodiment 13, in another group of compounds $R^4$ is —NH-cycloalkyl optionally substituted with $R^g$ or $R^h$ independently selected from alkyl, hydroxyl, alkoxy, halo, haloalkyl, and haloalkoxy, preferably $R^4$ is —NH— cyclopropyl, —NH-cyclobutyl, —NH-cyclopentyl, —NH-cyclohexyl, —NH-(3-fluorocyclobutyl), —NH-(3,3-difluorocyclobutyl), or —NH-(3,3-dimethylcyclobutyl), more preferably —NH-cyclopropyl, NH-cyclopentyl, or NH-cyclohexyl. Within this embodiment 13, in another group of compounds $R^4$ is —NH-heterocyclyl optionally substituted with $R^g$, $R^h$, or $R^i$ independently selected from alkyl, cycloalkyl, hydroxyl, alkoxy, halo, haloalkyl, and haloalkoxy, preferably $R^4$ is —NH-piperidin-4-yl, —NH-tetrahydropyran-4-yl, —NH-tetrahydrofuran-3-yl, —NH-(2,6-dimethyltetrahydropyran-4-yl), —NH-(1-alkylpiperidin-4-yl), —NH-(oxetan-3-yl), —NH-(1-methyl-2-oxopyrrolidin-3-yl), —NH-(1-isopropyl-2-oxopyrrolidin-3-yl), —NH-(5-oxopyrrolidin-3-yl), —NH-(1-methyl-5-oxopyrrolidin-3-yl), —NH-(1-ethyl-5-oxopyrrolidin-3-yl), —NH-(1-cyclobutyl-5-oxopyrrolidin-3-yl), —NH-(6-oxopiperidin-3-yl), —NH-(1-methyl-6-oxopiperidin-3-yl), —NH-(2-oxopiperidin-4-yl), —NH-(1-methyl-2-oxopiperidin-4-yl), —NH-(1-ethyl-2-oxopiperidin-4-yl), or —NH-(1-isopropyl-2-oxopiperidin-4-yl). Within this embodiment 13, in another group of compounds $R^4$ is —NH-heterocyclyl optionally substituted with $R^g$, $R^h$, or $R^i$ independently selected from alkyl, hydroxyl, alkoxy, halo, haloalkyl, and haloalkoxy, preferably $R^4$ is —NH-piperidin-4-yl, —NH-tetrahydropyran-4-yl, —NH-tetrahydrofuran-3-yl, —NH-(2,6-dimethyltetrahydropyran-4-yl), or —NH-(1-alkylpiperidin-4-yl). Within this embodiment 13, in another group of compounds $R^4$ is —NH-(bridged heterocyclyl), preferably $R^4$ is —NH-(8-oxabicyclo[3.2.1]octan-3-yl). Within this embodiment 13, in another group of compounds $R^4$ is —NH-cycloalkylalkyl optionally substituted with $R^g$ or $R^h$ independently selected from alkyl, hydroxyl, alkoxy, halo, haloalkyl, and haloalkoxy, preferably $R^4$ is —NH—$CH_2$-cycloalkyl optionally substituted with $R^g$ or $R^h$ independently selected from alkyl, hydroxyl, alkoxy, halo, haloalkyl, and haloalkoxy, more preferably $R^4$ is —NH—$CH_2$-cyclopropyl, —NH—$CH_2$-cyclobutyl, —NH—$CH_2$-cyclopentyl, —NH—$CH_2$-cyclohexyl, —NH—$CH_2$-(3-fluorocyclobutyl), —NH—$CH_2$-(3,3-difluorocyclobutyl), —NH—$CH_2$-(3,3-dimethylcyclobutyl), —NH—$CH_2$-(1-methylcyclopropyl), —NH—$CH_2$-(1-methylcyclobutyl), —NH—$(CH_2)_2$-cyclopropyl, —NH—$(CH_2)_2$-cyclobutyl, NH—$(CH_2)_2$-cyclopentyl, or NH—$(CH_2)_2$-cyclohexyl, even more preferably —NH—$CH_2$-cyclopropyl or NH—$CH_2$-cyclobutyl. Within this embodiment 13, in another group of compounds $R^4$ is —NH-cycloalkylalkyl optionally substituted with $R^g$ or $R^h$ independently selected from alkyl, hydroxyl, alkoxy, halo, haloalkyl, and haloalkoxy, preferably $R^4$ is —NH—$CH_2$-cycloalkyl optionally substituted with $R^g$ or $R^h$ independently selected from alkyl, hydroxyl, alkoxy, halo, haloalkyl, and haloalkoxy, more preferably $R^4$ is —NH—$CH_2$-cyclopropyl, —NH—$CH_2$-cyclobutyl, —NH—$CH_2$-cyclopentyl, —NH—$CH_2$-cyclohexyl, —NH—$CH_2$-(3-fluorocyclobutyl), —NH—$CH_2$-(3,3-difluorocyclobutyl), —NH—$CH_2$-(3,3-dimethylcyclobutyl), —NH—$CH_2$-(1-methylcyclopropyl), —NH—$CH_2$-(1-methylcyclobutyl), —NH—$(CH_2)_2$-cyclopropyl, NH—$(CH_2)_2$-cyclopentyl, or NH—$(CH_2)_2$-cyclohexyl, even more preferably —NH—$CH_2$-cyclopropyl or NH—$CH_2$-cyclobutyl. Within this embodiment 13, in another group of compounds $R^4$ is —NH-dicycloalkylalkyl, preferably $R^4$ is —NH-(dicyclopropylmethyl). Within this embodiment 13, in another group of compounds $R^4$ is —NH-(aminoalkyl), preferably $R^4$ is —NH-(6-aminohexyl). Within this embodiment 13, in another group of compounds $R^4$ is —NH-(cyanoalkyl), preferably $R^4$ is —NH-(2-cyanoethyl) or —NH-(3-cyanopropyl). Within this embodiment 13, in another group of compounds $R^4$ is —NH-(carboxyalkyl) or —NH-(alkoxycarbonylalkyl), preferably $R^4$ is —NH-(carboxymethyl) or —NH-(2-methoxy-2-oxoethyl). Within this embodiment 13, in another group of compounds $R^4$ is —NH-(hydroxyalkyl) or —NH-(alkoxyalkyl), preferably $R^4$ is —NH-(2-hydroxyethyl), —NH-(3-hydroxybutyl), NH-(3-hydroxy-3-methylbutyl), —NH-(2-hydroxypropyl), —NH-(3-hydroxypropyl), —NH-(2-hydroxy-2-methylpropyl), —NH-(1,3-dihydroxypropan-2-yl), —NH-(2-methoxyethyl), —NH-(2-methoxypropyl), —NH-(3-methoxypropyl), —NH-(3-methoxy-3-methylbutyl), or —NH-(3-methoxybutyl). Within this embodiment 13, in another group of compounds $R^4$ is —NH-(hydroxyalkyl) or —NH-(alkoxyalkyl), preferably $R^4$ is —NH-(2-hydroxyethyl), —NH-(2-hydroxybutyl), NH-(2- hydroxy-2-methylbutyl), —NH-(2-methoxyethyl), —NH-(2-methoxy-2-methylbutyl), or —NH-(2-methoxybutyl). Within this embodiment 13, in another group of compounds $R^4$ is —NH-heterocyclylalkyl optionally substituted with $R^g$, $R^h$, or $R^i$ independently selected from alkyl, hydroxyl, alkoxy, alkoxycarbonyl, halo, haloalkyl, and haloalkoxy, preferably $R^4$ is —NH—CH$_2$-oxetan-3-yl, —NH—CH$_2$-piperidin-4-yl, —NH—CH$_2$-tetrahydropyran-4-yl, —NH—CH$_2$-(tetrahydropyran-2-yl), —NH—CH$_2$-tetrahydrofuran-3-yl, —NH—CH$_2$-(1-alkylpiperidin-4-yl), —NH—CH$_2$-(1-(methoxycarbonyl)azetidin-3-yl), —NH—(CH$_2$)$_2$-oxetan-3-yl, —NH—(CH$_2$)$_2$-piperidin-4-ylethyl, —NH—(CH$_2$)$_2$-tetrahydropyran-4-yl, —NH—(CH$_2$)$_2$-tetrahydrofuran-3-yl, —NH—(CH$_2$)$_2$—(1-alkylpiperidin-4-yl), or —NH—(CH$_2$)$_2$-morpholin-4-yl. Within this embodiment 13, in another group of compounds $R^4$ is —NH-heterocyclylalkyl optionally substituted with $R^g$, $R^h$, or $R^i$ independently selected from alkyl, hydroxyl, alkoxy, halo, haloalkyl, and haloalkoxy, preferably $R^4$ is —NH—CH$_2$-oxetan-3-yl, —NH—CH$_2$-piperidin-4-yl, —NH—CH$_2$-tetrahydropyran-4-yl, —NH—CH$_2$-tetrahydrofuran-3-yl, —NH—CH$_2$-(1-alkylpiperidin-4-yl), —NH—(CH$_2$)$_2$-oxetan-3-yl, —NH—(CH$_2$)$_2$-piperidin-4-ylethyl, —NH—(CH$_2$)$_2$-tetrahydropyran-4-yl, —NH—(CH$_2$)$_2$-tetrahydrofuran-3-yl, or —NH—(CH$_2$)$_2$-(1-alkylpiperidin-4-yl). Within this embodiment 13, in another group of compounds $R^4$ is —NH-haloalkyl, preferably $R^4$ is —NH—2-fluoroethyl, —NH—2,2-difluoroethyl, —NH-(3,3,3-trifluoroethyl), —NH-(3-fluoropropyl), —NH-(3,3-difluoropropyl), or —NH-(3,3,3-trifluoropropyl). Within this embodiment 13, in another group of compounds $R^4$ is —NH-heteroaralkyl optionally substituted with $R^g$ or $R^h$ independently selected from alkyl, hydroxyl, alkoxy, halo, haloalkyl, and haloalkoxy, preferably $R^4$ is —NH—CH$_2$-pyridin-2-yl, —NH—CH$_2$-pyridin-3-yl, or —NH—CH$_2$-pyridin-4-yl.

Representative compounds of Formula (I) or a salt thereof are disclosed in Tables 1 and 2 below:

TABLE 1

| Entry | Name | MS Found |
|---|---|---|
| 1 | 2-methoxy-N-methyl-3-[3-(pyrrolidin-1-yl)propoxy]acridin-9-amine | 366.2 |
| 2 | 2-methoxy-N-(propan-2-yl)-3-[3-(pyrrolidin-1-yl)propoxy]-acridin-9-amine | 394.2 |
| 3 | 2-methoxy-N-(oxan-4-yl)-3-[3-(pyrrolidin-1-yl)propoxy]-acridin-9-amine trifluoroacetate | 436.3 |
| 4 | 2-methoxy-N-(1-methylpiperidin-4-yl)-3-[3-(pyrrolidin-1-yl)propoxy]acridin-9-amine trifluoroacetate | 449.3 |
| 5 | 2-methoxy-N-[1-(propan-2-yl)piperidin-4-yl]-3-[3-(pyrrolidin-1-yl)propoxy]acridin-9-amine trifluoroacetate | 477.4 |
| 6 | 2-methoxy-3-[3-(pyrrolidin-1-yl)propoxy]acridin-9-ol formate | 353.3 |
| 7 | 9-ethoxy-2-methoxy-3-[3-(pyrrolidin-1-yl)propoxy]acridine formate | 381.3 |
| 8 | 3-[3-(pyrrolidin-1-yl)propoxy]acridin-9-ol trifluoroacetate | 323.2 |
| 9 | 2-chloro-N-methyl-3-[3-(pyrrolidin-1-yl)propoxy]acridin-9-amine formate | 370.2 |
| 10 | N-methyl-3-[3-(pyrrolidin-1-yl)propoxy]acridin-9-amine formate | 336.3 |
| 11 | N,2-dimethyl-3-[3-(pyrrolidin-1-yl)propoxy]acridin-9-amine formate | 350.3 |
| 12 | N-ethyl-2-methyl-3-[3-(pyrrolidin-1-yl)propoxy]acridin-9-amine formate | 364.3 |
| 13 | 2-methyl-N-(propan-2-yl)-3-[3-(pyrrolidin-1-yl)propoxy]acridin-9-amine formate | 378.4 |
| 14 | 3-[3-(diethylamino)propoxy]-2-methoxy-N-methylacridin-9-amine trifluoroacetate | 368.3 |
| 15 | 2-methoxy-N-methyl-3-[3-(piperidin-1-yl)propoxy]acridin-9-amine formate | 380.3 |
| 16 | 7-methoxy-N-[1-(propan-2-yl)piperidin-4-yl]-6-[3-(pyrrolidin-1-yl)propoxy]-1,2,3,4-tetrahydroacridin-9-amine trifluoroacetate | 481.4 |
| 17 | 7-methoxy-6-[3-(pyrrolidin-1-yl)propoxy]-1,2,3,4-tetrahydroacridine formate | 341.2 |
| 18 | 7-methoxy-N-(1-methylpiperidin-4-yl)-6-[3-(pyrrolidin-1-yl)propoxy]-1,2,3,4-tetrahydroacridin-9-amine trifluoroacetate | 453.3 |
| 19 | 7-methoxy-N-(propan-2-yl)-6-[3-(pyrrolidin-1-yl)propoxy]-1H,2H,3H-cyclopenta[b]quinolin-9-amine formate | 384.3 |
| 20 | 7-methoxy-N-(oxan-4-yl)-6-[3-(pyrrolidin-1-yl)propoxy]-1H,2H,3H-cyclopenta[b]quinolin-9-amine | 426.3 |
| 21 | N-{7-methoxy-6-[3-(pyrrolidin-1-yl)propoxy]-1H,2H,3H-cyclopenta[b]quinolin-9-yl}-1-methylpiperidin-4-amine trifluoroacetate | 439.3 |
| 22 | 7-methoxy-N-(propan-2-yl)-6-[3-(pyrrolidin-1-yl)propoxy]-1,2,3,4-tetrahydroacridin-9-amine trifluoroacetate | 398.3 |
| 23 | 7-methoxy-N-(oxan-4-yl)-6-[3-(pyrrolidin-1-yl)propoxy]-1,2,3,4-tetrahydroacridin-9-amine trifluoroacetate | 440.3 |
| 24 | N-{7-methoxy-6-[3-(pyrrolidin-1-yl)propoxy]-1H,2H,3H-cyclopenta[b]quinolin-9-yl}-1-(propan-2-yl)piperidin-4-amine trifluoroacetate | 467.3 |
| 25 | 7-methoxy-N-methyl-6-[3-(pyrrolidin-1-yl)propoxy]-1,2,3,4-tetrahydroacridin-9-amine trifluoroacetate | 370.2 |
| 26 | 7-methoxy-N-methyl-6-[3-(pyrrolidin-1-yl)propoxy]-1H,2H,3H-cyclopenta[b]quinolin-9-amine formate | 356.2 |
| 27 | 7-methoxy-N-ethyl-6-[3-(pyrrolidin-1-yl)propoxy]-1H,2H,3H-cyclopenta[b]quinolin-9-amine formate | 370.2 |
| 28 | 7-methoxy-N-ethyl-6-[3-(pyrrolidin-1-yl)propoxy]-1,2,3,4-tetrahydroacridin-9-amine | 384.3 |
| 29 | 6-[3-(3-fluoropyrrolidin-1-yl)propoxy]-7-methoxy-N-methyl-1H,2H,3H-cyclopenta[b]quinolin-9-amine | 374.5 |
| 30 | 2-methoxy-3-[3-(morpholin-4-yl)propoxy]-N-(propan-2-yl)acridin-9-amine trifluoroacetate | 410.2 |
| 31 | N-cyclopropyl-7-methoxy-6-[3-(pyrrolidin-1-yl)propoxy]-1H,2H,3H-cyclopenta[b]quinolin-9-amine trifluoroacetate | 382.2 |
| 32 | N-(cyclopropylmethyl)-7-methoxy-6-[3-(pyrrolidin-1-yl)propoxy]-1H,2H,3H-cyclopenta[b]quinolin-9-amine formate | 396.3 |

TABLE 1-continued

| Entry | Name | MS Found |
|---|---|---|
| 33 | 7-methoxy-6-[3-(pyrrolidin-1-yl)propoxy]-1H,2H,3H-cyclopenta[b]quinolin-9-amine formate | 342.2 |
| 34 | 2-({7-methoxy-6-[3-(pyrrolidin-1-yl)propoxy]-1H,2H,3H-cyclopenta[b]quinolin-9-yl}amino)ethan-1-ol formate | 386.2 |
| 35 | N-cyclobutyl-7-methoxy-6-[3-(pyrrolidin-1-yl)propoxy]-1H,2H,3H-cyclopenta[b]quinolin-9-amine formate | 396.3 |
| 36 | N-cyclopentyl-7-methoxy-6-[3-(pyrrolidin-1-yl)propoxy]-1H,2H,3H-cyclopenta[b]quinolin-9-amine formate | 410.3 |
| 37 | 7-methoxy-N-propyl-6-[3-(pyrrolidin-1-yl)propoxy]-1H,2H,3H-cyclopenta[b]quinolin-9-amine formate | 384.2 |
| 38 | 7-methoxy-N-(2-methoxyethyl)-6-[3-(pyrrolidin-1-yl)propoxy]-1H,2H,3H-cyclopenta[b]quinolin-9-amine formate | 400.2 |
| 39 | 7-methoxy-N-[(oxetan-3-yl)methyl]-6-[3-(pyrrolidin-1-yl)propoxy]-1H,2H,3H-cyclopenta[b]quinolin-9-amine formate | 412.3 |
| 40 | N-{7-methoxy-6-[3-(pyrrolidin-1-yl)propoxy]-1H,2H,3H-cyclopenta[b]quinolin-9-yl}pyridin-2-amine formate | 419.2 |
| 41 | N-(cyclobutylmethyl)-7-methoxy-6-[3-(pyrrolidin-1-yl)propoxy]-1H,2H,3H-cyclopenta[b]quinolin-9-amine formate | 410.3 |
| 42 | 7-methoxy-N-(2-methylpropyl)-6-[3-(pyrrolidin-1-yl)propoxy]-1H,2H,3H-cyclopenta[b]quinolin-9-amine formate | 398.3 |
| 43 | N-(2,2-dimethylpropyl)-7-methoxy-6-[3-(pyrrolidin-1-yl)propoxy]-1H,2H,3H-cyclopenta[b]quinolin-9-amine formate | 412.3 |
| 44 | 7-methoxy-N-[(1-methylcyclopropyl)methyl]-6-[3-(pyrrolidin-1-yl)propoxy]-1H,2H,3H-cyclopenta[b]quinolin-9-amine formate | 410.3 |
| 45 | N-tert-butyl-7-methoxy-6-[3-(pyrrolidin-1-yl)propoxy]-1H,2H,3H-cyclopenta[b]quinolin-9-amine formate | 398.3 |
| 46 | N-benzyl-7-methoxy-6-[3-(pyrrolidin-1-yl)propoxy]-1H,2H,3H-cyclopenta[b]quinolin-9-amine formate | 432.3 |
| 47 | N-{7-methoxy-6-[3-(pyrrolidin-1-yl)propoxy]-1H,2H,3H-cyclopenta[b]quinolin-9-yl}methanesulfonamide formate | 420.2 |
| 48 | N-[(3,3-difluorocyclobutyl)methyl]-7-methoxy-6-[3-(pyrrolidin-1-yl)propoxy]-1H,2H,3H-cyclopenta[b]quinolin-9-amine | 446.4 |
| 49 | N-(3,3-difluorocyclobutyl)-7-methoxy-6-[3-(pyrrolidin-1-yl)propoxy]-1H,2H,3H-cyclopenta[b]quinolin-9-amine formate | 432.2 |
| 50 | 7-methoxy-6-[3-(pyrrolidin-1-yl)propoxy]-N-(2,2,2-trifluoroethyl)-1H,2H,3H-cyclopenta[b]quinolin-9-amine trifluoroacetate | 424.2 |
| 51 | 7-methoxy-6-[3-(pyrrolidin-1-yl)propoxy]-N-(3,3,3-trifluoropropyl)-1H,2H,3H-cyclopenta[b]quinolin-9-amine trifluoroacetate | 438.2 |
| 52 | N-(cyclopropylmethyl)-7-methoxy-6-[(1-methylpyrrolidin-3-yl)methoxy]-1H,2H,3H-cyclopenta[b]quinolin-9-amine formate | 382.5 |
| 53 | N-(2,6-dimethyloxan-4-yl)-7-methoxy-6-[3-(pyrrolidin-1-yl)propoxy]-1H,2H,3H-cyclopenta[b]quinolin-9-amine formate | 454.4 |
| 54 | 7-methoxy-N-[pyridin-2-yl)methyl]-6-[3-(pyrrolidin-1-yl)propoxy]-1H,2H,3H-cyclopenta[b]quinolin-9-amine formate | 433.6 |
| 55 | 7-methoxy-N-[(pyridin-3-yl)methyl]-6-[3-(pyrrolidin-1-yl)propoxy]-1H,2H,3H-cyclopenta[b]quinolin-9-amine formate | 433.6 |
| 56 | 7-methoxy-N-(3-methoxycyclobutyl)-6-[3-(pyrrolidin-1-yl)propoxy]-1H,2H,3H-cyclopenta[b]quinolin-9-amine formate | 426.2 |
| 57 | (1s,3s)-3-({7-methoxy-6-[3-(pyrrolidin-1-yl)propoxy]-1H,2H,3H-cyclopenta[b]quinolin-9-yl}amino)cyclobutan-1-ol formate | 412.3 |
| 58 | 5-({7-methoxy-6-[3-(pyrrolidin-1-yl)propoxy]-1H,2H,3H-cyclopenta[b]quinolin-9-yl}amino)-1-methylpiperidin-2-one trifluoroacetate | 453.4 |
| 59 | 2-({7-methoxy-6-[3-(pyrrolidin-1-yl)propoxy]-1H,2H,3H-cyclopenta[b]quinolin-9-yl}amino)propane-1,3-diol formate | 416.4 |
| 60 | 4-({7-methoxy-6-[3-(pyrrolidin-1-yl)propoxy]-1H,2H,3H-cyclopenta[b]quinolin-9-yl}amino)pyrrolidin-2-one trifluoroacetate | 425.5 |
| 61 | 4-({7-methoxy-6-[3-(pyrrolidin-1-yl)propoxy]-1H,2H,3H-cyclopenta[b]quinolin-9-yl}amino)-1-methylpyrrolidin-2-one trifluoroacetate | 439.5 |
| 62 | 5-({7-methoxy-6-[3-(pyrrolidin-1-yl)propoxy]-1H,2H,3H-cyclopenta[b]quinolin-9-yl}amino)piperidin-2-one trifluoroacetate | 439.5 |
| 63 | 4-({7-methoxy-6-[3-(pyrrolidin-1-yl)propoxy]-1H,2H,3H-cyclopenta[b]quinolin-9-yl}amino)-1-methylpiperidin-2-one formate | 453.4 |
| 64 | 4-({7-methoxy-6-[3-(pyrrolidin-1-yl)propoxy]-1H,2H,3H-cyclopenta[b]quinolin-9-yl}amino)piperidin-2-one formate | 439.4 |
| 65 | N-(dicyclopropylmethyl)-7-methoxy-6-[3-(pyrrolidin-1-yl)propoxy]-1H,2H,3H-cyclopenta[b]quinolin-9-amine formate | 436.5 |
| 66 | N1-{7-methoxy-6-[3-(pyrrolidin-1-yl)propoxy]-1H,2H,3H-cyclopenta[b]quinolin-9-yl}hexane-1,6-diamine formate | 442.4 |
| 67 | 7-methoxy-N-[2-(morpholin-4-yl)ethyl]-6-[3-(pyrrolidin-1-yl)propoxy]-1H,2H,3H-cyclopenta[b]quinolin-9-amine formate | 455.3 |
| 68 | 7-methoxy-N-(oxetan-3-yl)-6-[3-(pyrrolidin-1-yl)propoxy]-1H,2H,3H-cyclopenta[b]quinolin-9-amine formate | 398.3 |
| 69 | 1-({7-methoxy-6-[3-(pyrrolidin-1-yl)propoxy]-1H,2H,3H-cyclopenta[b]quinolin-9-yl}amino)-2-methylpropan-2-ol formate | 414.3 |
| 70 | N-{7-methoxy-6-[3-(pyrrolidin-1-yl)propoxy]-1H,2H,3H-cyclopenta[b]quinolin-9-yl}-1-methyl-1H-pyrazol-3-amine formate | 422.2 |

TABLE 1-continued

| Entry | Name | MS Found |
|---|---|---|
| 71 | methyl 3-[({7-methoxy-6-[3-(pyrrolidin-1-yl)propoxy]-1H,2H,3H-cyclopenta[b]quinolin-9-yl}amino)methyl]azetidine-1-carboxylate formate | 469.4 |
| 72 | 1-({7-methoxy-6-[3-(pyrrolidin-1-yl)propoxy]-1H,2H,3H-cyclopenta[b]quinolin-9-yl}amino)propan-2-ol formate | 400.2 |
| 73 | 7-methoxy-N-(3-methoxypropyl)-6-[3-(pyrrolidin-1-yl)propoxy]-1H,2H,3H-cyclopenta[b]quinolin-9-amine formate | 414.2 |
| 74 | 3-({7-methoxy-6-[3-(pyrrolidin-1-yl)propoxy]-1H,2H,3H-cyclopenta[b]quinolin-9-yl}amino)propan-1-ol formate | 400.2 |
| 75 | 3-({7-methoxy-6-[3-(pyrrolidin-1-yl)propoxy]-1H,2H,3H-cyclopenta[b]quinolin-9-yl}amino)-1-methylpyrrolidin-2-one | 439.3 |
| 76 | N-cyclopropyl-2-methoxy-3-[3-(pyrrolidin-1-yl)propoxy]acridin-9-amine formate | 392.3 |
| 77 | 2-methoxy-N-[(3S)-oxolan-3-yl]-3-[3-(pyrrolidin-1-yl)propoxy]acridin-9-amine formate | 422.3 |
| 78 | 2-methoxy-N-[(3R)-oxolan-3-yl]-3-[3-(pyrrolidin-1-yl)propoxy]acridin-9-amine formate | 422.3 |
| 79 | 2-methoxy-N-(oxetan-3-yl)-3-[3-(pyrrolidin-1-yl)propoxy]acridin-9-amine formate | 408.4 |
| 80 | 2-methoxy-N-{8-oxabicyclo[3.2.1]octan-3-yl}-3-[3-(pyrrolidin-1-yl)propoxy]acridin-9-amine formate | 462.3 |
| 81 | 5-({2-methoxy-3-[3-(pyrrolidin-1-yl)propoxy]acridin-9-yl}amino)-1-methylpiperidin-2-one trifluoroacetate | 463.3 |
| 82 | (1S,3R)-3-({2-methoxy-3-[3-(pyrrolidin-1-yl)propoxy]acridin-9-yl}amino)cyclopentan-1-ol formate | 436.3 |
| 83 | (1R,3R)-3-({2-methoxy-3-[3-(pyrrolidin-1-yl)propoxy]acridin-9-yl}amino)cyclopentan-1-ol formate | 436.3 |
| 84 | 4-({2-methoxy-3-[3-(pyrrolidin-1-yl)propoxy]acridin-9-yl}amino)piperidin-2-one trifluoroacetate | 449.5 |
| 85 | 1-ethyl-4-({2-methoxy-3-[3-(pyrrolidin-1-yl)propoxy]acridin-9-yl}amino)pyrrolidin-2-one trifluoroacetate | 463.5 |
| 86 | 3-({2-methoxy-3-[3-(pyrrolidin-1-yl)propoxy]acridin-9-yl}amino)-1-(propan-2-yl)pyrrolidin-2-one trifluoroacetate | 477.5 |
| 87 | 1-cyclobutyl-4-({2-methoxy-3-[3-(pyrrolidin-1-yl)propoxy]acridin-9-yl}amino)pyrrolidin-2-one trifluoroacetate | 489.4 |
| 88 | 1-ethyl-4-({2-methoxy-3-[3-(pyrrolidin-1-yl)propoxy]acridin-9-yl}amino)piperidin-2-one trifluoroacetate | 477.5 |
| 89 | 4-({2-methoxy-3-[3-(pyrrolidin-1-yl)propoxy]acridin-9-yl}amino)-1-(propan-2-yl)piperidin-2-one formate | 491.5 |
| 90 | 5-({2-methoxy-3-[3-(pyrrolidin-1-yl)propoxy]acridin-9-yl}amino)piperidin-2-one trifluoroacetate | 449.6 |
| 91 | N-[(2S)-butan-2-yl]-2-methoxy-3-[3-(pyrrolidin-1-yl)propoxy]acridin-9-amine trifluoroacetate | 408.5 |
| 92 | N-[(2R)-butan-2-yl]-2-methoxy-3-[3-(pyrrolidin-1-yl)propoxy]acridin-9-amine trifluoroacetate | 408.5 |
| 93 | 2-({2-methoxy-3-[3-(pyrrolidin-1-yl)propoxy]acridin-9-yl}amino)ethan-1-ol trifluoroacetate | 396.4 |
| 94 | 3-({2-methoxy-3-[3-(pyrrolidin-1-yl)propoxy]acridin-9-yl}amino)propan-1-ol trifluoroacetate | 410.6 |
| 95 | 2-methoxy-N-(2-methoxypropyl)-3-[3-(pyrrolidin-1-yl)propoxy]acridin-9-amine trifluoroacetate | 424.5 |
| 96 | 2-methoxy-N-[(oxolan-3-yl)methyl]-3-[3-(pyrrolidin-1-yl)propoxy]acridin-9-amine trifluoroacetate | 436.5 |
| 97 | 2-methoxy-N-[(oxan-2-yl)methyl]-3-[3-(pyrrolidin-1-yl)propoxy]acridin-9-amine trifluoroacetate | 450.5 |
| 98 | 3-({2-methoxy-3-[3-(pyrrolidin-1-yl)propoxy]acridin-9-yl}amino)propanenitrile trifluoroacetate | 405.5 |
| 99 | (1R,4R)-4-({2-methoxy-3-[3-(pyrrolidin-1-yl)propoxy]acridin-9-yl}amino)-1-methylcyclohexan-1-ol trifluoroacetate | 464.5 |
| 100 | (1S,4S)-4-({2-methoxy-3-[3-(pyrrolidin-1-yl)propoxy]acridin-9-yl}amino)-1-methylcyclohexan-1-ol trifluoroacetate | 464.5 |
| 101 | N-(cyclopropylmethyl)-2-methoxy-3-[3-(pyrrolidin-1-yl)propoxy]acridin-9-amine formate | 406.2 |
| 102 | 4-({2-methoxy-3-[3-(pyrrolidin-1-yl)propoxy]acridin-9-yl}amino)-2-methylbutan-2-ol formate | 438.2 |
| 103 | 1-({2-methoxy-3-[3-(pyrrolidin-1-yl)propoxy]acridin-9-yl}amino)-2-methylpropan-2-ol formate | 424.4 |
| 104 | 2-({2-methoxy-3-[3-(pyrrolidin-1-yl)propoxy]acridin-9-yl}amino)acetic acid formate | 410.2 |
| 105 | methyl 2-({2-methoxy-3-[3-(pyrrolidin-1-yl)propoxy]acridin-9-yl}amino)acetate formate | 424.2 |
| 106 | 4-({2-methoxy-3-[3-(pyrrolidin-1-yl)propoxy]acridin-9-yl}amino)butanenitrile formate | 419.1 |
| 107 | N-(2,6-dimethyloxan-4-yl)-2-methoxy-3-[3-(pyrrolidin-1-yl)propoxy]acridin-9-amine formate | 464.2 |
| 108 | 3-({2-methoxy-3-[3-(pyrrolidin-1-yl)propoxy]acridin-9-yl}amino)-1-methylpyrrolidin-2-one formate | 449.3 |

TABLE 1-continued

| Entry | Name | MS Found |
|---|---|---|
| 109 | 2-methoxy-N-methyl-3-[(1-methylpyrrolidin-3-yl)methoxy]acridin-9-amine trifluoroacetate | 352.2 |
| 110 | 2-methoxy-N-methyl-3-[(1-methylpiperidin-3-yl)methoxy]acridin-9-amine trifluoroacetate | 366.2 |
| 111 | 1-fluoro-7-methoxy-N-(2-methoxyethyl)-6-[3-(pyrrolidin-1-yl)propoxy]acridin-9-amine formate | 428.3 |
| 112 | (1S,3R)-3-({2-methyl-3-[3-(pyrrolidin-1-yl)propoxy]acridin-9-yl}amino)cyclopentan-1-ol trifluoroacetate | 420.5 |
| 113 | 2-chloro-N-(propan-2-yl)-3-[3-(pyrrolidin-1-yl)propoxy]acridin-9-amine trifluoroacetate | 398.8 |
| 114 | 2-methoxy-7-methyl-N-(oxan-4-yl)-3-[3-(pyrrolidin-1-yl)propoxy]acridin-9-amine formate | 450.4 |
| 115 | 2,7-dimethoxy-N-(oxan-4-yl)-3-[3-(pyrrolidin-1-yl)propoxy]acridin-9-amine trifluoroacetate | 466.5 |
| 116 | 2-methoxy-3-[(1-methylpyrrolidin-3-yl)methoxy]-N-(oxan-4-yl)acridin-9-amine formate | 422.2 |
| 117 | 3-[3-(3-fluoropyrrolidin-1-yl)propoxy]-2-methoxy-N-methylacridin-9-amine formate | 384.4 |
| 118 | 2-ethoxy-N-methyl-3-[3-(pyrrolidin-1-yl)propoxy]acridin-9-amine formate and 3-ethoxy-N-methyl-2-[3-(pyrrolidin-1-yl)propoxy]acridin-9-amine formate (1:1) | 380.4 |
| 119 | 3-[3-(dimethylamino)propoxy]-2-methoxy-N-methylacridin-9-amine trifluoroacetate | 340.2 |
| 120 | 5-fluoro-2-methoxy-N-(propan-2-yl)-3-[3-(pyrrolidin-1-yl)propoxy]acridin-9-amine formate | 412.3 |
| 121 | 8-methoxy-N-(propan-2-yl)-7-[3-(pyrrolidin-1-yl)propoxy]benzo[b]1,6-naphthyridin-10-amine formate | 395.3 |
| 122 | 8-methoxy-N-(propan-2-yl)-7-[3-(pyrrolidin-1-yl)propoxy]benzo[b]1,5-naphthyridin-10-amine formate | 395.3 |
| 123 | 1-({7-methoxy-8-[3-(pyrrolidin-1-yl)propoxy]benzo[b]1,8-naphthyridin-5-yl}amino)-2-methylpropan-2-ol formate | 425.2 |
| 124 | 7-methoxy-N-(oxan-4-yl)-6-[3-(pyrrolidin-1-yl)propoxy]-1,2,3,4-tetrahydroacridin-9-amine trifluoroacetate | 440.4 |
| 125 | N-cyclopropyl-7-methoxy-6-[3-(pyrrolidin-1-yl)propoxy]-1,2,3,4-tetrahydroacridin-9-amine trifluoroacetate | 396.5 |
| 126 | 2-({7-methoxy-6-[3-(pyrrolidin-1-yl)propoxy]-1,2,3,4-tetrahydroacridin-9-yl}amino)ethan-1-ol formate | 400.4 |
| 127 | 3-({7-methoxy-6-[3-(pyrrolidin-1-yl)propoxy]-1,2,3,4-tetrahydroacridin-9-yl}amino)cyclobutan-1-ol formate | 426.5 | or a pharmaceutically acceptable salt of any of the above compounds. If an entry in Table 1 refers to a salt, the respective parent compound and other pharmaceutically acceptable salts thereof are also encompassed by this disclosure.

TABLE 2

| Entry | Name |
|---|---|
| 1 | 7-methoxy-6-[3-(pyrrolidin-1-yl)propoxy]-1H,2H,3H-cyclopenta[b]quinolin-9-ol |
| 2 | 7-methoxy-6-[3-(pyrrolidin-1-yl)propoxy]-1,2,3,4-tetrahydroacridin-9-ol |
| 3 | 1-[3-({7-methoxy-1H,2H,3H-cyclopenta[b]quinolin-6-yl}oxy)propyl]pyrrolidine |
| 4 | 1-(3-{[2-methoxy-9-(methylamino)acridin-3-yl]oxy}propyl)-3-methylpyrrolidin-3-ol |
| 5 | 1-(3-{[2-methoxy-9-(methylamino)-5,6,7,8-tetrahydroacridin-3-yl]oxy}propyl)-3-methylpyrrolidin-3-ol |
| 6 | 1-(3-{[7-methoxy-9-(methylamino)-1H,2H,3H-cyclopenta[b]quinolin-6-yl]oxy}propyl)-3-methylpyrrolidin-3-ol |
| 7 | 1-(3-{[2-methoxy-9-(methylamino)acridin-3-yl]oxy}propyl)-3-methylazetidin-3-ol |
| 8 | 1-(3-{[2-methoxy-9-(methylamino)-5,6,7,8-tetrahydroacridin-3-yl]oxy}propyl)-3-methylazetidin-3-ol |
| 9 | 1-(3-{[7-methoxy-9-(methylamino)-1H,2H,3H-cyclopenta[b]quinolin-6-yl]oxy}propyl)-3-methylazetidin-3-ol |
| 10 | 3-[3-(3-fluoropyrrolidin-1-yl)propoxy]-2-methoxy-N-methylacridin-9-amine |
| 11 | 6-[3-(3-fluoropyrrolidin-1-yl)propoxy]-7-methoxy-N-methyl-1,2,3,4-tetrahydroacridin-9-amine |
| 12 | 3-[3-(3-fluoroazetidin-1-yl)propoxy]-2-methoxy-N-methylacridin-9-amine |
| 13 | 6-[3-(3-fluoroazetidin-1-yl)propoxy]-7-methoxy-N-methyl-1,2,3,4-tetrahydroacridin-9-amine |
| 14 | 6-[3-(3-fluoroazetidin-1-yl)propoxy]-7-methoxy-N-methyl-1H,2H,3H-cyclopenta[b]quinolin-9-amine |
| 15 | 3-{3-[(3R)-3-fluoropyrrolidin-1-yl]propoxy}-2-methoxy-N-methylacridin-9-amine |
| 16 | 6-{3-[(3R)-3-fluoropyrrolidin-1-yl]propoxy}-7-methoxy-N-methyl-1,2,3,4-tetrahydroacridin-9-amine |

TABLE 2-continued

| Entry | Name |
|---|---|
| 17 | 6-{3-[(3R)-3-fluoropyrrolidin-1-yl]propoxy}-7-methoxy-N-methyl-1H,2H,3H-cyclopenta[b]quinolin-9-amine |
| 18 | 3-{3-[(3S)-3-fluoropyrrolidin-1-yl]propoxy}-2-methoxy-N-methylacridin-9-amine |
| 19 | 6-{3-[(3S)-3-fluoropyrrolidin-1-yl]propoxy}-7-methoxy-N-methyl-1,2,3,4-tetrahydroacridin-9-amine |
| 20 | 6-{3-[(3S)-3-fluoropyrrolidin-1-yl]propoxy}-7-methoxy-N-methyl-1H,2H,3H-cyclopenta[b]quinolin-9-amine |
| 21 | 1-[3-({7-methoxy-9-[(propan-2-yl)amino]-1H,2H,3H-cyclopenta[b]quinolin-6-yl}oxy)propyl]-3-methylpyrrolidin-3-ol |
| 22 | 1-[3-({7-methoxy-9-[(propan-2-yl)amino]-1H,2H,3H-cyclopenta[b]quinolin-6-yl}oxy)propyl]-3-methylazetidin-3-ol |
| 23 | N-ethyl-3-{3-[(3R)-3-fluoropyrrolidin-1-yl]propoxy}-2-methoxyacridin-9-amine |
| 24 | N-ethyl-6-{3-[(3R)-3-fluoropyrrolidin-1-yl]propoxy}-7-methoxy-1,2,3,4-tetrahydroacridin-9-amine |
| 25 | N-ethyl-6-{3-[(3R)-3-fluoropyrrolidin-1-yl]propoxy}-7-methoxy-1H,2H,3H-cyclopenta[b]quinolin-9-amine |
| 26 | N-ethyl-3-{3-[(3S)-3-fluoropyrrolidin-1-yl]propoxy}-2-methoxyacridin-9-amine |
| 27 | N-ethyl-6-{3-[(3S)-3-fluoropyrrolidin-1-yl]propoxy}-7-methoxy-1,2,3,4-tetrahydroacridin-9-amine |
| 28 | N-ethyl-6-{3-[(3S)-3-fluoropyrrolidin-1-yl]propoxy}-7-methoxy-1H,2H,3H-cyclopenta[b]quinolin-9-amine |
| 29 | 3-{3-[(3R)-3-fluoropyrrolidin-1-yl]propoxy}-2-methoxy-N-(propan-2-yl)acridin-9-amine |
| 30 | 6-{3-[(3R)-3-fluoropyrrolidin-1-yl]propoxy}-7-methoxy-N-(propan-2-yl)-1,2,3,4-tetrahydroacridin-9-amine |
| 31 | 6-{3-[(3R)-3-fluoropyrrolidin-1-yl]propoxy}-7-methoxy-N-(propan-2-yl)-1H,2H,3H-cyclopenta[b]quinolin-9-amine |
| 32 | 3-{3-[(3S)-3-fluoropyrrolidin-1-yl]propoxy}-2-methoxy-N-(propan-2-yl)acridin-9-amine |
| 33 | 6-{3-[(3S)-3-fluoropyrrolidin-1-yl]propoxy}-7-methoxy-N-(propan-2-yl)-1,2,3,4-tetrahydroacridin-9-amine |
| 34 | 6-{3-[(3S)-3-fluoropyrrolidin-1-yl]propoxy}-7-methoxy-N-(propan-2-yl)-1H,2H,3H-cyclopenta[b]quinolin-9-amine |
| 35 | N-cyclopropyl-3-{3-[(3R)-3-fluoropyrrolidin-1-yl]propoxy}-2-methoxyacridin-9-amine |
| 36 | N-cyclopropyl-6-{3-[(3R)-3-fluoropyrrolidin-1-yl]propoxy}-7-methoxy-1,2,3,4-tetrahydroacridin-9-amine |
| 37 | N-cyclopropyl-6-{3-[(3R)-3-fluoropyrrolidin-1-yl]propoxy}-7-methoxy-1H,2H,3H-cyclopenta[b]quinolin-9-amine |
| 38 | N-cyclopropyl-3-{3-[(3S)-3-fluoropyrrolidin-1-yl]propoxy}-2-methoxyacridin-9-amine |
| 39 | N-cyclopropyl-6-{3-[(3S)-3-fluoropyrrolidin-1-yl]propoxy}-7-methoxy-1,2,3,4-tetrahydroacridin-9-amine |
| 40 | N-cyclopropyl-6-{3-[(3S)-3-fluoropyrrolidin-1-yl]propoxy}-7-methoxy-1H,2H,3H-cyclopenta[b]quinolin-9-amine |
| 41 | 2-methoxy-N-methyl-3-[3-(morpholin-4-yl)propoxy]acridin-9-amine |
| 42 | 7-methoxy-N-methyl-6-[3-(morpholin-4-yl)propoxy]-1,2,3,4-tetrahydroacridin-9-amine |
| 43 | 7-methoxy-N-methyl-6-[3-(morpholin-4-yl)propoxy]-1H,2H,3H-cyclopenta[b]quinolin-9-amine |
| 44 | N-ethyl-2-methoxy-3-[3-(morpholin-4-yl)propoxy]acridin-9-amine |
| 45 | N-ethyl-7-methoxy-6-[3-(morpholin-4-yl)propoxy]-1,2,3,4-tetrahydroacridin-9-amine |
| 46 | N-ethyl-7-methoxy-6-[3-(morpholin-4-yl)propoxy]-1H,2H,3H-cyclopenta[b]quinolin-9-amine |
| 47 | 7-methoxy-6-[3-(morpholin-4-yl)propoxy]-N-(propan-2-yl)-1,2,3,4-tetrahydroacridin-9-amine |
| 48 | 7-methoxy-6-[3-(morpholin-4-yl)propoxy]-N-(propan-2-yl)-1H,2H,3H-cyclopenta[b]quinolin-9-amine |
| 49 | N-cyclopropyl-2-methoxy-3-[3-(morpholin-4-yl)propoxy]acridin-9-amine |
| 50 | N-cyclopropyl-7-methoxy-6-[3-(morpholin-4-yl)propoxy]-1,2,3,4-tetrahydroacridin-9-amine |
| 51 | N-cyclopropyl-7-methoxy-6-[3-(morpholin-4-yl)propoxy]-1H,2H,3H-cyclopenta[b]quinolin-9-amine |
| 52 | 7-methoxy-N-[(1-methylcyclobutyl)methyl]-6-[3-(pyrrolidin-1-yl)propoxy]-1H,2H,3H-cyclopenta[b]quinolin-9-amine |
| 53 | N-[(3,3-dimethylcyclobutyl)methyl]-7-methoxy-6-[3-(pyrrolidin-1-yl)propoxy]-1H,2H,3H-cyclopenta[b]quinolin-9-amine |
| 54 | N-[(3-fluorocyclobutyl)methyl]-7-methoxy-6-[3-(pyrrolidin-1-yl)propoxy]-1H,2H,3H-cyclopenta[b]quinolin-9-amine |
| 55 | N-(3-fluorocyclobutyl)-7-methoxy-6-[3-(pyrrolidin-1-yl)propoxy]-1H,2H,3H-cyclopenta[b]quinolin-9-amine |
| 56 | N-(2-fluoroethyl)-7-methoxy-6-[3-(pyrrolidin-1-yl)propoxy]-1H,2H,3H-cyclopenta[b]quinolin-9-amine |
| 57 | N-(2,2-difluoroethyl)-7-methoxy-6-[3-(pyrrolidin-1-yl)propoxy]-1H,2H,3H-cyclopenta[b]quinolin-9-amine |
| 58 | N-(3-fluoropropyl)-7-methoxy-6-[3-(pyrrolidin-1-yl)propoxy]-1H,2H,3H-cyclopenta[b]quinolin-9-amine |
| 59 | N-(3,3-difluoropropyl)-7-methoxy-6-[3-(pyrrolidin-1-yl)propoxy]-1H,2H,3H-cyclopenta[b]quinolin-9-amine |
| 60 | 7-methoxy-N-(pentan-3-yl)-6-[3-(pyrrolidin-1-yl)propoxy]-1H,2H,3H-cyclopenta[b]quinolin-9-amine |
| 61 | N-(butan-2-yl)-7-methoxy-6-[3-(pyrrolidin-1-yl)propoxy]-1H,2H,3H-cyclopenta[b]quinolin-9-amine |

TABLE 2-continued

| Entry | Name |
|---|---|
| 62 | 7-methoxy-N-(pentan-2-yl)-6-[3-(pyrrolidin-1-yl)propoxy]-1H,2H,3H-cyclopenta[b]quinolin-9-amine |
| 63 | 7-methoxy-N-(2-methylbutyl)-6-[3-(pyrrolidin-1-yl)propoxy]-1H,2H,3H-cyclopenta[b]quinolin-9-amine |
| 64 | N-(2-ethylbutyl)-7-methoxy-6-[3-(pyrrolidin-1-yl)propoxy]-1H,2H,3H-cyclopenta[b]quinolin-9-amine |
| 65 | N-(2-cyclobutylethyl)-7-methoxy-6-[3-(pyrrolidin-1-yl)propoxy]-1H,2H,3H-cyclopenta[b]quinolin-9-amine |
| 66 | N-(2-cyclopropylethyl)-7-methoxy-6-[3-(pyrrolidin-1-yl)propoxy]-1H,2H,3H-cyclopenta[b]quinolin-9-amine |
| 67 | N-(2-cyclopentylethyl)-7-methoxy-6-[3-(pyrrolidin-1-yl)propoxy]-1H,2H,3H-cyclopenta[b]quinolin-9-amine |
| 68 | N-(2-cyclohexylethyl)-7-methoxy-6-[3-(pyrrolidin-1-yl)propoxy]-1H,2H,3H-cyclopenta[b]quinolin-9-amine |
| 69 | N-(cyclohexylmethyl)-7-methoxy-6-[3-(pyrrolidin-1-yl)propoxy]-1H,2H,3H-cyclopenta[b]quinolin-9-amine |
| 70 | 7-methoxy-N-[(pyridin-4-yl)methyl]-6-[3-(pyrrolidin-1-yl)propoxy]-1H,2H,3H-cyclopenta[b]quinolin-9-amine |
| 71 | 4-({7-methoxy-6-[3-(pyrrolidin-1-yl)propoxy]-1H,2H,3H-cyclopenta[b]quinolin-9-yl}amino)-2-methylbutan-2-ol |
| 72 | 7-methoxy-N-(3-methoxy-3-methylbutyl)-6-[3-(pyrrolidin-1-yl)propoxy]-1H,2H,3H-cyclopenta[b]quinolin-9-amine |
| 73 | 4-({7-methoxy-6-[3-(pyrrolidin-1-yl)propoxy]-1H,2H,3H-cyclopenta[b]quinolin-9-yl}amino)butan-2-ol |
| 74 | 7-methoxy-N-(3-methoxybutyl)-6-[3-(pyrrolidin-1-yl)propoxy]-1H,2H,3H-cyclopenta[b]quinolin-9-amine |
| 75 | N-butyl-7-methoxy-6-[3-(pyrrolidin-1-yl)propoxy]-1H,2H,3H-cyclopenta[b]quinolin-9-amine | or a pharmaceutically acceptable salt of any of the above compounds.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of the present disclosure such as compound of Formula (I) where B is phenyl or 6-membered heteroaryl containing one or two nitrogen atoms and other groups are as defined in the Summary can be prepared as illustrated and described in Scheme 1 below.

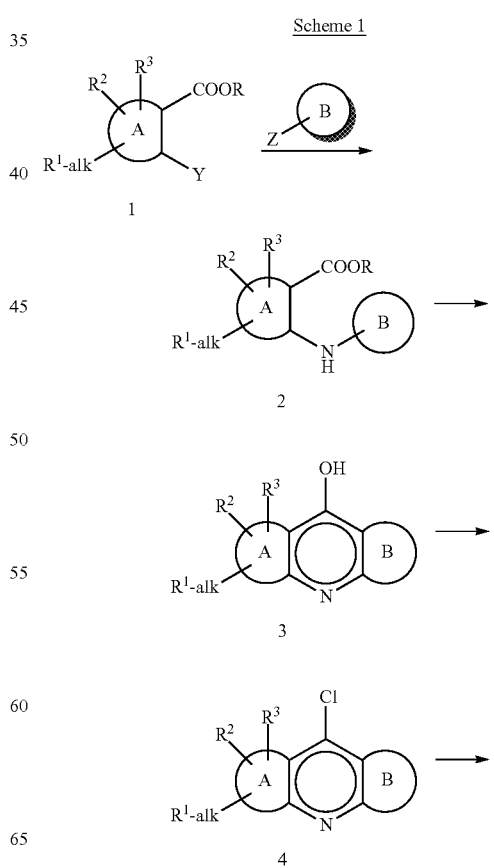

Scheme 1

-continued

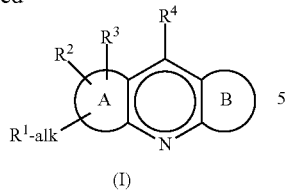

(I)

Reacting a carboxylate compound of formula 1 where R is hydrogen, alkyl, preferably methyl, -alk-R$^1$, R$^2$ and R$^3$ are as defined in the Summary or a precursor group thereof and Y is amino or halo with a compound of formula 2 where ring B is phenyl or 6 membered heteroaryl as defined in the Summary and Z is halo when Y is amino or Z is amino when Y is halo under Buchwald amination reaction conditions provides a compound of formula 2. Compounds of formula 1 where Y is amino group can be prepared from methyl 4,5-dimethoxy-2-nitrobenzoate or methyl 1H-pyrrole-3-carboxylate by methods well known in the art (see references in the synthetic example below).

The carboxylate group of compound 2 can undergo intramolecular Friedel-Crafts acylation with carbon atom ortho to the carbon substituted with amino group in ring B in the presence of acid or Lewis acid catalyst to give cyclic hydroxyl compound 3. Treatment of compound 3 with a chlorinating reagent such as PCl$_3$ or POCl$_3$ under reaction conditions well known in the art provides compound of formula 4. Compound 4 is then converted to a compound of Formula (I) by methods well known in the art. For example, compounds of Formula (I) where R$^4$ is NR$^e$R$^f$ can be prepared by reacting compound 4 with amines of formula HNR$^e$R$^f$ optionally in the presence of a non-nucleophic base such as diisopropylethylamine and the like, or under Buchwald arylhalide-amine coupling reaction conditions. Compounds of Formula (I) where R$^4$ is OR$^d$ can be prepared by reacting compound 4 with an alkoxide (R$^d$OM, M=Na, Li, or K) or an alcohol of formula R$^d$OH optionally in the presence of a non-nucleophic base such as diisopropylethylamine, pyridine, and the like.

Compounds of Formula (I) where R$^4$ is alkyl can be prepared by reacting compound 4 with alkylboronates under Suzuki conditions. Furthermore, under various reduction conditions (e.g., hydrogenation), the chloride atom of compound 3 can also be replaced by a hydrogen to produce compounds of Formula (I) where R$^4$ is hydrogen.

Compounds of Formula (I) where B is cycloalkyl or heterocyclyl and other groups as defined in the Summary can be prepared as illustrated and described in Scheme 2 below.

Scheme 2

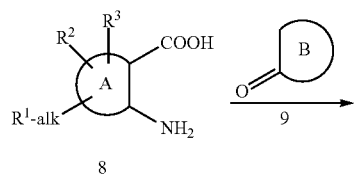

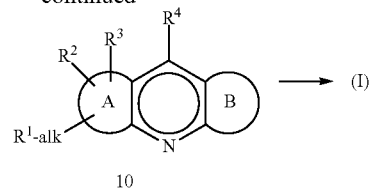

Reaction of a compound of formula 8 where -alk-R$^1$, R$^2$ and R$^3$ are as defined in the Summary or a precursor group thereof with a cyclic ketone of formula 9 where B is cycloalkyl or heterocyclyl ring in the presence of POCl$_3$ provides a compound of formula 10. Compound 10 can be converted to a compound of Formula (I) where ring B is cycloalkyl or heterocyclyl as defined in the Summary either via Buchwald arylhalide-amine coupling reaction or under conditions as described in Scheme 1 above to provide compounds of Formula (I). Compounds of formula 8 can be prepared from methyl 2-amino-5-methoxy-4-[3-(pyrrolidin-1-yl)propoxy]benzoate by methods well known in the art. Compounds of formula 9 such as cyclopentanone, cyclohexanone, cycloheptanone, oxepan-4-one, thiepan-4-one and 1-methylazepan-4-one are commercially available.

Intermediates

Also provided are certain intermediates, or salts thereof, useful in the preparation of compounds of Formula (I). In further embodiments, provided is an intermediate of Formula (II), or a salt thereof,

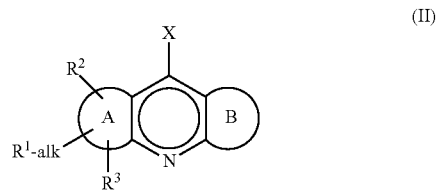

wherein X is halo (e.g., chloro), tosylate, mesylate, or triflate; and the remaining variables are as defined herein for Formula (I) (such as any one of embodiments 1 and 3 to 9 above and group(s) contained therein). Within the embodiments of the intermediate of Formula (II), in one group of intermediates X is halo, preferably chloro. Representative intermediates are shown in the Examples.

Testing

The G9a inhibitory activity of the compounds of the present disclosure can be tested using the in vitro assay described in Biological Examples 1 below. The ability of the compounds of the disclosure to stimulated fetal hemoglobin can be tested using the in vitro assay described in Biological Example 2 below.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, or axitinib; EGFR inhibitor such as afatinib, brivanib, carbozatinib, erlotinib, gefitinib, neratinib, or lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, or TG100-115; MTOR inhibitor such as rapamycin (sirolimus), temsirolimus, everolimus, XL388, XL765, AZD2013, PF04691502, PKI-587, BEZ235, or GDC0349; MEK inhibitor such as AZD6244, trametinib, PD184352, pimasertinib, GDC-0973, or AZD8330; and proteasome inhibitor such as carfilzomib, MLN9708, delanzomib, or bortezomib.

Other anti-cancer agents that can be employed in combination with a compound of this disclosure include Adriamycin; Dactinomycin; Bleomycin; Vinblastine; Cisplatin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer agents that can be employed in combination with a compound of the disclosure such as 8-(3-(4-acryloylpiperazin-1-yl)propyl)-6-(2,6-dichloro-3,5-dimethoxyphenyl)-2-(methylamino)pyrido[2,3-d]pyrimidin-7 (8H)-one used to determine the anti-tumor activity in HGS and RT4 tumor models (Example 4 below: In HGS model, vehicle dosed group reached tumor size 645 dosing at day 42 after inoculation whereas for animals treated with 20/kg of compound, the tumor size was 55 mm3 showing significant antitumor activity and induced tumor regression), include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone;

dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereguiin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+–38-iethylstilbe cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub. 11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), pyrimidine analogs (e.g., cytarabine), or purine analogs (e.g., mercaptopurine, thioguanine, pentostatin).

Examples of natural products useful in combination with a compound of this disclosure include but are not limited to vinca alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of this disclosure) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), pyrimidine analogs (e.g., fluorouracil, floxuridine, cytarabine), or purine analogs (e.g., mercaptopurine, thioguanine, pentostatin.

Examples of hormones and antagonists useful in combination a compound of this disclosure include, but are not limited to, adrenocorticosteroids (e.g., prednisone), progestins (e.g., hydroxyprogesterone caproate, megestrol acetate, and medroxyprogesterone acetate), estrogens (e.g., −40-iethylstilbestrol, and ethinyl estradiol), antiestrogen (e.g., tamoxifen), androgens (e.g., testosterone propionate, fluoxymesterone), antiandrogen (e.g., flutamide), and gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), and adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), and 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

SYNTHETIC EXAMPLES

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof.

Synthesis of Exemplary Intermediates

Reference 1

Synthesis of 9-chloro-2-methoxy-3-[3-(pyrrolidin-1-yl)propoxy]acridine (Intermediate I)

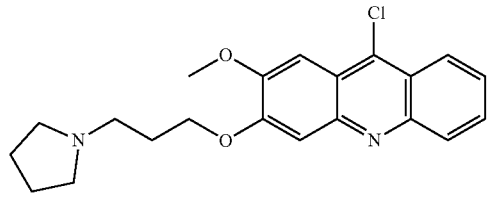 [SMILES: COc1cc2c(Cl)c3ccccc3nc2cc1OCCCN1CCCC1]

Step 1

To a 2-L round-bottom flask was added methyl 4-hydroxy-3-methoxybenzoate (100 g, 548.93 mmol, 1.00 eq.), 1-chloro-3-iodopropane (224 g, 1.10 mol, 2.0 eq.), $K_2CO_3$ (22.7 g, 3.00 eq.) followed by $CH_3CN$ (1 L). The resulting mixture was allowed to stir at 80° C. for 3 h. The reaction mixture was cooled to rt, the solids were filtered off and washed with EtOAc. The filtrate was concentrated under reduced pressure to afford the desired crude product of methyl 4-(3-chloropropoxy)-3-methoxybenzoate as a white solid (128 g, 90%).

Step 2

Into a 0° C. solution of methyl 4-(3-chloropropoxy)-3-methoxybenzoate (50.0 g, 193.28 mmol, 1.00 eq.) in acetic anhydride (500 mL) in a 1-L 3-necked round-bottom flask in ice/salt bath was added concentrated $HNO_3$ (20 mL) dropwise under vigorous stirring. The resulting mixture was allowed to stir in the ice/salt bath until complete consumption of the starting material (about 30 min). The reaction mixture was diluted with 1 L of $H_2O$/ice and extracted with ethyl acetate thrice. The combined organic layers were washed with saturated aqueous sodium bicarbonate solution, brine, and dried over anhydrous sodium sulfate. Removal of the organic solvents under reduced pressure provided the desired crude product of methyl 4-(3-chloropropoxy)-5-methoxy-2-nitrobenzoate as a brown oil (60 g).

Step 3

To a rt solution of methyl 4-(3-chloropropoxy)-5-methoxy-2-nitrobenzoate (60.0 g crude, 193.28 mmol, 1.00 eq.) in CH₃CN (1 L) was added pyrrolidine (41.3 g, 580.70 mmol, 3.00 eq.), NaI (58.2 g, 2.00 eq.), potassium carbonate (66.9 g, 484.05 mmol, 2.50 eq.) and tetrabutylammonium iodide (3.57 g, 9.67 mmol, 0.05 eq.) subsequently. The resulting mixture was allowed to stir at 90° C. for 16 h. The solids were filtered off and washed with EtOAc. The filtrate was concentrated under reduced pressure to afford the desired crude product of methyl 5-methoxy-2-nitro-4-[3-(pyrrolidin-1-yl)propoxy]benzoate as a brown oil (43.2 g, 66% for 2 steps).

Step 4

To a rt solution of methyl 5-methoxy-2-nitro-4-[3-(pyrrolidin-1-yl)propoxy]benzoate (30.0 g, 88.66 mmol, 1.00 eq.) in ethyl acetate (300 mL) and water (150 mL) was added iron dust (19.9 g, 4.00 eq.) and ammonium acetate (41.0 g, 531.91 mmol, 6.00 eq.). The resulting mixture was allowed to stir in an oil bath at 100° C. for 3 h until the starting material was completely consumed, and then cooled to rt, filtered through a pad of Celite. The filtrate was concentrated under reduced pressure to remove the organic solvents. The aqueous phase was back extracted with a mixed solvent of 10% MeOH/CH₂Cl₂. Removal of the organic solvents under reduced pressure provided the desired crude product of methyl 2-amino-5-methoxy-4-[3-(pyrrolidin-1-yl)propoxy]benzoate as a brown crude oil (21.3 g, 78%).

Step 5

Into a 50-mL round-bottom flask purged with and maintained under N₂ atmosphere was added methyl 2-amino-5-methoxy-4-[3-(pyrrolidin-1-yl)propoxy]benzoate (1.00 g, 3.24 mmol, 1.00 eq.), iodobenzene (662 mg, 3.24 mmol, 1.20 eq.), Pd₂(dba)₃ (149 mg, 0.16 mmol, 0.05 eq.), Xantphos (188 mg, 0.32 mmol, 0.10 eq.), Cs₂CO₃ (3.18 g, 9.76 mmol, 3.00 eq.) and toluene (20 mL). The resulting mixture was allowed to stir at 100° C. for 16 h under N₂ atmosphere until complete consumption of the starting material. The reaction mixture was cooled to rt, diluted with 10% MeOH/CH₂Cl₂ and filtered through a pad of Celite. After removal of the organic solvents under reduced pressure, the residue was subjected to flash chromatography on 10 g silica gel column (Biotage® RSNAP Cartridge) using a mixed solvent of 10% MeOH/CH₂Cl₂ as eluent to provide the desired product of methyl 5-methoxy-2-(phenylamino)-4-[3-(pyrrolidin-1-yl)propoxy]benzoate as yellow solid (432 mg, 35%).

Step 6

Into a 50-mL round-bottom flask was added methyl 5-methoxy-2-(phenylamino)-4-[3-(pyrrolidin-1-yl)propoxy]benzoate (432 mg, 1.12 mmol, 1.00 eq.), NaOH (100 mg, 2.50 mmol, 2.22 eq.), H₂O (2 mL) and MeOH (10 mL). The resulting mixture was allowed to stir at 80° C. for 60 min. The reaction mixture was allowed to cool to rt, diluted with H₂O, neutralized with 2 N aqueous HCl to pH=7.0, and extracted with a mixed solvent of 10% MeOH/CH₂Cl₂ thrice. The combined organic layers were dried over anhydrous MgSO₄. Removal of the organic solvents under reduced pressure resulted in the desired crude product of 5-methoxy-2-(phenylamino)-4-[3-(pyrrolidin-1-yl)propoxy] benzoic acid as yellow solid (403 mg, 97%).

Step 7

Into a 50-mL round-bottom flask was added crude 5-methoxy-2-(phenylamino)-4-[3-(pyrrolidin-1-yl)propoxy] benzoic acid (403 mg, 1.09 mmol, 1.00 eq.) followed by POCl₃ (5.00 g, 32.61 mmol, 30.0 eq.). The resulted mixture was allowed to stir 100° C. for 16 h under N₂. The volatiles were removed under reduced pressure. To the residue was added H₂O and the mixture was neutralized with 1 N aqueous NaOH solution. The resulting solution was extracted with a mixed solvent of 10% MeOH/CH₂Cl₂ thrice and the organic layers were combined. Removal of the organic solvents under reduced pressure resulted in crude product of 9-chloro-2-methoxy-3-[3-(pyrrolidin-1-yl)propoxy]acridine as yellow solid (326 mg, 81%). LCMS (ES) [M+1]⁺ m/z 371.

Reference 2

Synthesis of 9-chloro-7-methoxy-6-(3-(pyrrolidin-1-yl)propoxy)-2,3-dihydro-1H-cyclopenta[b]quinolone (Intermediate II)

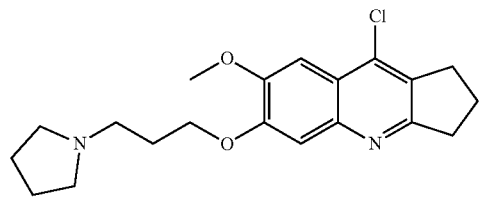 [SMILES: COc1cc2c(Cl)c3c(nc2cc1OCCCN1CCCC1)CCC3]

Step 1

To a rt solution of methyl 2-amino-5-methoxy-4-[3-(pyrrolidin-1-yl)propoxy]benzoate (5.00 g; 16.21 mmol; 1.00 eq., made in step 4, reference 1) in a mixture solvent of MeOH/THF/water (1:1:1, 25 mL) was added LiOH (0.58 g; 24.32 mmol; 1.50 eq.). This resulting mixture was allowed to stir at 60° C. for 7 h until the starting material was completely consumed, cooled to rt and treated with HOAc (1.46 g, 24.4 mmol, 1.50 eq.). After removal of solvents under reduced pressure, the residue was left under pressure overnight, and re-dissolved in 30% ⁱPrOH/chloroform. The solid was filtered off and washed with MeOH. The organic solutions were combined. Removal of the organic solvents under reduced pressure provided the desired crude product of 2-amino-5-methoxy-4-(3-(pyrrolidin-1-yl)propoxy)benzoic acid as brown syrup (5.5 g).

Step 2

To a mixture of 2-amino-5-methoxy-4-[3-(pyrrolidin-1-yl)propoxy]benzoic acid (5.50 g; 18.69 mmol; 1.00 eq.) and cyclopentanone (1.89 g; 22.42 mmol; 1.20 eq.) was added POCl₃ (15 mL). The resulting mixture was allowed to stir at 100° C. for overnight under N₂ atmosphere. The reaction mixture was cooled to rt and then slowly poured into ice/water, and neutralized with 20% aqueous NaOH solution to pH-12. The resulting mixture was extracted with a mixed solvent of 25% ⁱPrOH/Chloroform thrice and the organic layers were combined. After removal of the organic solvents under reduced pressure, the residue was purified by flash chromatography on 40 g silica gel column using 0-100% solvent A (Solvent A: 3% NH₄OH/MeOH) in solvent B (Solvent B: 0.1% NH₄OH/10% MeOH/CH₂Cl₂) as the eluent to provide the desired 9-chloro-7-methoxy-6-(3-(pyrrolidin-1-yl)propoxy)-2,3-dihydro-1H-cyclopenta[b]quinoline as brown solid (1.55 g, 23%). LCMS (ES) [M+1]+ m/z 361.

Reference 3

Synthesis of 9-chloro-7-methoxy-6-(3-(pyrrolidin-1-yl)propoxy)-1,2,3,4-tetrahydroacridine (Intermediate III)

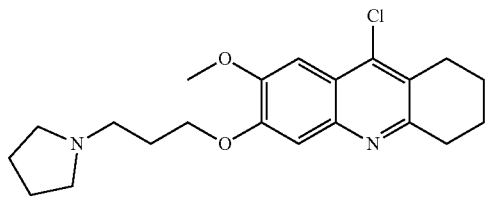 [SMILES: COc1cc2c(Cl)c3c(nc2cc1OCCCN1CCCC1)CCCC3]

To a mixture of 2-amino-5-methoxy-4-[3-(pyrrolidin-1-yl)propoxy]benzoic acid (1 500.00 mg; 5.10 mmol; 1.00 eq., made in step 1, reference 2) and cyclohexanone (600.17 mg; 6.12 mmol; 1.20 eq.) was added POCl$_3$ (5 mL). The resulting mixture was allowed to stir at 100° C. for overnight under N$_2$ atmosphere. The reaction mixture was cooled to rt and then slowly poured into ice/water, and neutralized with 20% aqueous NaOH solution to pH-12. The resulting mixture was extracted with a mixed solvent of 25% $^i$PrOH/Chloroform thrice and the organic layers were combined. After removal of the organic solvents under reduced pressure, the residue was purified by flash chromatography on 10 g silica gel column using 0-100% solvent A (solvent A: 3% NH$_4$OH/MeOH) in solvent B (solvent B: 0.1% NH$_4$OH/10% MeOH/CH$_2$Cl$_2$) as the eluent to provide the desired product of 9-chloro-7-methoxy-6-(3-(pyrrolidin-1-yl)propoxy)-1,2,3,4-tetrahydroacridine (570 mg, 29.8%).

Reference 4

Synthesis of 9-chloro-3-[3-(3-fluoropyrrolidin-1-yl)propoxy]-2-methoxyacridine (Intermediate I-1)

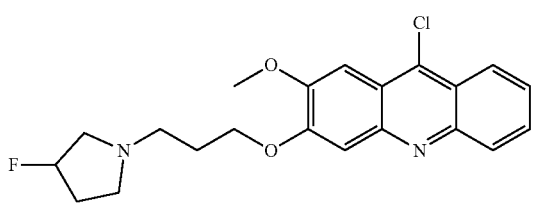 [SMILES: COc1cc2c(Cl)c3ccccc3nc2cc1OCCCN1CCC(F)C1]

The title compound was made from methyl 4-hydroxy-3-methoxybenzoate following a synthetic sequence similar as described for Intermediate I (reference 1), except that 3-fluoropyrrolidine was used in place of pyrrolidine in step 3 (100° C., 20 h). The crude final product was purified by flash chromatography on silica gel column using 0-100% solvent A (solvent A: 3% NH$_4$OH/MeOH) in solvent B (solvent B: 0.1% NH$_4$OH/10% MeOH/CH$_2$Cl$_2$) as the eluent to provide the desired product as a brown solid. LCMS (ES) [M+1]$^+$ m/z 389.1.

Reference 5

Synthesis of {3-[(9-chloro-2-methoxyacridin-3-yl)oxy]propyl}diethylamine trifluoroacetate (Intermediate I-2)

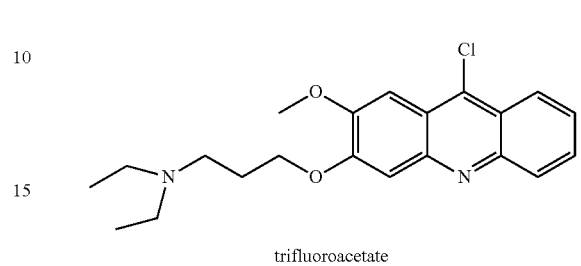

trifluoroacetate

Into a 50-mL round-bottom flask, was placed a mixture of 9-chloro-2-methoxyacridin-3-ol (180 mg, 0.71 mmol, 1.00 eq., made in Example 5, step 4), (3-chloropropyl)diethylamine hydrochloride (120 mg, 0.80 mmol, 1.20 eq.), K$_2$CO$_3$ (195 mg, 1.41 mmol, 2.00 eq.) and KI (0.23 g, 1.41 mmol, 2.00 eq.) in DMF (10 mL). The mixture was allowed to stir at 100° C. for 16 h. The crude reaction mixture was cooled to rt. The solid was filtered off through a small pad of celite. The filtrate was concentrated under reduced pressure and subjected to reverse phase preparative HPLC (Prep-C18, 20-45 μM, 120 g, Tianjin Bonna-Agela Technologies; gradient elution of 10-20% MeCN in water over a 10 min period, where both solvents contain 0.05% TFA) to provide the title compound as a white solid (0.16 g, 61%). LCMS (ES) [M+1]$^+$ m/z 373.2.

Reference 6

Synthesis of 9-chloro-2-methoxy-3-[3-(piperidin-1-yl)propoxy]acridine (Intermediate I-3)

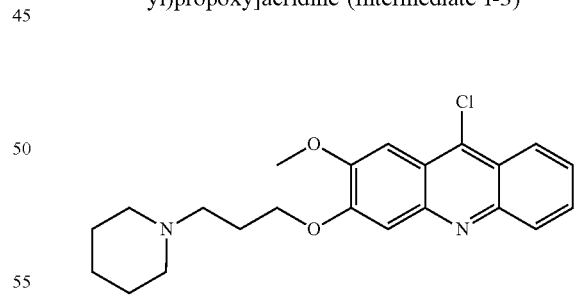

The title compound was made from methyl 4-hydroxy-3-methoxybenzoate following a synthetic sequence similar as described for the synthesis of Intermediate I (reference 1), except that piperidine was used in place of pyrrolidine in step 3 (90° C., 20 h). The crude final product was purified by flash chromatography on silica gel column using 0-100% solvent A (solvent A: 3% NH$_4$OH/MeOH) in solvent B (solvent B: 0.1% NH$_4$OH/10% MeOH/CH$_2$Cl$_2$) as the eluent to provide the desired product as a brown solid. LCMS (ES) [M+1]$^+$ m/z 385.2.

Reference 7

Synthesis of 9-chloro-3-[3-(pyrrolidin-1-yl)propoxy]acridine (Intermediate I-4)

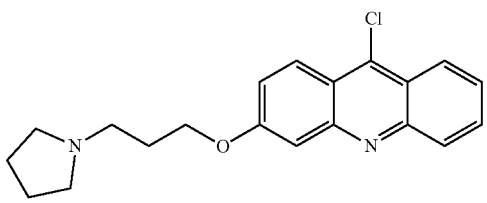 [SMILES: Clc1c2ccccc2nc2cc(OCCCN3CCCC3)ccc12]

The title compound was made from methyl 4-hydroxybenzoate following a synthetic sequence similar as described for the synthesis of Intermediate I (reference 1). The crude final product was purified by flash chromatography on silica gel column using 0-100% solvent A (solvent A: 3% $NH_4OH$/MeOH) in $CH_2Cl_2$ as the eluent to provide the desired product as a brown solid. LCMS (ES) $[M+1]^+$ m/z 341.1.

Reference 8

Synthesis of 9-chloro-2-methyl-3-[3-(pyrrolidin-1-yl)propoxy]acridine (Intermediate I-5)

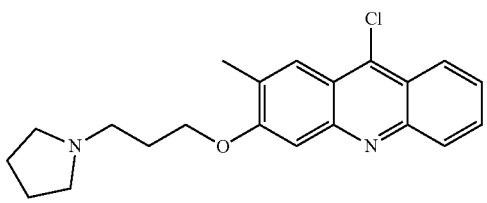 [SMILES: Cc1cc2c(Cl)c3ccccc3nc2cc1OCCCN1CCCC1]

The title compound was made from methyl 4-hydroxy-3-methylbenzoate following a synthetic sequence similar as described for the synthesis of Intermediate I (reference 1). The crude final product was purified by flash chromatography on silica gel column using 0-100% solvent A (solvent A: 3% $NH_4OH$/MeOH) in $CH_2Cl_2$ as the eluent to provide the desired product as a brown solid. LCMS (ES) $[M+1]^+$ m/z 355.1.

Reference 9

Synthesis of 2,9-dichloro-3-[3-(pyrrolidin-1-yl)propoxy]acridine (Intermediate I-6)

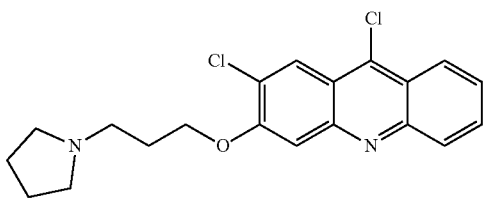 [SMILES: Clc1cc2c(Cl)c3ccccc3nc2cc1OCCCN1CCCC1]

The title compound was made from methyl 3-chloro-4-hydroxybenzoate following a synthetic sequence similar as described for the synthesis of Intermediate I (reference 1). The crude final product was purified by flash chromatography on silica gel column using 0-100% solvent A (solvent A: 3% $NH_4OH$/MeOH) in $CH_2Cl_2$ as the eluent to provide the desired product as a brown solid. LCMS (ES) $[M+1]^+$ m/z 375.1.

Reference 10

Synthesis of {3-[(9-chloro-2-mthoxyacridin-3-yl)oxy]propyl}dimethylamine trifluoroacetate (Intermediate I-7)

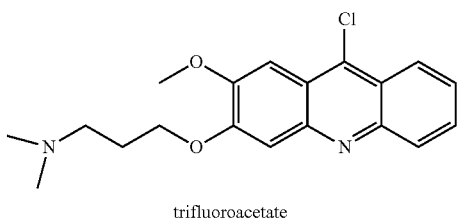 [SMILES: COc1cc2c(Cl)c3ccccc3nc2cc1OCCCN(C)C]

trifluoroacetate

The title compound was made from 9-chloro-2-methoxyacridin-3-ol (made in Example 5, step 4), following a synthetic sequence similar as described for the synthesis of Intermediate I-2 (reference 5), except that (3-chloropropyl)dimethylamine hydrochloride was used in place of (3-chloropropyl)diethylamine hydrochloride. The crude final product was purified by flash chromatography on silica gel column using 0-100% solvent A (solvent A: 3% $NH_4OH$/MeOH) in $CH_2Cl_2$ as the eluent to provide the title compound as a brown solid. LCMS (ES) $[M+1]^+$ m/z 345.2.

Reference 11

Synthesis of 9-chloro-2-methoxy-7-methyl-3-[3-(pyrrolidin-1-yl)propoxy]acridine (Intermediate I-8)

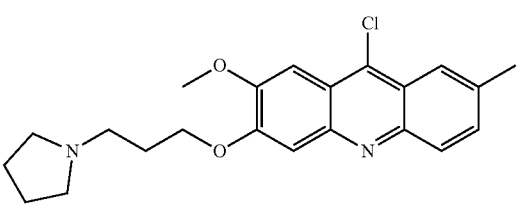 [SMILES: COc1cc2c(Cl)c3cc(C)ccc3nc2cc1OCCCN1CCCC1]

The title compound was made from methyl 4-hydroxy-3-methoxybenzoate following a synthetic sequence similar as described for the synthesis of Intermediate I (reference 1), except that 4-iodo-toulene was used in place of iodobenzene in step 5. The crude final product was purified by flash chromatography on silica gel column using 0-100% solvent A (solvent A: 3% $NH_4OH$/MeOH) in $CH_2Cl_2$ as the eluent to provide the desired product as a brown solid. LCMS (ES) $[M+1]^+$ m/z 385.2.

Reference 12

Synthesis of 9-chloro-2,7-dimethoxy-3-[3-(pyrrolidin-1-yl)propoxy]acridine (Intermediate I-9)

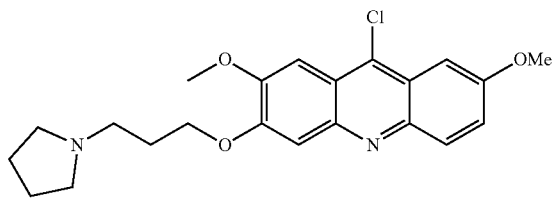 [SMILES: COc1ccc2nc3cc(OCCCN4CCCC4)c(OC)cc3c(Cl)c2c1]

The title compound was made from methyl 4-hydroxy-3-methoxybenzoate following a synthetic sequence similar as described for the synthesis of Intermediate I (reference 1), except that 4-iodoanisole was used in place of iodobenzene in step 5. The crude final product was purified by flash chromatography on silica gel column using 0-100% solvent A (solvent A: 3% NH$_4$OH/MeOH) in CH$_2$Cl$_2$ as the eluent to provide the desired product as a brown solid. LCMS (ES) [M+1]$^+$ m/z 401.1.

Reference 13

Synthesis of 1-[3-({10-chloro-8-methoxybenzo[b]1,5-naphthyridin-7-yl}oxy)propyl]pyrrolidine (Intermediate I-10)

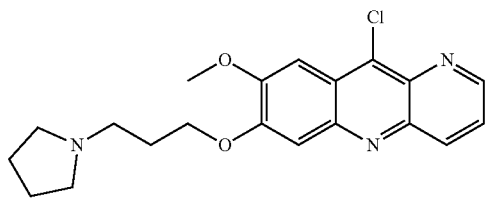 [SMILES: COc1cc2c(Cl)c3ncccc3nc2cc1OCCCN1CCCC1]

Step 1

Into a 250-mL round-bottom flask was placed a mixture of 2-methoxy-5-nitrophenol (5.00 g, 29.56 mmol, 1.00 eq.), N,N-dimethylformamide (60 mL), potassium carbonate (8.10 g, 58.61 mmol, 2.00 eq.) and 1-(3-chloropropyl)pyrrolidine (5.99 g, 40.57 mmol, 1.10 eq.). The resulting mixture was allowed to stir at 80° C. for 12 h. The reaction mixture was cooled to rt, diluted with H$_2$O and extracted with ethyl acetate thrice. The combined organic layers were dried over anhydrous sodium sulfate and concentrated under reduced pressure. The residue was purified by flash chromatography on silica gel column with 10% MeOH/CH$_2$Cl$_2$ as the eluent to provide 1-[3-(2-methoxy-5-nitrophenoxy)propyl]pyrrolidine as a yellow oil (4.80 g, 58%). LCMS (ES) [M+1]$^+$ m/z 281.1.

Step 2

Into a 250-mL round-bottom flask, was placed a mixture of 1-[3-(2-methoxy-5-nitrophenoxy)-propyl]pyrrolidine (4.80 g, 17.12 mmol, 1.00 eq.), methanol (100 mL) and 10% Pd/C (500 mg). The flask was degassed and purged with H$_2$ for 5 times. The mixture was allowed to stir at rt for 4 h under H$_2$ atmosphere, and the solid was filtered off. Removal of the organic solvents under reduced pressure provided crude product of 4-methoxy-3-[3-(pyrrolidin-1-yl)propoxy]aniline as a tan oil (4.10 g, 96%). LCMS (ES) [M+1]$^+$ m/z 251.2.

Step 3

Into a 100 mL round-bottom flask purged and maintained with an inert atmosphere of nitrogen, was placed a mixture of 4-methoxy-3-[3-(pyrrolidin-1-yl)propoxy]aniline (1.80 g, 7.2 mmol, 1.00 eq.), dioxane (60 mL), methyl 3-bromopyridine-2-carboxylate (1.51 g, 7.2 mmol, 1.00 eq.), Xantphos (208 mg, 0.36 mmol, 0.05 eq.), Cs$_2$CO$_3$ (4.7 g, 14.4 mmol, 2.00 eq.) and Pd(OAc)$_2$ (80 mg, 0.36 mmol, 0.05 eq.). The resulting mixture was stirred at 100° C. for 16 h and then cooled to rt. The solid was filtered off through a small pad of celite, and the filtrate was concentrated under reduced pressure. The resulting residue was purified by flash column chromatography on silica gel using 13% MeOH/CH$_2$Cl as the eluent to provide methyl 3-([4-methoxy-3-[3-(pyrrolidin-1-yl)propoxy]phenyl]amino)pyridine-2-carboxylate as a yellow solid (1.21 g, 44%). LCMS (ES) [M+1]$^+$ m/z 386.2.

Step 4

Into a 25-mL round-bottom flask, was placed a mixture of methyl 3-([4-methoxy-3-[3-(pyrrolidin-1-yl)propoxy]phenyl]amino)pyridine-2-carboxylate (1.2 g, 3.11 mmol, 1.00 eq.), methanol (12 mL), water (3 mL) and sodium hydroxide (249 mg, 6.3 mmol, 2.00 eq.). The resulting solution was stirred at 60° C. for 16 h. The solution was concentrated under reduced pressure. The residue was diluted with water (5 mL) and acidified with aqueous HCl (1.0 N) to pH 6~7. The mixture was extracted with 10% MeOH/CH$_2$Cl$_2$ thrice. The combined organic layers were dried over anhydrous sodium sulfate and concentrated under reduced pressure to provide 3-([4-methoxy-3-[3-(pyrrolidin-1-yl)propoxy]phenyl]amino)pyridine-2-carboxylic acid as a yellow solid (0.98 g, 85%). LCMS (ES) [M+1]$^+$ m/z 372.2.

Step 5

The title compound was made from 3-([4-methoxy-3-[3-(pyrrolidin-1-yl)propoxy]phenyl]amino)pyridine-2-carboxylic acid following a procedure similar as described for the synthesis of Intermediate I (step 7, reference 1). The crude final product was purified by flash chromatography on silica gel column using 0-100% solvent A (solvent A: 3% NH$_4$OH/MeOH) in CH$_2$Cl$_2$ as the eluent to provide the title compound as a yellow solid (0.49 g, 50%). LCMS (ES) [M+1]$^+$ m/z 372.1.

Reference 14

Synthesis of 9-chloro-5-fluoro-2-methoxy-3-[3-(pyrrolidin-1-yl)propoxy]acridine (Intermediate I-11)

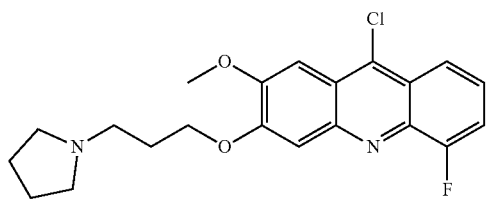 [SMILES: COc1cc2c(Cl)c3cccc(F)c3nc2cc1OCCCN1CCCC1]

The title compound was made from 2-methoxy-5-nitrophenol following a synthetic sequence similar as described for the synthesis of Intermediate I-10 (reference 13), except that ethyl 2-bromo-3-fluorobenzoate was used in place of methyl 3-bromopyridine-2-carboxylate in step 3. The crude final product was purified by flash chromatography on silica gel column using 0-100% solvent A (solvent A: 3% NH$_4$OH/MeOH) in CH$_2$Cl$_2$ as the eluent to provide the title compound product as an off-white solid. LCMS (ES) [M+1]$^+$ m/z 389.1.

Reference 15

Synthesis of 1-[3-({5-chloro-7-methoxybenzo[b]1,8-naphthyridin-8-yl}oxy)propyl]pyrrolidine (Intermediate I-12)

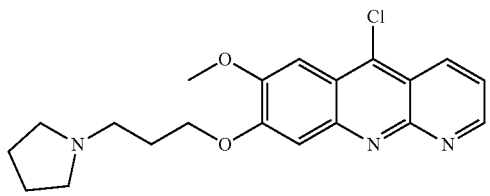 [SMILES: COc1cc2c(Cl)c3cccnc3nc2cc1OCCCN1CCCC1]

The title compound was made from 2-methoxy-5-nitrophenol following a synthetic sequence similar as described for the synthesis of Intermediate I-10 (reference 13), except that ethyl 2-chloronicotinate was used in place of methyl 3-bromopyridine-2-carboxylate in step 3. The crude final product was purified by flash chromatography on silica gel column using 0-100% solvent A (solvent A: 3% NH$_4$OH/MeOH) in CH$_2$Cl$_2$ as the eluent to provide the title product as a dark syrup. LCMS (ES) [M+1]$^+$ m/z 372.1.

Reference 16

Synthesis of 1-[3-({10-chloro-8-methoxybenzo[b]1,6-naphthyridin-7-yl}oxy)propyl]pyrrolidine (Intermediate I-13)

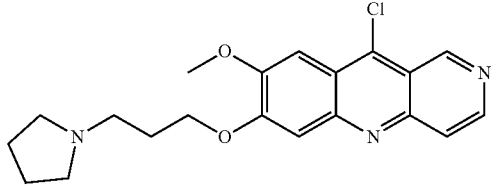 [SMILES: COc1cc2c(Cl)c3cnccc3nc2cc1OCCCN1CCCC1]

The title compound was made from 2-methoxy-5-nitrophenol following a synthetic sequence similar as described for the synthesis of Intermediate I-10 (reference 13), except that ethyl 4-chloronicotinate was used in place of methyl 3-bromopyridine-2-carboxylate in step 3. The crude final product was purified by flash chromatography on silica gel column using 0-100% solvent A (solvent A: 3% NH$_4$OH/MeOH) in CH$_2$Cl$_2$ as the eluent to provide the title product as a brown solid. LCMS (ES) [M+1]$^+$ m/z 372.1.

Reference 17

Synthesis of 9-chloro-1-fluoro-7-methoxy-6-[3-(pyrrolidin-1-yl)propoxy]acridine (Intermediate I-14)

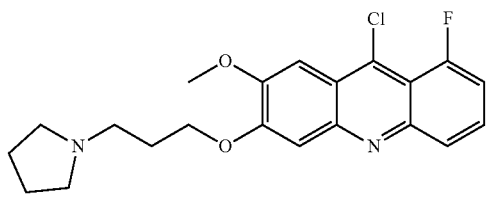 [SMILES: COc1cc2c(Cl)c3c(F)cccc3nc2cc1OCCCN1CCCC1]

The title compound was made from 2-methoxy-5-nitrophenol following a synthetic sequence similar as described for the synthesis of Intermediate I-10 (reference 13), except that methyl 2-bromo-6-fluorobenzoate was used in place of methyl 3-bromopyridine-2-carboxylate in step 3. The crude final product was purified by flash chromatography on silica gel column using 0-100% solvent A (solvent A: 3% NH$_4$OH/MeOH) in CH$_2$Cl$_2$ as the eluent to provide the title compound product as brown solid. LCMS (ES) [M+1]$^+$ m/z 389.1.

Reference 18

Synthesis of 9-chloro-2-methoxy-3-[3-(morpholin-4-yl)propoxy]acridine (Intermediate I-15)

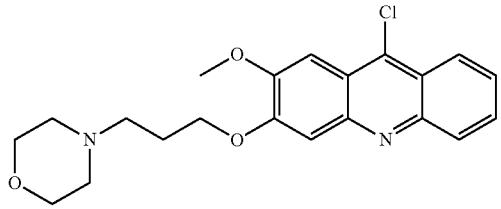 [SMILES: COc1cc2c(Cl)c3ccccc3nc2cc1OCCCN1CCOCC1]

The title compound was made from 9-chloro-2-methoxyacridin-3-ol (made in Example 5, step 4), following a synthetic sequence similar as described for the synthesis of Intermediate I-2 (reference 5), except that 4-(3-chloropropyl)morpholine hydrochloride was used in place of (3-chloropropyl)diethylamine hydrochloride. The crude final product was purified by flash chromatography on silica gel column using 0-100% solvent A (solvent A: 3% NH$_4$OH/MeOH) in CH$_2$Cl$_2$ as the eluent to provide the title compound as a brown solid LCMS (ES) [M+1]$^+$ m/z 387.1

Synthesis of Exemplary Compounds of Formula (I)

Example 1

Synthesis of 2-methoxy-N-methyl-3-[3-(pyrrolidin-1-yl)propoxy]acridin-9-amine

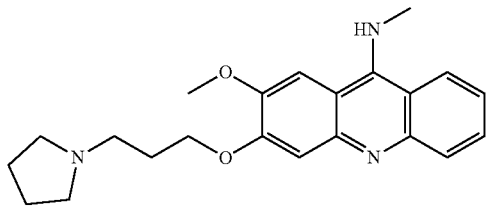 [SMILES: CNc1c2ccccc2nc2cc(OCCCN3CCCC3)c(OC)cc12]

Into a 100-mL pressure tank reactor was added crude 9-chloro-2-methoxy-3-[3-(pyrrolidin-1-yl)propoxy]acridine (320 mg, 0.86 mmol, 1.00 eq., Intermediate I) and $CH_3NH_2$ (15 mL, 30% in EtOH). The reaction vessel was sealed and the mixture was allowed to stir 130° C. for 4 h and then cooled to rt. After removal of the organic solvents under reduced pressure, the residue was dissolved in 3 mL of N,N-dimethylformamide, filtered and then subjected for purification on reverse preparative HPLC (Prep-C18, 5 μM OBD column, 19×250 mm, SunFire; gradient elution of 40% MeCN in water to 48% MeCN in water over 7 min, where both solvents contain 0.05% TFA, flow rate: 20 mL/min, detector UV wavelength: 254 nm). The desired HPLC fractions were concentrated under reduced pressure. The residue was treated with 10 mL of 20% aqueous sodium carbonate solution, extracted with a mixed solvent of 10% $MeOH/CH_2Cl_2$ five times. The combined organic layers were concentrated under reduced pressure and lyophilized to afford the title compound as orange solid (95.6 mg, 30%). LCMS (ES) $[M+1]^+$ m/z 366.5.

Example 2

Synthesis of 2-methoxy-N-(1-methylpiperidin-4-yl)-3-[3-(pyrrolidin-1-yl)propoxy]acridin-9-amine trifluoroacetate

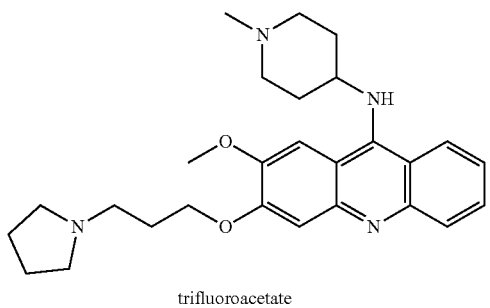 [SMILES: COc1cc2c(NC3CCN(C)CC3)c3ccccc3nc2cc1OCCCN1CCCC1]

trifluoroacetate

To a 8 mL vial was added 9-chloro-2-methoxy-3-[3-(pyrrolidin-1-yl)propoxy]acridine (300 mg, 0.81 mmol, 1.00 eq., Intermediate I), n-BuOH (3 mL), 1-methylpiperidin-4-amine (924 mg, 8.09 mmol, 10.00 eq.) and diisopropylethylamine (523 mg, 4.05 mmol, 5.00 eq.). The resulting mixture was allowed to stir at 120° C. for 48 h. After removal of the organic solvents under reduced pressure, the residue was dissolved in 3 mL of N,N-dimethylformamide, filtered and then subjected for purification on reverse preparative HPLC (Prep-C18, 5 μM OBD column, 19×250 mm, SunFire; gradient elution of 3-28% MeCN in water over 7 min, where both solvents contain 0.05% trifluoroacetic acid, flow rate: 20 mL/min, detector UV wavelength: 254 nm) to provide the title compound as a brown solid (188.2 mg, 29%). LCMS (ES) $[M+1]^+$ m/z 449.3.

Example 3

Synthesis of 2-methoxy-N-[1-(propan-2-yl)piperidin-4-yl]-3-[3-(pyrrolidin-1-yl)propoxy]acridin-9-amine trifluoroacetate

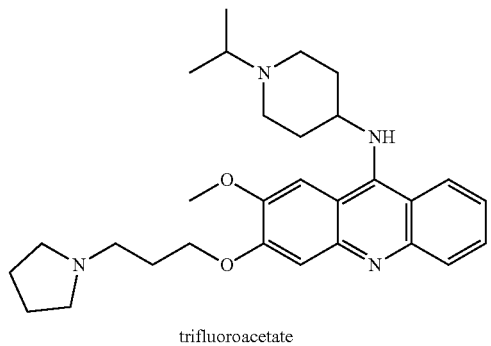 [SMILES: COc1cc2c(NC3CCN(C(C)C)CC3)c3ccccc3nc2cc1OCCCN1CCCC1]

trifluoroacetate

To a 8 mL vial was added 9-chloro-2-methoxy-3-[3-(pyrrolidin-1-yl)propoxy]acridine (300 mg, 0.81 mmol, 1.00 eq., Intermediate I), n-BuOH (3 mL), 1-(propan-2-yl)piperidin-4-amine (1.15 g, 8.08 mmol, 10.00 eq.) and diisopropylethylamine (523 mg, 4.05 mmol, 5.00 eq.) subsequently. The vial was sealed, and the resulting mixture was allowed to stir at 120° C. for 48 h. After removal of the organic solvents under reduced pressure, the residue was dissolved in 3 mL of DMF, filtered and then subjected for purification on reverse preparative HPLC (Prep-C18, 5 μM OBD column, 19×250 mm, SunFire; gradient elution of 3-28% MeCN in water over 7 min, where both solvents contain 0.05% trifluoroacetic acid, flow rate: 20 mL/min, detector UV wavelength: 254 nm) to provide the title compounds as a yellow solid (223.7 mg, 34%). LCMS (ES) $[M+1]^+$ m/z 477.4.

Example 4

Synthesis of 7-methoxy-N-(propan-2-yl)-6-[3-(pyrrolidin-1-yl)propoxy]-1H,2H,3H-cyclopenta[b]quinolin-9-amine formate

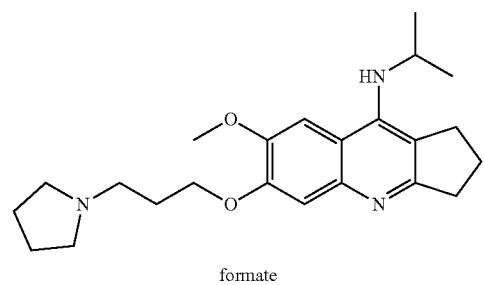 [SMILES: COc1cc2c(NC(C)C)c3c(nc2cc1OCCCN1CCCC1)CCC3]

formate

Into a microwave reaction vial (10 mL) was added 9-chloro-7-methoxy-6-(3-(pyrrolidin-1-yl)propoxy)-2,3-dihydro-1H-cyclopenta[b]quinolone (Intermediate II) (50.00 mg; 0.14 mmol; 1.00 eq.), sodium 2-methyl-2-propanolate (40 mg, 0.42 mmol; 3.00 eq.) followed by 1,4-dioxane (3.0 mL). The resulting mixture was purged with $N_2$ for 5 min. To the solution was added 3rd Generation BrettPhos precatalyst (17 mg, 0.01 mmol, 0.10 eq.) followed by propan-2-amine (45 mg, 0.7 mmol, 5.0 eq.). The vial was sealed and subjected to a microwave reactor (120° C., 2 h). The resulting reaction mixture was cooled to rt and the volatiles were removed under reduced pressure. The residue was re-dissolved in 25% $^i$PrOH/CHCl$_3$ and washed with water. After removal of the organic solvents under reduced pressure, the residue was dissolved in DMSO (4 mL), filtered and subjected for purification on reverse preparative HPLC (Prep-C18, 5 uM OBD column, 19×250 mm, waters; gradient elution of 0-40% MeCN in water over a 20 min period, where water contain 0.1% formic acid, flow rate: 20 mL/min, detector UV wavelength: 254 nm) to provide the title compound as a brown syrup (29 mg, 50%). LCMS (ES) [M+1]$^+$ m/z 384.2.

Example 5

Synthesis of 2-methoxy-N-methyl-3-[(1-methylpyrrolidin-3-yl)methoxy]acridin-9-amine trifluoroacetate

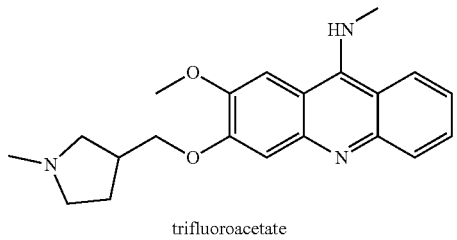 [SMILES: CNc1c2ccccc2nc2cc(OCC3CCN(C)C3)c(OC)cc12]

trifluoroacetate

Step 1

Into a 500-mL round-bottom flask, was placed a mixture of methyl 4-(benzyloxy)-5-methoxy-2-nitrobenzoate (15.00 g, 47.27 mmol, 1.00 eq.), MeOH (150 mL) and 10% Pd/C (3.00 g). The mixture was degassed and purged with hydrogen for 3 times. The resulting mixture was allowed to stir at 25° C. for 16 h. The solids were filtered out. The filtrate was concentrated under reduced pressure to provide crude product of methyl 2-amino-4-hydroxy-5-methoxybenzoate as a gray solid (8.5 g, 91%). LCMS (ES) [M+1]$^+$ m/z 198.1.

Step 2

Into a 250-mL round-bottom flask, was placed a mixture of methyl 2-amino-4-hydroxy-5-methoxybenzoate (5.00 g, 25.36 mmol, 1.00 eq.), toluene (100 mL), iodobenzene (6.20 g, 30.39 mmol, 1.20 eq.), Pd$_2$(dba)$_3$ (1.31 g, 1.27 mmol, 0.05 eq.), Xantphos (1.47 g, 2.54 mmol, 0.10 eq.) and Cs$_2$CO$_3$ (24.80 g, 76.12 mmol, 3.00 eq.). The resulting mixture was stirred for 16 h at 100° C. under $N_2$. The mixture was concentrated under reduced pressure. The residue was diluted with ethyl acetate (200 mL), washed with water (2×100 mL) and concentrated under reduced pressure. The residue was purified by reverse phase preparative MPLC (Prep-C18, 20-45 μM, 120 g, Tianjin Bonna-Agela Technologies; gradient elution of 40% MeCN in water to 50% MeCN in water over a 10 min period, where both solvents contain 0.05% TFA) to provide methyl 4-hydroxy-5-methoxy-2-(phenylamino)benzoate as a gray solid (2.1 g, 32%). LCMS (ES) [M+1]$^+$ m/z 274.1.

Step 3

Into a 50-mL round-bottom flask, was placed a mixture of methyl 4-hydroxy-5-methoxy-2-(phenylamino)benzoate (2.00 g, 7.32 mmol, 1.00 eq.), methanol (10 mL) and lithium hydroxide monohydrate (0.60 g, 14.65 mmol, 2.00 eq.) in water (10 mL). The resulting solution was stirred for 6 h at 50° C. The mixture was concentrated under reduced pressure, diluted with water (10 mL) and acidified with 1 M HCl aqueous solution (pH ~6). The solids were collected by filtration to provide crude product of 4-hydroxy-5-methoxy-2-(phenylamino)benzoic acid as a gray solid (1.60 g, 84%).

Step 4

Into a 50-mL round-bottom flask, was placed 4-hydroxy-5-methoxy-2-(phenylamino)benzoic acid (1.5 g, 5.79 mmol, 1.00 eq.) and POCl$_3$ (20 mL). The resulting solution was stirred at 80° C. for 4 h. The mixture was concentrated under reduced pressure and then quenched by the addition of water (100 mL). The mixture was basified with 2.0 M sodium carbonate aqueous solution (pH ~6). The mixture was extracted with 10% MeOH/CH$_2$Cl$_2$ thrice, and the combined organic layers were concentrated and purified by silica gel column eluted with ethyl acetate to provide 9-chloro-2-methoxyacridin-3-ol as a gray solid (1.20 g, 80%).

Step 5

Into a 50-mL round-bottom flask, was placed a mixture of tert-butyl 3-(bromomethyl)pyrrolidine-1-carboxylate (230 mg, 0.87 mmol, 1.00 eq.), DMF (10 mL), 9-chloro-2-methoxyacridin-3-ol (226 mg, 0.87 mmol, 1.00 eq.), potassium carbonate (240 mg, 1.74 mmol, 2.00 eq.) and KI (290 mg, 1.74 mmol, 2.00 eq.). The resulting mixture was stirred at 100° C. for 16 h. The mixture was diluted with water (50 mL) and extracted with ethyl acetate thrice. The combined organic layers were dried over anhydrous sodium sulfate and concentrated under reduced pressure. The residue was purified by column chromatography on silica gel eluted with ethyl acetate/petroleum ether (1/2) to provide tert-butyl 3-[[(9-chloro-2-methoxyacridin-3-yl)oxy]methyl]pyrrolidine-1-carboxylate as a yellow solid. LCMS (ES) [M+1]$^+$ m/z 443.2.

Step 6

Into a 50-mL sealed tube, was placed a mixture of tert-butyl 3-[[(9-chloro-2-methoxyacridin-3-yl)oxy]methyl]pyrrolidine-1-carboxylate (340 mg, 0.77 mmol, 1.00 eq.) and methanamine (20 mL, 1.0 M in EtOH). The resulting solution was sealed and was allowed to stir at 80° C. for 4 h. The mixture was concentrated under reduced pressure to provide tert-butyl 3-((2-methoxy-9-(methylamino)acridin-3-yloxy)methyl)pyrrolidine-1-carboxylate as a yellow solid (360 mg, crude). LCMS (ES) [M+1]$^+$ m/z 438.3.

Step 7

To a solution of tert-butyl 3-([[2-methoxy-9-(methylamino)acridin-3-yl]oxy]methyl)pyrrolidine-1-carboxylate (300 mg, 0.69 mmol, 1.00 eq.) in CH$_2$Cl$_2$ (10 mL) was added a solution of dioxane (10 mL) saturated with HCl (gas). The resulting solution was stirred at rt for 4 h. The mixture was concentrated under reduced pressure to provide 2-methoxy-N-methyl-3-(pyrrolidin-3-ylmethoxy)acridin-9-amine hydrochloride salt (240 mg) as a light yellow solid. LCMS (ES) [M+1]$^+$ m/z 338.2.

Step 8

Into a 25-mL round-bottom flask, was placed a mixture of 2-methoxy-N-methyl-3-(pyrrolidin-3-ylmethoxy)acridin-9-amine hydrochloride (100 mg, 0.30 mmol, 1.00 eq.), methanol (5 mL), formaldehyde (1 mL, 30%/W in H$_2$O), TEA (150 mg, 1.50 mmol, 5.00 eq.) and NaBH₃CN (56 mg, 0.90 mmol, 3.00 eq.). The resulting solution was allowed to stir at rt for 4 h. The mixture was concentrated under reduced pressure. The residue was dissolved in DMF (5 mL), filtered and subjected to reverse phase preparative HPLC (Prep-C18, 5 μM SunFire column, 19×150 mm, Waters; gradient elution of 30-40% MeCN in water over a 10 min period, where both solvents contain 0.1% TFA) to provide the title compound as a yellow solid (6.6 mg, 4%). LCMS (ES) [M+1]⁺ m/z 352.3.

Example 6

Synthesis of 2-methoxy-N-methyl-3-[(1-methylpiperidin-3-yl)methoxy]acridin-9-amine trifluoroacetate

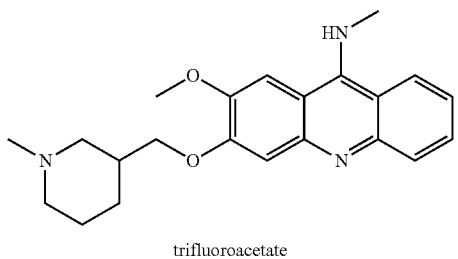 [SMILES: CNc1c2ccccc2nc2cc(OCC3CCCN(C)C3)c(OC)cc12]

trifluoroacetate

The title compound was made from methyl 4-(benzyloxy)-5-methoxy-2-nitrobenzoate following a procedure similar as described for Example 5, except that tert-butyl 3-(bromomethyl)piperidine-1-carboxylate was used in place of tert-butyl 3-(bromomethyl)pyrrolidine-1-carboxylate (step 5). The crude final product was purified by reverse phase preparative HPLC (Prep-C18, 5 μM SunFire column, 19×150 mm, Waters; gradient elution of 30-40% MeCN in water over a 10 min period, where both solvents contain 0.1% TFA) to provide the title compound as a yellow solid. LCMS (ES) [M+1]⁺ m/z 366.2.

Example 7

Synthesis of 2-methoxy-3-[(1-methylpyrrolidin-3-yl)methoxy]-N-(oxan-4-yl)acridin-9-amine formate

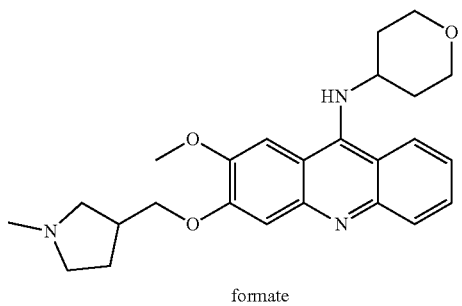 [SMILES: COc1cc2c(NC3CCOCC3)c3ccccc3nc2cc1OCC1CCN(C)C1]

formate

The title compound was made from methyl 4-(benzyloxy)-5-methoxy-2-nitrobenzoate following a procedure similar as described for Example 5, except that tetrahydro-2H-pyran-4-amine was used in place of methanamine (step 6). The crude final product was purified by reverse phase preparative HPLC (Prep-C18, 5 μM SunFire column, 19×150 mm, Waters; gradient elution of 30-40% MeCN in water over a 10 min period, where both solvents contain 0.05% formic acid) to provide the title compound as a brown solid. LCMS (ES) [M+1]⁺ m/z. 422.2.

Example 8

Synthesis of 2-ethoxy-N-methyl-3-[3-(pyrrolidin-1-yl)propoxy]acridin-9-amine formate and 3-ethoxy-N-methyl-2-[3-(pyrrolidin-1-yl)propoxy]acridin-9-amine formate (1:1)

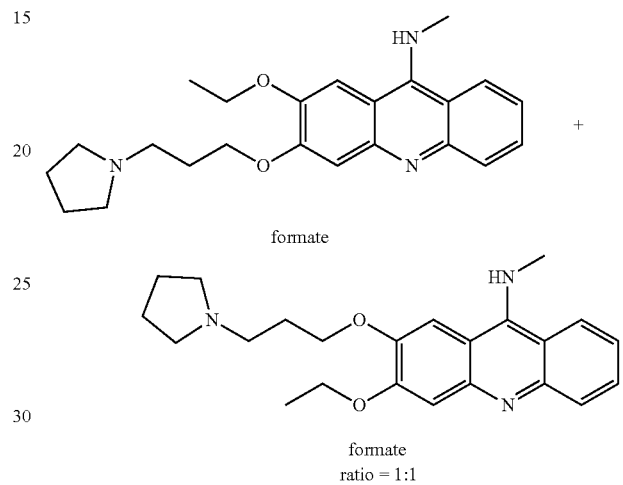

formate
ratio = 1:1

Step 1

Into a 100-mL round-bottom flask purged and maintained with an inert atmosphere of nitrogen, was placed a solution of 9-chloro-2-methoxyacridin-3-ol (1.89 g, 7.30 mmol, 1.00 eq., made in Example 5, step 4) in CH₂Cl₂ (40 mL). This was followed by the addition of BBr₃ (21.9 mL, 1.0 M in CH₂Cl₂, 21.90 mmol, 3.00 eq.) at −78° C. over 5 min. The resulting solution was allowed to warm to rt and to stir at rt for 16 h. The resulting reaction mixture was quenched with water (50 mL) and extracted with 10% MeOH/CH₂Cl₂ thrice. The combined organic layers were dried over anhydrous sodium sulfate and concentrated under reduced pressure. The residue was purified by column chromatography on silica gel eluted with ethyl acetate/petroleum ether (2/1) to provide 9-chloroacridine-2, 3-diol as a yellow solid (1.30 g, 37%). LCMS (ES) [M+1]⁺ m/z 246.1.1

Step 2

To a solution of 9-chloroacridine-2, 3-diol (1.30 g, 5.29 mmol, 1.00 eq.) and sodium hydroxide (212 mg, 5.29 mmol, 1.00 eq.) in water (30 mL) was added Et₂SO₄ (0.80 g, 5.29 mmol, 1.00 eq.) dropwise. The resulting mixture was stirred at 50° C. for 16 h. The mixture was diluted with H₂O (20 mL) and extracted with ethyl acetate thrice. The combined organic layers were dried over anhydrous sodium sulfate and concentrated under reduced pressure. The residue was purified by column chromatography on silica gel eluted with ethyl acetate/petroleum ether (1/2) to provide a mixture of 9-chloro-2-ethoxyacridin-3-ol and 9-chloro-3-ethoxyacridin-2-olas as a yellow solid (520 mg, 36%). LCMS (ES) [M+1]⁺ m/z 274.1

Step 3

Into a 50-mL round-bottom flask, was placed a mixture of 9-chloro-2-ethoxyacridin-3-ol and 9-chloro-3-ethoxyacridin-2-ol (520 mg, 1.90 mmol, 1.00 eq.), CH$_3$CN (30 mL), 1-(3-chloropropyl)pyrrolidine hydrochloride (350 mg, 1.90 mol, 1.00 eq.) and Cs$_2$CO$_3$ (1.24 g, 3.80 mmol, 2.00 eq.). The resulting mixture was stirred for 2 h at 80° C. The solids were filtered off, and the filter cake was washed with CH$_3$CN twice The filtrate was concentrated under reduced pressure and purified by column chromatography on silica gel eluted with MeOH/DCM (1/10) to provide a mixture of 9-chloro-2-ethoxy-3-[3-(pyrrolidin-1-yl)propoxy]acridine and 9-chloro-3-ethoxy-2-[3-(pyrrolidin-1-yl)propoxy]acridine as a yellow solid (200 mg, 27%). LCMS (ES) [M+1]$^+$ m/z 385.2.

Step 4

Into a 40-mL sealed tube, was placed mixture of 9-chloro-2-ethoxy-3-[3-(pyrrolidin-1-yl)propoxy]acridine and 9-chloro-3-ethoxy-2-[3-(pyrrolidin-1-yl)propoxy]acridine (200 mg, 0.52 mmol, 1.00 eq.), DMSO (5 mL), methanamine hydrochloride (176 mg, 2.60 mmol, 5.00 eq.) and K$^t$OBu (116 mg, 1.04 mmol, 2.00 eq.). The resulting mixture was allowed to stir for 16 h at 100° C. The crude reaction mixture was filtered and subjected to reverse preparative HPLC (Prep-C18, 5 μM XBridge column, 19×150 mm, Waters; gradient elution of 23-35% MeCN in water over a 7 min period, where both solvents contain 0.1% formic acid) to provide the title compounds as a 1:1 mixture and as a yellow solid (20.9 mg, 11%). LCMS (ES) [M+1]$^+$ m/z 380.4.

Example 9

Synthesis of 2-methoxy-3-[3-(pyrrolidin-1-yl)propoxy]acridin-9-ol formate

Into a 40-mL vial, was placed a mixture of 9-chloro-2-methoxy-3-[3-(pyrrolidin-1-yl)propoxy]acridine (Intermediate I, 200 mg, 0.54 mmol, 1.00 eq), water (1.0 mL), ethanol (5.0 mL) and sodium hydroxide (108 mg, 2.70 mmol, 5.00 eq). The resulting solution was stirred for 16 h at 90° C. in an oil bath. After being cooled to room temperature, the mixture was concentrated under vacuum. The residue was diluted with 3 mL of DMF and the pH value of the solution was adjusted to 7 with 2N aqueous hydrogen chloride solution. The mixture was subjected to reverse preparative HPLC (Prep-C18, 5 μM XBridge column, 19×150 mm, Waters; gradient elution of 30-55% MeCN in water over a 7 min period, where both solvents contain 0.1% formic acid) to provide the title compound as a yellow solid (23.9 mg, 13%). LCMS (ES) [M+1]$^+$ m/z 353.3.

Example 10

Synthesis of 9-ethoxy-2-methoxy-3-[3-(pyrrolidin-1-yl)propoxy]acridine formate formate Into a 40-mL vial, was placed a mixture of 9-chloro-2-methoxy-3-[3-(pyrrolidin-1-yl)propoxy]acridine (Intermediate I, 200 mg, 0.54 mmol, 1.00 equiv), sodium hydroxide (108 mg, 2.70 mmol, 5.00 equiv), water (1.0 mL) and ethanol (5.0 mL). The resulting solution was stirred for 16 h at 90° C. in an oil bath. The mixture was concentrated under vacuum, and the residue was dissolved in DMF (5 mL) and purified by reverse preparative HPLC (Prep-C18, 5 μM XBridge column, 19×150 mm, Waters; gradient elution of 32-60% MeCN in water over a 6.5 min period, where both solvents contain 0.1% formic acid) to provide the title compound as a white solid (21.4 mg, 9%). LCMS (ES) [M+1]$^+$ m/z 381.3.

Example 11

Synthesis of 7-methoxy-6-[3-(pyrrolidin-1-yl)propoxy]-1H,2H,3H-cyclopenta[b]quinolin-9-amine formate

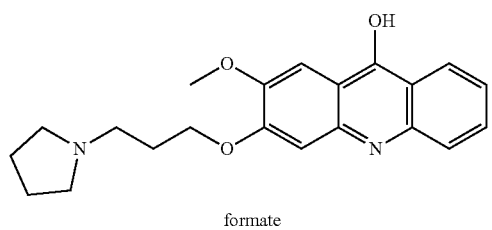 [SMILES: COc1cc2c(O)c3ccccc3nc2cc1OCCCN1CCCC1]

formate

Step 1

Into a microwave reaction vial (10 mL) was added 9-chloro-7-methoxy-6-(3-(pyrrolidin-1-yl)propoxy)-2,3-dihydro-1H-cyclopenta[b]quinolone (Intermediate II) (50.00 mg; 0.14 mmol; 1.00 eq.), sodium 2-methyl-2-propanolate (40 mg, 0.42 mmol; 3.00 eq.) followed by 1,4-dioxane (3.0 mL). The resulting mixture was purged with N$_2$ for 5 min. To the solution was added 3rd Generation BrettPhos precatalyst (17 mg, 0.01 mmol, 0.10 eq.) followed by (4-methoxyphenyl)methanamine (95 mg, 0.7 mmol, 5.0 eq.). The vial was sealed and subjected to a microwave reactor (120° C., 2 h). The resulting reaction mixture was cooled to rt, and the volatiles were removed under reduced pressure. The residue was re-dissolved in 25% $^i$PrOH/CHCl$_3$ and washed with water. Removal of the organic solvents under reduced pressure provided the crude product of 7-methoxy-N-[(4-methoxyphenyl)methyl]-6-[3-(pyrrolidin-1-yl)propoxy]-1H,2H,3H-cyclopenta[b]quinolin-9-amine (58 mg). LCMS (ES) [M+1]+ m/z 462.3.

Step 2

A solution of 7-methoxy-N-[(4-methoxyphenyl)methyl]-6-[3-(pyrrolidin-1-yl)propoxy]-1H,2H,3H-cyclopenta[b]quinolin-9-amine (58 mg, 0.13 mmol, 1.0 eq) in a 30% TFA/CH₂Cl₂ (2 mL) was sealed and allowed to stir at 55° C. for 1 hr. The resulting mixture was cooled to rt. After removal of the organic solvents under reduced pressure, the residue was dissolved in DMSO (1.5 mL). The solution was filtered and subjected for purification on reverse preparative HPLC (Prep-C18, 5 M OBD column, 19×250 mm, SunFire; gradient elution of 25-48% MeCN in water over 7 min, where both solvents contain 0.05% TFA, flow rate: 20 mL/min, detector UV wavelength: 254 nm) to provide the title compound as a yellow solid (6 mg, 13%). LCMS (ES) [M+1]+ m/z 342.2.

Example 12

Synthesis of 7-methoxy-6-[3-(pyrrolidin-1-yl)propoxy]-1,2,3,4-tetrahydroacridine formate

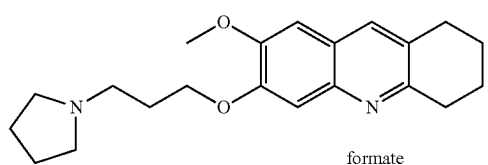 [SMILES: COc1cc2cc3c(nc2cc1OCCCN1CCCC1)CCCC3]

formate

To a solution of 9-chloro-2-methoxy-3-[3-(pyrrolidin-1-yl)propoxy]acridine (Intermediate I) (35.00 mg; 0.09 mol) in MeOH (3 mL) was added Pd/C (10 mg). The reaction flask was purged with H₂ for 12 min. After stirring under H₂ atmosphere at rt for 1.0 h, the solid was filtered off through a small pad of celite. After removal of the organic solvents under reduced pressure, the residue was dissolved in DMSO (0.4 mL), filtered and subjected for purification on reverse preparative HPLC (Prep-C18, 5 μM OBD column, 19×250 mm, waters; gradient elution of 0-40% MeCN in water over a 20 min period, where water contain 0.1% formic acid, flow rate: 20 mL/min, detector UV wavelength: 254 nm) to provide the title compound as a brown syrup (4.2 mg, 14%). LCMS (ES) [M+1]+ m/z 341.2

Example 13

Synthesis of N-ethyl-2-methyl-3-[3-(pyrrolidin-1-yl)propoxy]acridin-9-amine formate

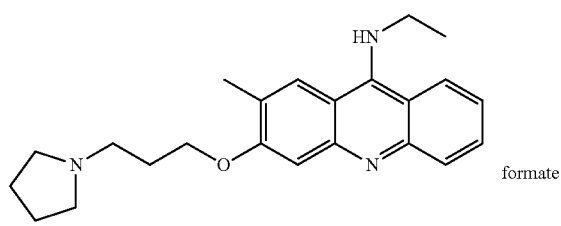 [SMILES: CCNc1c2ccccc2nc2cc(OCCCN3CCCC3)c(C)cc12]

formate

Into a 10-mL round-bottom flask purged and maintained with an inert atmosphere of nitrogen, was placed a mixture of 9-chloro-2-methyl-3-[3-(pyrrolidin-1-yl)propoxy]acridine (Intermediate I-5) (200 mg, 0.56 mmol, 1.00 equiv), DMSO (5 mL), ethanamine hydrochloride (46 mg, 0.56 mmol, 1.00 equiv) and t-BuOK (125 mg, 1.11 mmol, 2.00 equiv). The resulted solution was stirred for 16 h at 100° C. After the reaction was completed, the solids were filtered out. The filtrate was subjected to reverse preparative HPLC (Prep-C18, 5 μM XBridge column, 19×150 mm, Waters; gradient elution of 26% MeCN in water to 31% MeCN in water over a 7 min period, where both solvents contain 0.1% formic acid) to provide the title compound as an orange solid (44.9 mg, 22%). LCMS (ES) [M+1]m/z 364.3.

Example 14

Synthesis of 7-methoxy-N-methyl-6-[3-(pyrrolidin-1-yl)propoxy]-1,2,3,4-tetrahydroacridin-9-amine trifluoroacetate

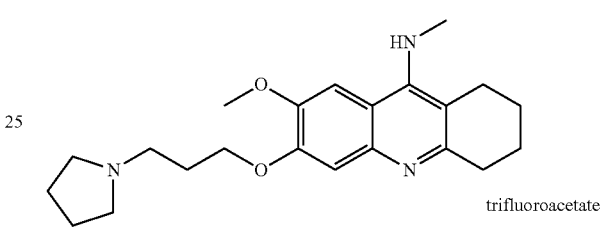

trifluoroacetate

Into a 20-mL sealed tube, was placed a mixture of 9-chloro-7-methoxy-6-(3-(pyrrolidin-1-yl)propoxy)-1,2,3,4-tetrahydroacridine (Intermediate III) (500 mg, 1.33 mmol, 1.00 equiv), n-pentanol (5 mL), methanamine hydrochloride (453 mg, 6.65 mmol, 5.00 equiv) and DIEA (860 mg, 6.65 mmol, 5.00 equiv). The mixture was heated with a microwave reactor for 30 min at 180° C. After the reaction was complete, the crude reaction mixture was filtered and subjected to reverse preparative HPLC (Prep-C18, 5 μM SunFire column, 19×150 mm, Waters; gradient elution of 11-23% MeCN in water over a 7 min period, where both solvents contain 0.1% TFA) to provide the title compound as a dark gray solid (54.0 mg, 7%). LCMS (ES) [M+1]+ m/z 370.4.

Example 15

Synthesis of N-{7-methoxy-6-[3-(pyrrolidin-1-yl)propoxy]-1H,2H,3H-cyclopenta[b]quinolin-9-yl}methanesulfonamide formate

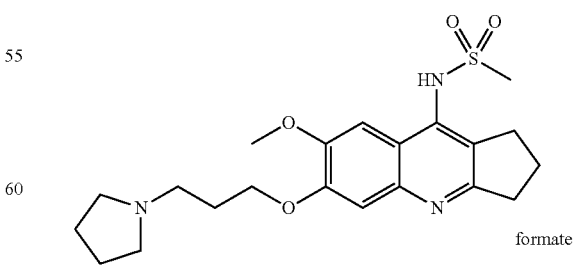

formate

To a rt mixture of 7-methoxy-6-[3-(pyrrolidin-1-yl)propoxy]-1H,2H,3H-cyclopenta[b]quinolin-9-amine formate (Example 11) (25.40 mg; 0.07 mmol; 1.00 eq.) in DCM (1.5 mL) was added Et₃N (0.3 mL) followed by methanesulfonyl chloride (17.04 mg; 0.15 mmol; 2.00 eq.). The mixture was allowed to stir at rt for 5 days. Two drops of water were added. After removal of the organic solvents under reduced pressure, the residue was dissolved in DMSO (0.5 mL), filtered and subjected for purification on reverse preparative HPLC (Prep-C18, 5 µM XBridge column, 19×150 mm, Waters; gradient elution of 35-65% MeCN in water over a 7 min period, where both solvents contain 0.1% formic acid) to provide the title compound as a white solid (1.9 mg, 6%). LCMS (ES) [M+1]⁺ m/z 420.2.

Example 16

Synthesis of 2-({7-methoxy-6-[3-(pyrrolidin-1-yl)propoxy]-1,2,3,4-tetrahydroacridin-9-yl}amino)ethan-1-ol formate

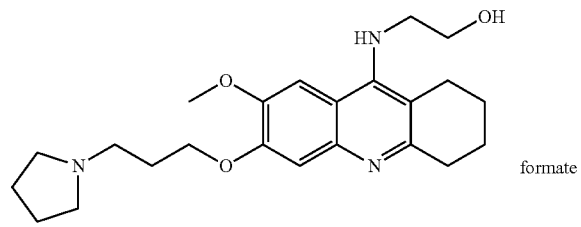 [SMILES: COc1cc2c(NCCO)c3c(nc2cc1OCCCN1CCCC1)CCCC3]

Into a 40-mL seal tube was placed a mixture of 9-chloro-7-methoxy-6-(3-(pyrrolidin-1-yl)propoxy)-1,2,3,4-tetrahydroacridine (Intermediate III) (250 mg, 0.67 mmol, 1.00 equiv), 1,4-dioxane (5 mL), 2-aminoethan-1-ol (204.4 mg, 3.35 mmol, 5.00 equiv), Cs₂CO₃ (436.8 mg, 1.34 mmol, 2.00 equiv), BINAP (52 mg, 0.067 mmol, 0.10 equiv) and Pd₂(dba)₃ (69.3 mg, 0.067 mmol, 0.10 equiv). The resulting mixture was purged with N₂ for 5 min, sealed and allowed to stir at 90° C. overnight. The crude reaction mixture was filtered through a small pad of celite. After removal of the organic solvents under reduced pressure, the residue was re-dissolved in DMSO. The solution was filtered and subjected to reverse phase preparative HPLC (Prep-C18, 5 µM XBridge column, 19×150 mm, Waters; gradient elution of 8-23% MeCN in water over a 7 min period, where both solvents contain 0.1% FA) to provide the title compound as a yellow solid (112.1 mg, 38%). LCMS (ES) [M+1]⁺ m/z 400.2.

Example 17

Synthesis of 2-({2-methoxy-3-[3-(pyrrolidin-1-yl)propoxy]acridin-9-yl}amino)acetic acid formate

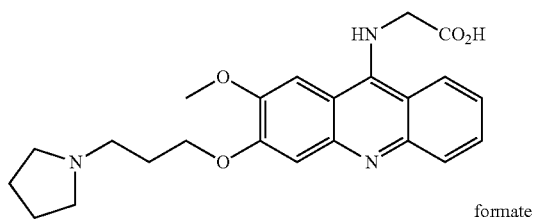 [SMILES: COc1cc2c(NCC(=O)O)c3ccccc3nc2cc1OCCCN1CCCC1]

A rt mixture of 9-chloro-2-methoxy-3-[3-(pyrrolidin-1-yl)propoxy]acridine (Intermediate I) (329.00 mg; 0.89 mmol; 1.00 eq.), ethyl 2-aminopropanoate hydrochloride (272.42 mg; 1.77 mmol; 2.00 eq.), sodium 2-methyl-2-propanolate (486.00 mg; 5.06 mmol; 5.70 eq.) in 1,4-dioxane (3.20 mL) was purged with N₂ for 5 min. To the resulting mixture was added Brettphos (49.58 mg; 0.06 mmol; 0.07 eq.), and the mixture was purged with N₂ for an additional 2 min. The vial was sealed and subjected to a microwave reactor (130° C., 2 h). The resulting reaction mixture was cooled to rt and treated with water (2 mL). After removal of the volatiles under reduced pressure, the residue was dissolved in DMSO (6 mL), filtered, and subjected for purification on reverse preparative HPLC (Prep-C18, 5 uM OBD column, 19×250 mm, waters; gradient elution of 0-25% MeCN in water over a 20 min period, where water contain 0.1% formic acid, flow rate: 20 mL/min, detector UV wavelength: 254 nm) to provide the title compound as a brown solid (90 mg, 25%). LCMS (ES) [M+1]⁺ m/z 410.2.

Example 18

Synthesis of methyl 2-({2-methoxy-3-[3-(pyrrolidin-1-yl)propoxy]acridin-9-yl}amino)acetate formate

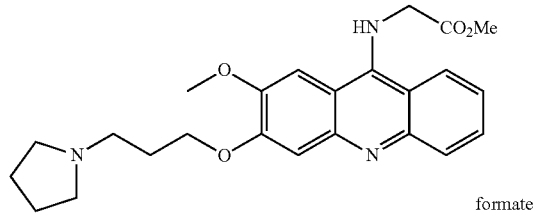 [SMILES: COC(=O)CNc1c2ccccc2nc2cc(OCCCN3CCCC3)c(OC)cc12]

To a mixture of 2-({2-methoxy-3-[3-(pyrrolidin-1-yl)propoxy]acridin-9-yl}amino)acetic acid formate (Example 17, 59.00 mg; 0.14 mmol; 1.00 eq.) in MeOH (3 mL) was added 37% aqueous HCl solution (0.4 mL). The resulting reaction mixture was allowed to stir at 70° C. overnight. The resulting mixture was cooled to rt. After removal of the volatiles under reduced pressure, the residue was dissolved in DMSO (0.5 mL), filtered, and subjected for purification on reverse preparative HPLC (Prep-C18, 5 uM OBD column, 19×250 mm, waters; gradient elution of 0-40% MeCN in water over a 20 min period, where water contain 0.1% formic acid, flow rate: 20 mL/min, detector UV wavelength: 254 nm) to provide the title compound as a brown solid (15.2 mg, 22%). LCMS (ES) [M+1]⁺ m/z 424.2.

Example 19

Synthesis of Further Exemplary Compounds of Formula (I)

3-[3-(pyrrolidin-1-yl)propoxy]acridin-9-ol trifluoroacetate was prepared from Intermediate I-4 following a procedure similar as described for the synthesis of Example 9.

2-chloro-N-methyl-3-[3-(pyrrolidin-1-yl)propoxy]acridin-9-amine formate; N-methyl-3-[3-(pyrrolidin-1-yl)propoxy]acridin-9-amine formate; and N,2-dimethyl-3-[3-(pyrrolidin-1-yl)propoxy]acridin-9-amine formate were prepared by reacting methylamine hydrochloride with the corresponding intermediates I-4, I-5 or I-6 respectively, following a procedure similar as described for the synthesis of Example 13.

7-methoxy-N-ethyl-6-[3-(pyrrolidin-1-yl)propoxy]-1,2,3,4-tetrahydroacridin-9-amine was prepared by reacting ethylamine hydrochloride with intermediate III following a procedure similar as described for the synthesis of Example 13.

2-methyl-N-(propan-2-yl)-3-[3-(pyrrolidin-1-yl)propoxy]acridin-9-amine formate; and 8-methoxy-N-(propan-2-yl)-7-[3-(pyrrolidin-1-yl)propoxy]benzo[b]1,5-naphthyridin-10-amine formate were prepared by reacting propan-2-amine with the corresponding intermediates I-5 or I-10 respectively, following a procedure similar as described for the synthesis of Example 2.

6-[3-(3-fluoropyrrolidin-1-yl)propoxy]-7-methoxy-N-methyl-1H,2H,3H-cyclopenta[b]quinolin-9-amine; 2-methoxy-3-[3-(morpholin-4-yl)propoxy]-N-(propan-2-yl)acridin-9-amine trifluoroacetate; 2-({2-methoxy-3-[3-(pyrrolidin-1-yl)propoxy]acridin-9-yl}amino)ethan-1-ol trifluoroacetate; 3-({2-methoxy-3-[3-(pyrrolidin-1-yl)propoxy]acridin-9-yl}amino)propan-1-ol trifluoroacetate; and 2-chloro-N-(propan-2-yl)-3-[3-(pyrrolidin-1-yl)propoxy]acridin-9-amine trifluoroacetate were prepared by reacting the corresponding intermediates I, I-1, I-6 or I-15 respectively, with the appropriate amines, following a procedure similar as described for the synthesis of Example 14.

3-[3-(diethylamino)propoxy]-2-methoxy-N-methylacridin-9-amine trifluoroacetate; 2-methoxy-N-methyl-3-[3-(piperidin-1-yl)propoxy]acridin-9-amine formate; 3-[3-(3-fluoropyrrolidin-1-yl)propoxy]-2-methoxy-N-methylacridin-9-amine formate; and 3-[3-(dimethylamino)propoxy]-2-methoxy-N-methylacridin-9-amine trifluoroacetate were prepared by reacting the corresponding intermediates I-1, I-2, I-3 or I-7 respectively, with methylamine, following a procedure similar as described for the synthesis of Example 1.

2-methoxy-N-(propan-2-yl)-3-[3-(pyrrolidin-1-yl)propoxy]-acridin-9-amine; 2-methoxy-N-(oxan-4-yl)-3-[3-(pyrrolidin-1-yl)propoxy]-acridin-9-amine trifluoroacetate; 7-methoxy-N-[1-(propan-2-yl)piperidin-4-yl]-6-[3-(pyrrolidin-1-yl)propoxy]-1,2,3,4-tetrahydroacridin-9-amine trifluoroacetate; 7-methoxy-N-(1-methylpiperidin-4-yl)-6-[3-(pyrrolidin-1-yl)propoxy]-1,2,3,4-tetrahydroacridin-9-amine trifluoroacetate; 7-methoxy-N-(oxan-4-yl)-6-[3-(pyrrolidin-1-yl)propoxy]-1H,2H,3H-cyclopenta[b]quinolin-9-amine; N-{7-methoxy-6-[3-(pyrrolidin-1-yl)propoxy]-1H,2H,3H-cyclopenta[b]quinolin-9-yl}-1-methylpiperidin-4-amine trifluoroacetate; 7-methoxy-N-(propan-2-yl)-6-[3-(pyrrolidin-1-yl)propoxy]-1,2,3,4-tetrahydroacridin-9-amine trifluoroacetate; 7-methoxy-N-(oxan-4-yl)-6-[3-(pyrrolidin-1-yl)propoxy]-1,2,3,4-tetrahydroacridin-9-amine trifluoroacetate; N-{7-methoxy-6-[3-(pyrrolidin-1-yl)propoxy]-1H,2H,3H-cyclopenta[b]quinolin-9-yl}-1-(propan-2-yl)piperidin-4-amine trifluoroacetate; 7-methoxy-N-methyl-6-[3-(pyrrolidin-1-yl)propoxy]-1H,2H,3H-cyclopenta[b]quinolin-9-amine formate; 7-methoxy-N-ethyl-6-[3-(pyrrolidin-1-yl)propoxy]-1H,2H,3H-cyclopenta[b]quinolin-9-amine formate; N-cyclopropyl-7-methoxy-6-[3-(pyrrolidin-1-yl)propoxy]-1H,2H,3H-cyclopenta[b]quinolin-9-amine trifluoroacetate; N-(cyclopropylmethyl)-7-methoxy-6-[3-(pyrrolidin-1-yl)propoxy]-1H,2H,3H-cyclopenta[b]quinolin-9-amine formate; 2-({7-methoxy-6-[3-(pyrrolidin-1-yl)propoxy]-1H,2H,3H-cyclopenta[b]quinolin-9-yl}amino)ethan-1-ol formate; N-cyclobutyl-7-methoxy-6-[3-(pyrrolidin-1-yl)propoxy]-1H,2H,3H-cyclopenta[b]quinolin-9-amine formate; N-cyclopentyl-7-methoxy-6-[3-(pyrrolidin-1-yl)propoxy]-1H,2H,3H-cyclopenta[b]quinolin-9-amine formate; 7-methoxy-N-propyl-6-[3-(pyrrolidin-1-yl)propoxy]-1H,2H,3H-cyclopenta[b]quinolin-9-amine formate; 7-methoxy-N-(2-methoxyethyl)-6-[3-(pyrrolidin-1-yl)propoxy]-1H,2H,3H-cyclopenta[b]quinolin-9-amine formate; 7-methoxy-N-[(oxetan-3-yl)methyl]-6-[3-(pyrrolidin-1-yl)propoxy]-1H,2H,3H-cyclopenta[b]quinolin-9-amine formate; N-{7-methoxy-6-[3-(pyrrolidin-1-yl)propoxy]-1H,2H,3H-cyclopenta[b]quinolin-9-yl}pyridin-2-amine formate; N-(cyclobutylmethyl)-7-methoxy-6-[3-(pyrrolidin-1-yl)propoxy]-1H,2H,3H-cyclopenta[b]quinolin-9-amine formate; 7-methoxy-N-(2-methylpropyl)-6-[3-(pyrrolidin-1-yl)propoxy]-1H,2H,3H-cyclopenta[b]quinolin-9-amine formate; N-(2,2-dimethylpropyl)-7-methoxy-6-[3-(pyrrolidin-1-yl)propoxy]-1H,2H,3H-cyclopenta[b]quinolin-9-amine formate; 7-methoxy-N-[(1-methylcyclopropyl)methyl]-6-[3-(pyrrolidin-1-yl)propoxy]-1H,2H,3H-cyclopenta[b]quinolin-9-amine formate; N-tert-butyl-7-methoxy-6-[3-(pyrrolidin-1-yl)propoxy]-1H,2H,3H-cyclopenta[b]quinolin-9-amine formate; N-benzyl-7-methoxy-6-[3-(pyrrolidin-1-yl)propoxy]-1H,2H,3H-cyclopenta[b]quinolin-9-amine formate; N-[(3,3-difluorocyclobutyl)methyl]-7-methoxy-6-[3-(pyrrolidin-1-yl)propoxy]-1H,2H,3H-cyclopenta[b]quinolin-9-amine; N-(3,3-difluorocyclobutyl)-7-methoxy-6-[3-(pyrrolidin-1-yl)propoxy]-1H,2H,3H-cyclopenta[b]quinolin-9-amine formate; 7-methoxy-6-[3-(pyrrolidin-1-yl)propoxy]-N-(2,2,2-trifluoroethyl)-1H,2H,3H-cyclopenta[b]quinolin-9-amine trifluoroacetate; 7-methoxy-6-[3-(pyrrolidin-1-yl)propoxy]-N-(3,3,3-trifluoropropyl)-1H,2H,3H-cyclopenta[b]quinolin-9-amine trifluoroacetate; N-(cyclopropylmethyl)-7-methoxy-6-[(1-methylpyrrolidin-3-yl)methoxy]-1H,2H,3H-cyclopenta[b]quinolin-9-amine formate; N-(2,6-dimethyloxan-4-yl)-7-methoxy-6-[3-(pyrrolidin-1-yl)propoxy]-1H,2H,3H-cyclopenta[b]quinolin-9-amine formate; 7-methoxy-N-[(pyridin-2-yl)methyl]-6-[3-(pyrrolidin-1-yl)propoxy]-1H,2H,3H-cyclopenta[b]quinolin-9-amine formate; 7-methoxy-N-[(pyridin-3-yl)methyl]-6-[3-(pyrrolidin-1-yl)propoxy]-1H,2H,3H-cyclopenta[b]quinolin-9-amine formate; 7-methoxy-N-(3-methoxycyclobutyl)-6-[3-(pyrrolidin-1-yl)propoxy]-1H,2H,3H-cyclopenta[b]quinolin-9-amine formate; (1s,3s)-3-({7-methoxy-6-[3-(pyrrolidin-1-yl)propoxy]-1H,2H,3H-cyclopenta[b]quinolin-9-yl}amino)cyclobutan-1-ol formate; 5-({7-methoxy-6-[3-(pyrrolidin-1-yl)propoxy]-1H,2H,3H-cyclopenta[b]quinolin-9-yl}amino)-1-methylpiperidin-2-one trifluoroacetate; 2-({7-methoxy-6-[3-(pyrrolidin-1-yl)propoxy]-1H,2H,3H-cyclopenta[b]quinolin-9-yl}amino)propane-1,3-diol formate; 4-({7-methoxy-6-[3-(pyrrolidin-1-yl)propoxy]-1H,2H,3H-cyclopenta[b]quinolin-9-yl}amino)pyrrolidin-2-one trifluoroacetate; 4-({7-methoxy-6-[3-(pyrrolidin-1-yl)propoxy]-1H,2H,3H-cyclopenta[b]quinolin-9-yl}amino)-1-methylpyrrolidin-2-one trifluoroacetate; 5-({7-methoxy-6-[3-(pyrrolidin-1-yl)propoxy]-1H,2H,3H-cyclopenta[b]quinolin-9-yl}amino)piperidin-2-one trifluoroacetate; 4-({7-methoxy-6-[3-(pyrrolidin-1-yl)propoxy]-1H,2H,3H-cyclopenta[b]quinolin-9-yl}amino)-1-methylpiperidin-2-one formate; 4-({7-methoxy-6-[3-(pyrrolidin-1-yl)propoxy]-1H,2H,3H-cyclopenta[b]quinolin-9-yl}amino)piperidin-2-one formate; N-(dicyclopropylmethyl)-7-methoxy-6-[3-(pyrrolidin-1-yl)propoxy]-1H,2H,3H-cyclopenta[b]quinolin-9-amine formate; N1-{7-methoxy-6-[3-(pyrrolidin-1-yl)propoxy]-1H,2H,3H-cyclopenta[b]quinolin-9-yl}hexane-1,6-diamine formate; 7-methoxy-N-[2-(morpholin-4-yl)ethyl]-6-[3-(pyrrolidin-1-yl)propoxy]-1H,2H,3H-cyclopenta[b]quinolin-9-amine formate; 7-methoxy-N-(oxetan-3-yl)-6-[3-(pyrrolidin-1-yl)propoxy]-1H,2H,3H-cyclopenta[b]quinolin-9-amine formate; 1-({7-methoxy-6-[3-(pyrrolidin-1-yl)

propoxy]-1H,2H,3H-cyclopenta[b]quinolin-9-yl}amino)-2-methylpropan-2-ol formate; N-{7-methoxy-6-[3-(pyrrolidin-1-yl)propoxy]-1H,2H,3H-cyclopenta[b]quinolin-9-yl}-1-methyl-1H-pyrazol-3-amine formate; methyl 3-[({7-methoxy-6-[3-(pyrrolidin-1-yl)propoxy]-1H,2H,3H-cyclopenta[b]quinolin-9-yl}amino)methyl]azetidine-1-carboxylate formate; 1-({7-methoxy-6-[3-(pyrrolidin-1-yl)propoxy]-1H,2H,3H-cyclopenta[b]quinolin-9-yl}amino)propan-2-ol formate; 7-methoxy-N-(3-methoxypropyl)-6-[3-(pyrrolidin-1-yl)propoxy]-1H,2H,3H-cyclopenta[b]quinolin-9-amine formate; 3-({7-methoxy-6-[3-(pyrrolidin-1-yl)propoxy]-1H,2H,3H-cyclopenta[b]quinolin-9-yl}amino)propan-1-ol formate; 3-({7-methoxy-6-[3-(pyrrolidin-1-yl)propoxy]-1H,2H,3H-cyclopenta[b]quinolin-9-yl}amino)-1-methylpyrrolidin-2-one; N-cyclopropyl-2-methoxy-3-[3-(pyrrolidin-1-yl)propoxy]acridin-9-amine formate; 2-methoxy-N-[(3S)-oxolan-3-yl]-3-[3-(pyrrolidin-1-yl)propoxy]acridin-9-amine formate; 2-methoxy-N-[(3R)-oxolan-3-yl]-3-[3-(pyrrolidin-1-yl)propoxy]acridin-9-amine formate; 2-methoxy-N-(oxetan-3-yl)-3-[3-(pyrrolidin-1-yl)propoxy]acridin-9-amine formate; 2-methoxy-N-{8-oxabicyclo[3.2.1]octan-3-yl}-3-[3-(pyrrolidin-1-yl)propoxy]acridin-9-amine formate; 5-({2-methoxy-3-[3-(pyrrolidin-1-yl)propoxy]acridin-9-yl}amino)-1-methylpiperidin-2-one trifluoroacetate; (1S,3R)-3-({2-methoxy-3-[3-(pyrrolidin-1-yl)propoxy]acridin-9-yl}amino)cyclopentan-1-ol formate; (1R,3R)-3-({2-methoxy-3-[3-(pyrrolidin-1-yl)propoxy]acridin-9-yl}amino)cyclopentan-1-ol formate; 4-({2-methoxy-3-[3-(pyrrolidin-1-yl)propoxy]acridin-9-yl}amino)piperidin-2-one trifluoroacetate; 1-ethyl-4-({2-methoxy-3-[3-(pyrrolidin-1-yl)propoxy]acridin-9-yl}amino)pyrrolidin-2-one trifluoroacetate; 3-({2-methoxy-3-[3-(pyrrolidin-1-yl)propoxy]acridin-9-yl}amino)-1-(propan-2-yl)pyrrolidin-2-one trifluoroacetate; 1-cyclobutyl-4-({2-methoxy-3-[3-(pyrrolidin-1-yl)propoxy]acridin-9-yl}amino)pyrrolidin-2-one trifluoroacetate; 1-ethyl-4-({2-methoxy-3-[3-(pyrrolidin-1-yl)propoxy]acridin-9-yl}amino)piperidin-2-one trifluoroacetate; 4-({2-methoxy-3-[3-(pyrrolidin-1-yl)propoxy]acridin-9-yl}amino)-1-(propan-2-yl)piperidin-2-one formate; 5-({2-methoxy-3-[3-(pyrrolidin-1-yl)propoxy]acridin-9-yl}amino)piperidin-2-one trifluoroacetate; N-[(2S)-butan-2-yl]-2-methoxy-3-[3-(pyrrolidin-1-yl)propoxy]acridin-9-amine trifluoroacetate; N-[(2R)-butan-2-yl]-2-methoxy-3-[3-(pyrrolidin-1-yl)propoxy]acridin-9-amine trifluoroacetate; 2-methoxy-N-(2-methoxypropyl)-3-[3-(pyrrolidin-1-yl)propoxy]acridin-9-amine trifluoroacetate; 2-methoxy-N-[(oxolan-3-yl)methyl]-3-[3-(pyrrolidin-1-yl)propoxy]acridin-9-amine trifluoroacetate; 2-methoxy-N-[(oxan-2-yl)methyl]-3-[3-(pyrrolidin-1-yl)propoxy]acridin-9-amine trifluoroacetate; 3-({2-methoxy-3-[3-(pyrrolidin-1-yl)propoxy]acridin-9-yl}amino)propanenitrile trifluoroacetate; (1R,4R)-4-({2-methoxy-3-[3-(pyrrolidin-1-yl)propoxy]acridin-9-yl}amino)-1-methylcyclohexan-1-ol trifluoroacetate; (1S,4S)-4-({2-methoxy-3-[3-(pyrrolidin-1-yl)propoxy]acridin-9-yl}amino)-1-methylcyclohexan-1-ol trifluoroacetate; N-(cyclopropylmethyl)-2-methoxy-3-[3-(pyrrolidin-1-yl)propoxy]acridin-9-amine formate; 4-({2-methoxy-3-[3-(pyrrolidin-1-yl)propoxy]acridin-9-yl}amino)-2-methylbutan-2-ol formate; 1-({2-methoxy-3-[3-(pyrrolidin-1-yl)propoxy]acridin-9-yl}amino)-2-methylpropan-2-ol formate; 4-({2-methoxy-3-[3-(pyrrolidin-1-yl)propoxy]acridin-9-yl}amino)butanenitrile formate; N-(2,6-dimethyloxan-4-yl)-2-methoxy-3-[3-(pyrrolidin-1-yl)propoxy]acridin-9-amine formate; 3-({2-methoxy-3-[3-(pyrrolidin-1-yl)propoxy]acridin-9-yl}amino)-1-methylpyrrolidin-2-one formate; 1-fluoro-7-methoxy-N-(2-methoxyethyl)-6-[3-(pyrrolidin-1-yl)propoxy]acridin-9-amine formate; (1S,3R)-3-({2-methyl-3-[3-(pyrrolidin-1-yl)propoxy]acridin-9-yl}amino)cyclopentan-1-ol trifluoroacetate; 2-methoxy-7-methyl-N-(oxan-4-yl)-3-[3-(pyrrolidin-1-yl)propoxy]acridin-9-amine formate; 2,7-dimethoxy-N-(oxan-4-yl)-3-[3-(pyrrolidin-1-yl)propoxy]acridin-9-amine trifluoroacetate; 5-fluoro-2-methoxy-N-(propan-2-yl)-3-[3-(pyrrolidin-1-yl)propoxy]acridin-9-amine formate; 8-methoxy-N-(propan-2-yl)-7-[3-(pyrrolidin-1-yl)propoxy]benzo[b]1,6-naphthyridin-10-amine formate; 1-({7-methoxy-8-[3-(pyrrolidin-1-yl)propoxy]benzo[b]1,8-naphthyridin-5-yl}amino)-2-methylpropan-2-ol formate; 7-methoxy-N-(oxan-4-yl)-6-[3-(pyrrolidin-1-yl)propoxy]-1,2,3,4-tetrahydroacridin-9-amine trifluoroacetate; N-cyclopropyl-7-methoxy-6-[3-(pyrrolidin-1-yl)propoxy]-1,2,3,4-tetrahydroacridin-9-amine trifluoroacetate; and 3-({7-methoxy-6-[3-(pyrrolidin-1-yl)propoxy]-1,2,3,4-tetrahydroacridin-9-yl}amino)cyclobutan-1-ol formate were prepared by reacting the corresponding intermediates I, I-1 to I-14, II or III respectively, and the appropriate amines or appropriate amine hydrochloride salts, following a procedure similar as described in either Example 4 or Example 15.

BIOLOGICAL EXAMPLES

Example 1

Determination of G9a Enzymatic Activity Assay

The G9a AlphaLISA assay was used to detect the methyl modifications of a biotinylated histone H3 peptide by the compounds. These modifications are done by the histone methyl transferase activity of the G9a enzyme. The assay consists of reading a chemiluminescent signal at 615 nm; this signal is generated by a laser excitation at 680 nm that transfers a reactive singlet oxygen between the donor beads and acceptor beads. Donor beads are streptavidin conjugated and bind to the biotin on the peptide. Acceptor beads are conjugated with an antibody that recognizes the specific G9a methyl mark on the peptide. If there is a methyl mark on the peptide, the acceptor beads will bind to the peptide. Upon binding, the acceptor beads will be in close proximity (<200 nm) of the donor beads and when the donor beads are excited, the transfer of the oxygen can occur and a strong signal will be generated. If there is no methyl mark, the interaction between beads will not occur and signal will be at background levels.

For the assay, the following buffer was used to set up reactions: 50 mM Tris-HCl pH9, 50 mM NaCl, 0.01% Tween-20 and 1 mM DTT (added fresh prior to starting the reactions). The assay is set up by adding a final concentration of 0.15 nM G9a, 15 uM S-adenosyl-methionine and, 100 nM biotinylated histone 3 peptide (1-21). The reaction is incubated at room temperature for 1 hour, and subsequently quenched by the addition of the acceptor beads (anti-H3k9me2 AlphaLISA acceptor beads, PerkinElmer #AL117) at a final concentration of 20 ug/mL. The acceptor beads are incubated for 1 hour. After 1 hour, the donor beads are added at a final concentration of 20 ug/mL (Alpha Streptavidin donor beads, PerkinElmer #6760002). Donor beads are incubated for 0.5 hours. Both donor and acceptor beads are resuspended in AlphaLISA 5X Epigenetics Buffer 1 Kit (PerkinElmer #AL008) prior to addition to the reaction. All manipulations and incubations with the donor and acceptor beads are done in subdued light. Signal is detected in an EnVision plate reader in Alpha mode (see ACS Med Chem Lett. 2014 Jan. 2; 5(2):205-9. doi: 10.1021/m1400496h. eCollection 2014. Discovery and development of potent and selective inhibitors of histone methyltransferase g9a.)

Percent inhibition was calculated for each compound dilution and the concentration that produced 50% inhibition was calculated. This value is presented as the $IC_{50}$. The $IC_{50}$ values for a representative number of compounds of the disclosure are provided in Table 3 below.

TABLE 3

| Entry (see Table 1) | G9a $IC_{50}$ [nM] |
|---|---|
| 1 | 1.3 |
| 3 | 4.4 |
| 4 | 1.1 |
| 6 | 42 |
| 7 | 1400 |
| 9 | 26.1 |
| 10 | 56.7 |
| 11 | 1230 |
| 14 | 76 |
| 16 | 11 |
| 17 | 510 |
| 19 | 10 |
| 29 | 250 |
| 31 | 17.5 |
| 32 | 14 |
| 34 | 7.6 |
| 38 | 16 |
| 39 | 20 |
| 40 | 150 |
| 44 | 19 |
| 46 | 36 |
| 50 | 26 |
| 52 | 65 |
| 53 | 21.6 |
| 54 | 60.1 |
| 56 | 16 |
| 57 | 33.1 |
| 58 | 46.4 |
| 60 | 14.6 |
| 65 | 7.7 |
| 70 | 35.8 |
| 71 | 17 |
| 73 | 11.2 |
| 80 | 65.3 |
| 87 | 18.5 |
| 98 | 6.8 |
| 99 | 17 |
| 104 | 134 |
| 105 | 20.6 |
| 114 | 54.3 |
| 115 | 215 |
| 117 | 139 |
| 118 | 75.5 |
| 119 | 28.5 |
| 120 | 62 |
| 121 | 64.2 |
| 122 | 23.8 |
| 123 | 251 |

Example 2

Fetal Hemoglobin Induction Assay

Cryopreserved bone marrow CD34$^+$ hematopoietic cells obtained from healthy adult human donors were used for all studies. A 21 day ex vivo serum free culture system was utilized that consists of two phases. In culture phase I (culture days 1-7), CD34$^+$ cells were placed in media containing StemPro-34 complete media (1-glutamine, pen-strep and StemPro-34 nutrient supplement) (Invitrogen, Carlsbad, Calif.) supplemented with 50 ng/ml SCF (HumanZyme, Chicago, Ill.), 50 ng/ml FLT3-Ligand (HumanZyme) and 10 ng/ml IL-3 (HumanZyme). During the first phase of culture (days 0-7), the CD34$^+$ cells differentiate into progenitor cell populations that include erythroblasts. After 7 days, the cells were transferred to erythropoietin (EPO; Stemcell) supplemented medium (phase 2; culture days 7-21) which is comprised of the following: StemPro-34 complete medium, 4 U/ml EPO, 3 μM mifepristone (Sigma Aldrich, St. Louis, Mo.), 10 g/ml insulin (Sigma Aldrich), 3 U/ml heparin (Sigma Aldrich) and 0.8 mg/ml holo transferrin (Sigma Aldrich). The Compounds are added during phase 2; days 7-21 to test fetal hemoglobin production (see Blood. 2015 Jul. 30; 126(5):665-72. Inhibition of G9a methyltransferase stimulates fetal hemoglobin production by facilitating LCR/γ-globin looping).

Expression levels of α-, β- and γ-globin genes are assessed by quantitative PCR analyses. HbF protein levels are assessed by the human Hemoglobin F enzyme-linked immunosorbent assay (ELISA) Quantitation Kit (Bethyl Laboratory, Montgomery, Tex., USA). Percentages of cells expressing HbF are assessed by flow cytometry analysis.

FORMULATION EXAMPLES

The following are representative pharmaceutical formulations containing a compound of the present disclosure.

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 μL of spray for each application.

What is claimed:
1. A compound of Formula (I):

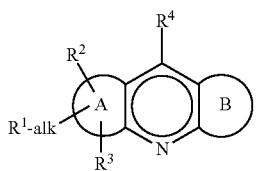

(I)

where:

is

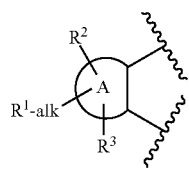

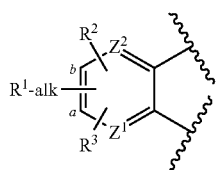

wherein:
$Z^1$ and $Z^2$ are independently:
C, when $R^2$ or $R^3$ is attached thereto;
CH;
or N;
alk is *—O—(CH$_2$)—, *—O—(CH$_2$)$_2$—, or *—O—(CH$_2$)$_3$—,
wherein -alk-$R^1$ is attached to carbon (a) or (b), and * denotes the point of attachment to ring A;
$R^1$ is:
—NR$^6$R$^7$, where R$^6$ and R$^7$ are independently hydrogen, alkyl, hydroxyalkyl, alkoxyalkyl, or haloalkoxyalkyl;
heterocyclyl, optionally substituted with R$^a$, R$^b$, or R$^c$ independently selected from alkyl, hydroxyl, alkoxy, halo, haloalkyl, alkylcarbonyl, and haloalkylcarbonyl;
or,
spiroheterocycloamino, wherein a nitrogen atom of the spiroheterocycloamino is attached to alk;
$R^2$ is alkyl, cycloalkyl, halo, hydroxyl, alkoxy, haloalkoxy, or cyano;
$R^3$ is hydrogen;
$R^4$ is:
NR$^e$R$^f$, where R$^e$ is hydrogen or alkyl and R$^f$ is hydrogen, alkyl, aminoalkyl, cyanoalkyl, carboxyalkyl, alkoxycarbonylalkyl, haloalkyl, hydroxyalkyl, alkoxyalkyl, cycloalkyl, cycloalkylalkyl, dicycloalkylalkyl, aryl, aralkyl, heteroaryl, heteroaralkyl, heterocyclyl, bridged heterocyclyl, heterocyclylalkyl, alkylsulfonyl, cycloalkylsulfonyl, cycloalkylalkylsulfonyl, arylsulfonyl, aralkylsulfonyl, heteroarylsulfonyl, heteroaralkylsulfonyl, heterocyclylsulfonyl, or heterocyclylalkylsulfonyl;
wherein cycloalkyl, aryl, heteroaryl, and heterocyclyl either alone or in cycloalkylalkyl, aralkyl, heteroaralkyl, heterocyclylalkyl, cycloalkylsulfonyl, heteroaralkylsulfonyl, or heterocyclylalkylsulfonyl in R$^f$ are optionally substituted with R$^g$, R$^h$, or R$^i$ independently selected from alkyl, cycloalkyl, hydroxyl, alkoxy, alkoxycarbonyl, halo, haloalkyl, and haloalkoxy; and
further wherein alkylene in aralkyl, heteroaralkyl, heterocyclylalkyl, and cycloalkylalkyl is optionally substituted with one, two, or three deuterium;
ring B is:
phenyl;
6-membered heteroaryl containing one or two heteroatoms independently selected from nitrogen and sulfur;
or,
5- or 6- or 7-membered cycloalkyl;
each optionally substituted with R$^j$, R$^k$, or R$^l$ independently selected from alkyl, hydroxyl, alkoxy, halo, haloalkyl, and haloalkoxy;
or,
a pharmaceutically acceptable salt thereof.
2. The compound of claim 1 or a pharmaceutically acceptable salt thereof wherein
$R^4$ is:
NR$^e$R$^f$,
where R$^e$ is hydrogen or alkyl and R$^f$ is hydrogen, alkyl, cycloalkyl, halocycloalkyl, cycloalkylalkyl, aryl, aralkyl, heteroaryl, heteroaralkyl, heterocyclyl, or heterocyclylalkyl,
wherein aryl, heteroaryl, and heterocyclyl either alone or in aralkyl, heteroaralkyl, or heterocyclylalkyl in R are optionally substituted with $R^g$, $R^h$, or $R^i$ independently selected from alkyl, hydroxyl, alkoxy, halo, haloalkyl, and haloalkoxy.

3. The compound of claim 1 or a pharmaceutically acceptable salt thereof wherein ring B is phenyl optionally substituted with $R^j$, $R^k$, or $R^l$ independently selected from alkyl, hydroxyl, alkoxy, halo, haloalkyl, and haloalkoxy.

4. The compound of claim 1 or a pharmaceutically acceptable salt thereof wherein ring B is 5- or 6-membered cycloalkyl optionally substituted with $R^j$, $R^k$, or $R^l$ independently selected from alkyl, hydroxyl, alkoxy, halo, haloalkyl, and haloalkoxy.

5. The compound of claim 1 or a pharmaceutically acceptable salt thereof wherein $Z^1$ and $Z^2$ are C or CH.

6. The compound of claim 5 or a pharmaceutically acceptable salt thereof wherein -alk-$R^1$ is attached to carbon (a) and $R^2$ is attached to carbon (b).

7. The compound of claim 6 or a pharmaceutically acceptable salt thereof wherein $R^1$ is —$NR^6R^7$ where —$NR^6R^7$ is amino, methylamino, ethylamino, dimethylamino, or diethylamino.

8. The compound of claim 6 or a pharmaceutically acceptable salt thereof wherein $R^1$ is heterocyclyl optionally substituted with $R^a$, $R^b$, or $R^c$ independently selected from alkyl, hydroxyl, alkoxy, and halo.

9. The compound of claim 6 or a pharmaceutically acceptable salt thereof, wherein -alk-$R^1$ is *—O—$(CH_2)_3$-pyrrolidin-1-yl, *—O—$(CH_2)_3$-piperidin-1-yl, or *—O—$(CH_2)_3$-morpholin-4-yl, each optionally substituted with $R^a$ or $R^b$ independently selected from methyl, hydroxyl, methoxy, and fluoro.

10. The compound of claim 6 or a pharmaceutically acceptable salt thereof wherein $R^2$ is alkyl, halo, or alkoxy.

11. The compound of claim 6 or a pharmaceutically acceptable salt thereof wherein
$R^4$ is $NR^eR^f$,
where $R^e$ is hydrogen or alkyl and $R^f$ is hydrogen, alkyl, haloalkyl, hydroxyalkyl, alkoxyalkyl, cycloalkyl, cycloalkylalkyl, aryl, aralkyl, heteroaryl, heteroaralkyl, heterocyclyl, heterocyclylalkyl, or alkylsulfonyl,
wherein cycloalkyl, aryl, heteroaryl, and heterocyclyl either alone or in cycloalkylalkyl, aralkyl, heteroaralkyl, or heterocyclylalkyl in $R^f$ is optionally substituted with $R^g$, $R^h$, or $R^i$ independently selected from alkyl, hydroxyl, alkoxy, halo, haloalkyl, and haloalkoxy.

12. The compound of claim 11 or a pharmaceutically acceptable salt thereof, wherein $R^4$ is —NH-alkyl.

13. The compound of claim 11 or a pharmaceutically acceptable salt thereof, wherein $R^4$ is —NH-cycloalkyl, optionally substituted with $R^g$ or $R^h$ independently selected from alkyl, hydroxyl, alkoxy, halo, haloalkyl, and haloalkoxy.

14. The compound of claim 11 or a pharmaceutically acceptable salt thereof, wherein $R^4$ is —NH-heterocyclyl optionally substituted with $R^g$, $R^h$, or $R^i$ independently selected from alkyl, hydroxyl, alkoxy, halo, haloalkyl, and haloalkoxy.

15. The compound of claim 5 or a pharmaceutically acceptable salt thereof, wherein $R^4$ is —NH-cycloalkylalkyl optionally substituted with $R^g$ or $R^h$ independently selected from alkyl, hydroxyl, alkoxy, halo, haloalkyl, and haloalkoxy.

16. The compound of claim 11 or a pharmaceutically acceptable salt thereof, wherein $R^4$ is —NH-heterocyclylalkyl optionally substituted with $R^g$, $R^h$, or $R^i$ independently selected from alkyl, hydroxyl, alkoxy, halo, haloalkyl, and haloalkoxy.

17. A compound selected from:
2-methoxy-N-methyl-3-[3-(pyrrolidin-1-yl)propoxy]acridin-9-amine;
2-methoxy-N-(propan-2-yl)-3-[3-(pyrrolidin-1-yl)propoxy]-acridin-9-amine;
2-methoxy-N-(oxan-4-yl)-3-[3-(pyrrolidin-1-yl)propoxy]-acridin-9-amine;
2-methoxy-N-(1-methylpiperidin-4-yl)-3-[3-(pyrrolidin-1-yl)propoxy]acridin-9-amine;
2-methoxy-N-[1-(propan-2-yl)piperidin-4-yl]-3-[3-(pyrrolidin-1-yl)propoxy]acridin-9-amine;
2-methoxy-3-[3-(pyrrolidin-1-yl)propoxy]acridin-9-ol;
9-ethoxy-2-methoxy-3-[3-(pyrrolidin-1-yl)propoxy]acridine;
2-chloro-N-methyl-3-[3-(pyrrolidin-1-yl)propoxy]acridin-9-amine;
N,2-dimethyl-3-[3-(pyrrolidin-1-yl)propoxy]acridin-9-amine;
N-ethyl-2-methyl-3-[3-(pyrrolidin-1-yl)propoxy]acridin-9-amine;
2-methyl-N-(propan-2-yl)-3-[3-(pyrrolidin-1-yl)propoxy]acridin-9-amine;
3-[3-(diethylamino)propoxy]-2-methoxy-N-methylacridin-9-amine;
2-methoxy-N-methyl-3-[3-(piperidin-1-yl)propoxy]acridin-9-amine;
7-methoxy-N-[1-(propan-2-yl)piperidin-4-yl]-6-[3-(pyrrolidin-1-yl)propoxy]-1,2,3,4-tetrahydroacridin-9-amine;
7-methoxy-6-[3-(pyrrolidin-1-yl)propoxy]-1,2,3,4-tetrahydroacridine;
7-methoxy-N-(1-methylpiperidin-4-yl)-6-[3-(pyrrolidin-1-yl)propoxy]-1,2,3,4-tetrahydroacridin-9-amine;
7-methoxy-N-(propan-2-yl)-6-[3-(pyrrolidin-1-yl)propoxy]-1H,2H,3H-cyclopenta[b]quinolin-9-amine;
7-methoxy-N-(oxan-4-yl)-6-[3-(pyrrolidin-1-yl)propoxy]-1H,2H,3H-cyclopenta[b]quinolin-9-amine;
N-{7-methoxy-6-[3-(pyrrolidin-1-yl)propoxy]-1H,2H,3H-cyclopenta[b]quinolin-9-yl}-1-methylpiperidin-4-amine;
7-methoxy-N-(propan-2-yl)-6-[3-(pyrrolidin-1-yl)propoxy]-1,2,3,4-tetrahydroacridin-9-amine;
7-methoxy-N-(oxan-4-yl)-6-[3-(pyrrolidin-1-yl)propoxy]-1,2,3,4-tetrahydroacridin-9-amine;
N-{7-methoxy-6-[3-(pyrrolidin-1-yl)propoxy]-1H,2H,3H-cyclopenta[b]quinolin-9-yl}-1-(propan-2-yl)piperidin-4-amine;
7-methoxy-N-methyl-6-[3-(pyrrolidin-1-yl)propoxy]-1,2,3,4-tetrahydroacridin-9-amine;
7-methoxy-N-methyl-6-[3-(pyrrolidin-1-yl)propoxy]-1H,2H,3H-cyclopenta[b]quinolin-9-amine;
7-methoxy-N-ethyl-6-[3-(pyrrolidin-1-yl)propoxy]-1H,2H,3H-cyclopenta[b]quinolin-9-amine;
7-methoxy-N-ethyl-6-[3-(pyrrolidin-1-yl)propoxy]-1,2,3,4-tetrahydroacridin-9-amine;
6-[3-(3-fluoropyrrolidin-1-yl)propoxy]-7-methoxy-N-methyl-1H,2H,3H-cyclopenta[b]quinolin-9-amine;
2-methoxy-3-[3-(morpholin-4-yl)propoxy]-N-(propan-2-yl)acridin-9-amine;
N-cyclopropyl-7-methoxy-6-[3-(pyrrolidin-1-yl)propoxy]-1H,2H,3H-cyclopenta[b]quinolin-9-amine;
N-(cyclopropylmethyl)-7-methoxy-6-[3-(pyrrolidin-1-yl)propoxy]-1H,2H,3H-cyclopenta[b]quinolin-9-amine;

7-methoxy-6-[3-(pyrrolidin-1-yl)propoxy]-1H,2H,3H-cyclopenta[b]quinolin-9-amine;

2-({7-methoxy-6-[3-(pyrrolidin-1-yl)propoxy]-1H,2H,3H-cyclopenta[b]quinolin-9-yl}amino)ethan-1-ol;

N-cyclobutyl-7-methoxy-6-[3-(pyrrolidin-1-yl)propoxy]-1H,2H,3H-cyclopenta[b]quinolin-9-amine;

N-cyclopentyl-7-methoxy-6-[3-(pyrrolidin-1-yl)propoxy]-1H,2H,3H-cyclopenta[b]quinolin-9-amine;

7-methoxy-N-propyl-6-[3-(pyrrolidin-1-yl)propoxy]-1H,2H,3H-cyclopenta[b]quinolin-9-amine;

7-methoxy-N-(2-methoxyethyl)-6-[3-(pyrrolidin-1-yl)propoxy]-1H,2H,3H-cyclopenta[b]quinolin-9-amine;

7-methoxy-N-[(oxetan-3-yl)methyl]-6-[3-(pyrrolidin-1-yl)propoxy]-1H,2H,3H-cyclopenta[b]quinolin-9-amine;

N-{7-methoxy-6-[3-(pyrrolidin-1-yl)propoxy]-1H,2H,3H-cyclopenta[b]quinolin-9-yl}pyridin-2-amine;

N-(cyclobutylmethyl)-7-methoxy-6-[3-(pyrrolidin-1-yl)propoxy]-1H,2H,3H-cyclopenta[b]quinolin-9-amine;

7-methoxy-N-(2-methylpropyl)-6-[3-(pyrrolidin-1-yl)propoxy]-1H,2H,3H-cyclopenta[b]quinolin-9-amine;

N-(2,2-dimethylpropyl)-7-methoxy-6-[3-(pyrrolidin-1-yl)propoxy]-1H,2H,3H-cyclopenta[b]quinolin-9-amine;

7-methoxy-N-[(1-methylcyclopropyl)methyl]-6-[3-(pyrrolidin-1-yl)propoxy]-1H,2H,3H-cyclopenta[b]quinolin-9-amine;

N-tert-butyl-7-methoxy-6-[3-(pyrrolidin-1-yl)propoxy]-1H,2H,3H-cyclopenta[b]quinolin-9-amine;

N-benzyl-7-methoxy-6-[3-(pyrrolidin-1-yl)propoxy]-1H,2H,3H-cyclopenta[b]quinolin-9-amine;

N-{7-methoxy-6-[3-(pyrrolidin-1-yl)propoxy]-1H,2H,3H-cyclopenta[b]quinolin-9-yl}methanesulfonamide;

N-[(3,3-difluorocyclobutyl)methyl]-7-methoxy-6-[3-(pyrrolidin-1-yl)propoxy]-1H,2H,3H-cyclopenta[b]quinolin-9-amine;

N-(3,3-difluorocyclobutyl)-7-methoxy-6-[3-(pyrrolidin-1-yl)propoxy]-1H,2H,3H-cyclopenta[b]quinolin-9-amine;

7-methoxy-6-[3-(pyrrolidin-1-yl)propoxy]-N-(2,2,2-trifluoroethyl)-1H,2H,3H-cyclopenta[b]quinolin-9-amine;

7-methoxy-6-[3-(pyrrolidin-1-yl)propoxy]-N-(3,3,3-trifluoropropyl)-1H,2H,3H-cyclopenta[b]quinolin-9-amine;

N-(cyclopropylmethyl)-7-methoxy-6-[(1-methylpyrrolidin-3-yl)methoxy]-1H,2H,3H-cyclopenta[b]quinolin-9-amine;

N-(2,6-dimethyloxan-4-yl)-7-methoxy-6-[3-(pyrrolidin-1-yl)propoxy]-1H,2H,3H-cyclopenta[b]quinolin-9-amine;

7-methoxy-N-[(pyridin-2-yl)methyl]-6-[3-(pyrrolidin-1-yl)propoxy]-1H,2H,3H-cyclopenta[b]quinolin-9-amine;

7-methoxy-N-[(pyridin-3-yl)methyl]-6-[3-(pyrrolidin-1-yl)propoxy]-1H,2H,3H-cyclopenta[b]quinolin-9-amine;

7-methoxy-N-(3-methoxycyclobutyl)-6-[3-(pyrrolidin-1-yl)propoxy]-1H,2H,3H-cyclopenta[b]quinolin-9-amine;

(1s,3s)-3-({7-methoxy-6-[3-(pyrrolidin-1-yl)propoxy]-1H,2H,3H-cyclopenta[b]quinolin-9-yl}amino)cyclobutan-1-ol;

5-({7-methoxy-6-[3-(pyrrolidin-1-yl)propoxy]-1H,2H,3H-cyclopenta[b]quinolin-9-yl}amino)-1-methylpiperidin-2-one;

2-({7-methoxy-6-[3-(pyrrolidin-1-yl)propoxy]-1H,2H,3H-cyclopenta[b]quinolin-9-yl}amino)propane-1,3-diol;

4-({7-methoxy-6-[3-(pyrrolidin-1-yl)propoxy]-1H,2H,3H-cyclopenta[b]quinolin-9-yl}amino)pyrrolidin-2-one;

4-({7-methoxy-6-[3-(pyrrolidin-1-yl)propoxy]-1H,2H,3H-cyclopenta[b]quinolin-9-yl}amino)-1-methylpyrrolidin-2-one;

5-({7-methoxy-6-[3-(pyrrolidin-1-yl)propoxy]-1H,2H,3H-cyclopenta[b]quinolin-9-yl}amino)piperidin-2-one;

4-({7-methoxy-6-[3-(pyrrolidin-1-yl)propoxy]-1H,2H,3H-cyclopenta[b]quinolin-9-yl}amino)-1-methylpiperidin-2-one;

4-({7-methoxy-6-[3-(pyrrolidin-1-yl)propoxy]-1H,2H,3H-cyclopenta[b]quinolin-9-yl}amino)piperidin-2-one;

N-(dicyclopropylmethyl)-7-methoxy-6-[3-(pyrrolidin-1-yl)propoxy]-1H,2H,3H-cyclopenta[b]quinolin-9-amine;

N1-{7-methoxy-6-[3-(pyrrolidin-1-yl)propoxy]-1H,2H,3H-cyclopenta[b]quinolin-9-yl}hexane-1,6-diamine;

7-methoxy-N-[2-(morpholin-4-yl)ethyl]-6-[3-(pyrrolidin-1-yl)propoxy]-1H,2H,3H-cyclopenta[b]quinolin-9-amine;

7-methoxy-N-(oxetan-3-yl)-6-[3-(pyrrolidin-1-yl)propoxy]-1H,2H,3H-cyclopenta[b]quinolin-9-amine;

1-({7-methoxy-6-[3-(pyrrolidin-1-yl)propoxy]-1H,2H,3H-cyclopenta[b]quinolin-9-yl}amino)-2-methylpropan-2-ol;

N-{7-methoxy-6-[3-(pyrrolidin-1-yl)propoxy]-1H,2H,3H-cyclopenta[b]quinolin-9-yl}-1-methyl-1H-pyrazol-3-amine;

methyl 3-[({7-methoxy-6-[3-(pyrrolidin-1-yl)propoxy]-1H,2H,3H-cyclopenta[b]quinolin-9-yl}amino)methyl]azetidine-1-carboxylate;

1-({7-methoxy-6-[3-(pyrrolidin-1-yl)propoxy]-1H,2H,3H-cyclopenta[b]quinolin-9-yl}amino)propan-2-ol;

7-methoxy-N-(3-methoxypropyl)-6-[3-(pyrrolidin-1-yl)propoxy]-1H,2H,3H-cyclopenta[b]quinolin-9-amine;

3-({7-methoxy-6-[3-(pyrrolidin-1-yl)propoxy]-1H,2H,3H-cyclopenta[b]quinolin-9-yl}amino)propan-1-ol;

3-({7-methoxy-6-[3-(pyrrolidin-1-yl)propoxy]-1H,2H,3H-cyclopenta[b]quinolin-9-yl}amino)-1-methylpyrrolidin-2-one;

N-cyclopropyl-2-methoxy-3-[3-(pyrrolidin-1-yl)propoxy]acridin-9-amine;

2-methoxy-N-[(3S)-oxolan-3-yl]-3-[3-(pyrrolidin-1-yl)propoxy]acridin-9-amine;

2-methoxy-N-[(3R)-oxolan-3-yl]-3-[3-(pyrrolidin-1-yl)propoxy]acridin-9-amine;

2-methoxy-N-(oxetan-3-yl)-3-[3-(pyrrolidin-1-yl)propoxy]acridin-9-amine;

2-methoxy-N-{8-oxabicyclo[3.2.1]octan-3-yl}-3-[3-(pyrrolidin-1-yl)propoxy]acridin-9-amine;

5-({2-methoxy-3-[3-(pyrrolidin-1-yl)propoxy]acridin-9-yl}amino)-1-methylpiperidin-2-one;

(1S,3R)-3-({2-methoxy-3-[3-(pyrrolidin-1-yl)propoxy]acridin-9-yl}amino)cyclopentan-1-ol;

(1R,3R)-3-({2-methoxy-3-[3-(pyrrolidin-1-yl)propoxy]acridin-9-yl}amino)cyclopentan-1-ol;

4-({2-methoxy-3-[3-(pyrrolidin-1-yl)propoxy]acridin-9-yl}amino)piperidin-2-one;

1-ethyl-4-({2-methoxy-3-[3-(pyrrolidin-1-yl)propoxy]acridin-9-yl}amino)pyrrolidin-2-one;

3-({2-methoxy-3-[3-(pyrrolidin-1-yl)propoxy]acridin-9-yl}amino)-1-(propan-2-yl)pyrrolidin-2-one;
1-cyclobutyl-4-({2-methoxy-3-[3-(pyrrolidin-1-yl)propoxy]acridin-9-yl}amino)pyrrolidin-2-one;
1-ethyl-4-({2-methoxy-3-[3-(pyrrolidin-1-yl)propoxy]acridin-9-yl}amino)piperidin-2-one;
4-({2-methoxy-3-[3-(pyrrolidin-1-yl)propoxy]acridin-9-yl}amino)-1-(propan-2-yl)piperidin-2-one;
5-({2-methoxy-3-[3-(pyrrolidin-1-yl)propoxy]acridin-9-yl}amino)piperidin-2-one;
N-[(2S)-butan-2-yl]-2-methoxy-3-[3-(pyrrolidin-1-yl)propoxy]acridin-9-amine;
N-[(2R)-butan-2-yl]-2-methoxy-3-[3-(pyrrolidin-1-yl)propoxy]acridin-9-amine;
2-({2-methoxy-3-[3-(pyrrolidin-1-yl)propoxy]acridin-9-yl}amino)ethan-1-ol;
3-({2-methoxy-3-[3-(pyrrolidin-1-yl)propoxy]acridin-9-yl}amino)propan-1-ol;
2-methoxy-N-(2-methoxypropyl)-3-[3-(pyrrolidin-1-yl)propoxy]acridin-9-amine;
2-methoxy-N-[(oxolan-3-yl)methyl]-3-[3-(pyrrolidin-1-yl)propoxy]acridin-9-amine;
2-methoxy-N-[(oxan-2-yl)methyl]-3-[3-(pyrrolidin-1-yl)propoxy]acridin-9-amine;
3-({2-methoxy-3-[3-(pyrrolidin-1-yl)propoxy]acridin-9-yl}amino)propanenitrile;
(1R,4R)-4-({2-methoxy-3-[3-(pyrrolidin-1-yl)propoxy]acridin-9-yl}amino)-1-methylcyclohexan-1-ol;
(1S,4S)-4-({2-methoxy-3-[3-(pyrrolidin-1-yl)propoxy]acridin-9-yl}amino)-1-methylcyclohexan-1-ol;
N-(cyclopropylmethyl)-2-methoxy-3-[3-(pyrrolidin-1-yl)propoxy]acridin-9-amine;
4-({2-methoxy-3-[3-(pyrrolidin-1-yl)propoxy]acridin-9-yl}amino)-2-methylbutan-2-ol;
1-({2-methoxy-3-[3-(pyrrolidin-1-yl)propoxy]acridin-9-yl}amino)-2-methylpropan-2-ol;
2-({2-methoxy-3-[3-(pyrrolidin-1-yl)propoxy]acridin-9-yl}amino)acetic acid;
methyl 2-({2-methoxy-3-[3-(pyrrolidin-1-yl)propoxy]acridin-9-yl}amino)acetate;
4-({2-methoxy-3-[3-(pyrrolidin-1-yl)propoxy]acridin-9-yl}amino)butanenitrile;
N-(2,6-dimethyloxan-4-yl)-2-methoxy-3-[3-(pyrrolidin-1-yl)propoxy]acridin-9-amine;
3-({2-methoxy-3-[3-(pyrrolidin-1-yl)propoxy]acridin-9-yl}amino)-1-methylpyrrolidin-2-one;
2-methoxy-N-methyl-3-[(1-methylpyrrolidin-3-yl)methoxy]acridin-9-amine;
2-methoxy-N-methyl-3-[(1-methylpiperidin-3-yl)methoxy]acridin-9-amine;
1-fluoro-7-methoxy-N-(2-methoxyethyl)-6-[3-(pyrrolidin-1-yl)propoxy]acridin-9-amine;
(1S,3R)-3-({2-methyl-3-[3-(pyrrolidin-1-yl)propoxy]acridin-9-yl}amino)cyclopentan-1-ol;
2-chloro-N-(propan-2-yl)-3-[3-(pyrrolidin-1-yl)propoxy]acridin-9-amine;
2-methoxy-7-methyl-N-(oxan-4-yl)-3-[3-(pyrrolidin-1-yl)propoxy]acridin-9-amine;
2,7-dimethoxy-N-(oxan-4-yl)-3-[3-(pyrrolidin-1-yl)propoxy]acridin-9-amine;
2-methoxy-3-[(1-methylpyrrolidin-3-yl)methoxy]-N-(oxan-4-yl)acridin-9-amine;
3-[3-(3-fluoropyrrolidin-1-yl)propoxy]-2-methoxy-N-methylacridin-9-amine;
2-ethoxy-N-methyl-3-[3-(pyrrolidin-1-yl)propoxy]acridin-9-amine;
3-ethoxy-N-methyl-2-[3-(pyrrolidin-1-yl)propoxy]acridin-9-amine;
3-[3-(dimethylamino)propoxy]-2-methoxy-N-methylacridin-9-amine;
5-fluoro-2-methoxy-N-(propan-2-yl)-3-[3-(pyrrolidin-1-yl)propoxy]acridin-9-amine;
8-methoxy-N-(propan-2-yl)-7-[3-(pyrrolidin-1-yl)propoxy]benzo[b]1,6-naphthyridin-10-amine;
8-methoxy-N-(propan-2-yl)-7-[3-(pyrrolidin-1-yl)propoxy]benzo[b]1,5-naphthyridin-10-amine;
1-({7-methoxy-8-[3-(pyrrolidin-1-yl)propoxy]benzo[b]1,8-naphthyridin-5-yl}amino)-2-methylpropan-2-ol;
N-cyclopropyl-7-methoxy-6-[3-(pyrrolidin-1-yl)propoxy]-1,2,3,4-tetrahydroacridin-9-amine;
2-({7-methoxy-6-[3-(pyrrolidin-1-yl)propoxy]-1,2,3,4-tetrahydroacridin-9-yl}amino)ethan-1-ol; and
3-({7-methoxy-6-[3-(pyrrolidin-1-yl)propoxy]-1,2,3,4-tetrahydroacridin-9-yl}amino)cyclobutan-1-ol;
or a pharmaceutically acceptable salt thereof.

18. A pharmaceutical composition comprising a compound of claim 1 or a pharmaceutically acceptable salt thereof, and a pharmaceutically acceptable excipient.

19. A compound of Formula (II):

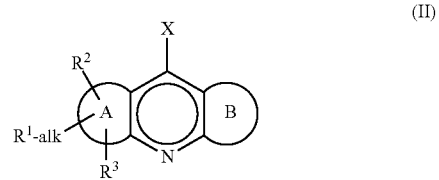

(II)

where:

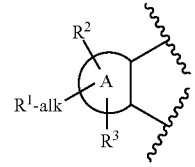

is

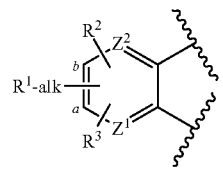

wherein:
$Z^1$ and $Z^2$ are independently:
C, when $R^2$ or $R^3$ is attached thereto;
CH;
or N;
alk is *—O—(CH$_2$)—, *—O—(CH$_2$)$_2$—, or *—O—(CH$_2$)$_3$—, wherein -alk-$R^1$ is attached to carbon (a) or (b), and * denotes the point of attachment to ring A;

R¹ is:
- —NR⁶R⁷,
    - where R⁶ and R⁷ are independently hydrogen, alkyl, hydroxyalkyl, alkoxyalkyl, haloalkyl, or haloalkoxyalkyl;
    - heterocyclyl, optionally substituted with Rᵃ, Rᵇ, or Rᶜ independently selected from alkyl, hydroxyl, alkoxy, halo, haloalkyl, alkylcarbonyl, and haloalkylcarbonyl;
- or,
- spiroheterocycloamino wherein a nitrogen atom of the spiroheterocycloamino is attached to alk;

R² is alkyl, cycloalkyl, halo, hydroxyl, alkoxy, haloalkoxy, or cyano;
R³ is hydrogen;
X is halo, tosylate, mesylate, or triflate; and
ring B is:
- phenyl;
- 6-membered heteroaryl containing one or two heteroatoms independently selected from nitrogen and sulfur;
- or,
- 5- or 6- or 7-membered cycloalkyl;
    - each optionally substituted with Rʲ, Rᵏ, or Rˡ independently selected from alkyl, hydroxyl, alkoxy, halo, haloalkyl, and haloalkoxy;

or a salt thereof.

20. A compound selected from:
3-[3-(pyrrolidin-1-yl)propoxy]acridin-9-ol and N-methyl-3-[3-(pyrrolidin-1-yl) propoxy]acridin-9-amine, or a pharmaceutically acceptable salt thereof.

* * * * *

UNITED STATES PATENT AND TRADEMARK OFFICE
CERTIFICATE OF CORRECTION

PATENT NO. : 11,254,651 B2
APPLICATION NO. : 16/076307
DATED : February 22, 2022
INVENTOR(S) : Yu et al.

Page 1 of 1

It is certified that error appears in the above-identified patent and that said Letters Patent is hereby corrected as shown below:

In the Claims

Column 69,
Line 1, "in R" should read --in $R^f$--;
Line 61, "claim 5" should read --claim 11--.

Column 74,
Line 23, "thereof," should read --thereof;--.

Signed and Sealed this
Twenty-eighth Day of March, 2023

Katherine Kelly Vidal
*Director of the United States Patent and Trademark Office*